(12) United States Patent
Cheikh et al.

(10) Patent No.: US 7,423,203 B2
(45) Date of Patent: Sep. 9, 2008

(54) METHOD OF INCREASING YIELD IN A PLANT AND GENES USEFUL THEREFOR

(75) Inventors: Nordine Cheikh, Davis, CA (US); Dane Fisher, Richfield, NC (US); Rebecca Thompson, St. Charles, MO (US)

(73) Assignee: Monsanto Technology, LLC, St. Louis, MO (US)

( * ) Notice: Subject to any disclaimer, the term of this patent is extended or adjusted under 35 U.S.C. 154(b) by 126 days.

(21) Appl. No.: 10/841,796

(22) Filed: May 7, 2004

(65) Prior Publication Data

US 2004/0237138 A1 Nov. 25, 2004

Related U.S. Application Data

(60) Provisional application No. 60/468,518, filed on May 7, 2003.

(51) Int. Cl.
*A01H 5/00* (2006.01)
(52) U.S. Cl. .................................................. 800/320.1
(58) Field of Classification Search ............... 800/295, 800/298, 278; 536/23.1; 435/320.1
See application file for complete search history.

(56) References Cited

U.S. PATENT DOCUMENTS 5,716,837 A * 2/1998 Barry et al. ................. 800/284
6,235,971 B1 * 5/2001 Barry et al. ................. 800/295
6,632,602 B1 * 10/2003 Sheen et al. .................... 435/6

OTHER PUBLICATIONS

Doerks et al. Trends Genet. 1998. 14(6):248-250.*
Gonzali et al. Plant Science. 2002. 163:943-954.*
Middleton et al. Biochemical Society Transactions. 1990. 18(2):180-183.*
Jang et al. The Plant Cell 9: Jan. 5-19, 1997.*
Xiao et al. Plant Molecular Biology 44: 451-461, 2000.*

* cited by examiner

*Primary Examiner*—Elizabeth F McElwain
(74) *Attorney, Agent, or Firm*—Thomas P. McBride; Thomas E. Kelley

(57) ABSTRACT

A method of changing the activity of hexokinases in a plant sink comprising introducing into the plant a gene encoding a fungal hexokinase. In the method, the gene is expressed in the plant seed tissue to produce the protein, thereby changing characteristics of hexokinase activity in the seed of the plant.

2 Claims, 15 Drawing Sheets

METHOD OF INCREASING YIELD IN A PLANT AND GENES USEFUL THEREFOR

CROSS REFERENCE TO RELATED APPLICATIONS

This application claims benefit under 35 USC §119(e) of U.S. provisional application Serial No. 60/468,518 filed May 7, 2003, the entirety of which is hereby incorporated by reference hereto.

FIELD OF THE INVENTION

The present invention relates generally to the field of plant molecular biology, and more specifically to plant cells or plants transformed to contain and express a DNA molecule encoding a hexokinase that confers changes in carbon containing constituents in the seed of a crop plant.

BACKGROUND OF THE INVENTION

Corn is used in a broad range of applications; from ethanol and animal feed production to production of products directly for human consumption, for example breakfast cereal. On average, 20% of corn produced in the U.S. is used for domestic food and industrial purposes. Material output from processed corn includes starch for direct use or chemical modification, starch used as a degradative feedstock for the manufacture of ancillary products, and coproducts/byproducts such as gluten feed, gluten meal and corn oil. As the list of products containing corn-derived ingredients grows, so does the percentage of the corn that is utilized by the corn processing industry.

A central component in the direct, or indirect, use of corn for many products is starch. The central importance of starch to plant development and to food, feed, and industrial markets has motivated researchers across many years to look for mechanisms that control starch biosynthesis. Mutants of maize that affect seed starch deposition have been instrumental in characterizing the biochemistry of starch synthesis. Considerable research effort continues to explore the metabolic systems involved in synthesizing starch, but in addition molecular techniques are being used to analyze and study genes that encode enzymes known to be critical in starch biosynthesis. In discovering which regions of the genes encode metabolism-controlling aspects of the enzymes, scientists are beginning to manipulate starch metabolism through genetic engineering.

The use of seed starch mutants in various crop plants and the production of transgenic plants that over- or under-express specific proteins has indicated that many proteins/enzymes are capable of affecting starch biosynthesis in storage organs. This can occur directly, by impacting the proteins that: (1) produce the substrate(s) for starch synthesis, (2) initiate the glucose polymerization process and elongate the structure into macromolecules, or (3) alter the structure of the polymers once the elongation process has begun. In addition to a direct impact on starch metabolism, starch production can also be negatively impacted by dysfunction or deficiency of proteins that are catalysts in sugar metabolism or act as transporters of intermediary compounds. Proteins involved in assimilate transport, such as the brittle-1 protein of maize endosperm amyloplast membranes, sucrose carrier proteins or others homologous to the hexose transporter of the chloroplast can also affect starch synthesis by restricting the availability of substrates for normal starch and/or sugar metabolism.

Sucrose is considered to be the primary metabolite utilized in the synthesis of starch, although seed grown in vitro with the reducing sugars, glucose or fructose, also produce starch. In simple terms, the sugars are converted into the sugar nucleotides, ADP-glucose and UDP-glucose, either directly or via phosphorylated carbohydrate intermediates. The sugar nucleotides are substrates for the synthase enzymes that polymerize the glucosyl portion of the molecules into long chains of glucose. The polymers remain essentially linear (amylose) or become branched (amylopectin) and combine in a specific fashion to become granules of starch. The proportion of sugar and other carbohydrates, protein, and oils in seeds and fruits is controlled, at least in part, by the conversion of hexose sugars to hexose-6-phosphate by hexose kinase. The hexose kinases can be divided into three general categories according to their hexose substrate specificity. Hexokinase (HK) can phosphorylate glucose and fructose, while glucokinase (GK) and fructokinase (FK) are relatively specific for the respective hexose isomer. Most genomes contain multiple hexose kinases and multiple isozymes of the enzymes. Many plant tissues express hexose kinases.

The hexose sugars used in the production of starch in the seed are moved in the phloem primarily as sucrose. Sucrose is the primary energy source moved from photosynthetic portions of the plant to areas where the energy is utilized or storage of the energy occurs. Sucrose is translocated from the phloem to the seed via specialized cells. Once to the seed, the sucrose (a disaccharide) is often broken down into monosaccharides. Hexokinases add a high energy phosphate to the monosaccharides making hexose sugars available for use in catabolic and anabolic pathways. It has recently been shown that hexokinase expression in an entire plant (driven by the constitutive cauliflower mosaic virus 35S promoter, CaMV35S) leads to growth repression and decreased true leaf development (Xiao, et al., *Plant Molecular Biology* 44:451, 2000). It has also been shown that overexpression of hexokinase driven by the CaMV 35S promoter inhibits growth, reduces photosynthesis, and induces rapid senescence in tomatoes (Dai, et al., *Plant Cell* 11:1253, 1999). When these published data are taken together they show that expression of hexokinases under a constitutive promoter is not advantageous for obtaining plants with increased yield and suggest that an overexpression of hexokinase in seed would lead to seed senescence. The present invention, however, shows that the targeted expression of a fungal hexokinase to seeds does not lead to seed senescence, but rather leads to the augmentation of specific aspects of yield, for example, measures of starch per seed.

SUMMARY OF THE INVENTION

The present invention provides a plant expressing a fungal hexokinase gene preferentially in the seeds of the plant thereby influencing carbon sequestration within the seed. In a preferred embodiment, a polynucleotide encoding a fungal hexokinase is regulated by an operably linked promoter directing enhanced expression of the hexokinase coding sequence in seeds as compared to other plant tissues and provides seeds having increased starch content and decreased sugar content.

More specifically, the invention provides a recombinant DNA molecule that comprises in the 5' to 3' direction; a promoter providing enhanced expression in a plant seed, or parts thereof, operably linked to a DNA polynucleotide that encodes a fungal hexokinase, operably linked to a 3' transcription termination DNA polynucleotide. In a preferred embodiment the DNA polynucleotide encoding the fungal hexokinase is capable of hybridizing to SEQ ID NO: 1, under stringent conditions, or encodes a protein substantially identical to yeast hexokinase A (SEQ ID NO: 2). Moreover, to obtain the desired yield benefits, the promoter that provides enhanced expression in a plant seed is selected from the group consisting of an endosperm enhanced promoter, an embryo enhanced promoter, or an aleurone enhanced promoter.

The invention also provides transgenic plants containing the recombinant DNA molecule herein described. In another embodiment, transgenic plants of the present invention expressing a fungal hexokinase may also contain a second recombinant DNA molecule that expresses a transcription factor, polypeptide, enzyme or the like involved in carbohydrate and sugar metabolism, photosynthesis, or respiration and photorespiration in a manner working cooperatively with the fungal hexokinase expression in the seed to increase starch content, increase or decrease oil, or change the amount of other carbon containing compounds in the seed, and/or decrease sugar content, or increase/decrease other carbon containing compounds. Seed or hybrid seed derived from or directly obtained from a transgenic event containing the hexokinase transgene of the present invention is also an aspect of the present invention and such seed may advantageously be coated with a pesticide for cooperative effect.

A method of producing a plant with increased starch content in its seeds is also provided. This method comprises the steps of inserting into the genome of a plant cell a recombinant DNA molecule comprising;

a) a seed-enhanced promoter that functions in plants, operably linked to;

b) a DNA polynucleotide that encodes a fungal hexokinase, operably linked to;

c) a transcription termination polynucleotide that functions in plants;

wherein said promoter is heterologous with respect to the fungal hexokinase polynucleotide;

obtaining a transformed plant cell containing the recombinant DNA molecule;

regenerating a transformed plant therefrom; and identifying and selecting a transformed plant having an increased starch content in its seed. Similarly, methods for producing transgenic plants having decreased hexose sugar in its seeds or increased oil content in its seeds by introduction of the recombinant DNA molecule of this invention are also possible. Specific embodiments of the above methods could include the methods above wherein said fungal hexokinase is selected from SEQ ID NOs: 2, 6, 8, 10, 12, 14, 16, 18, 20, 22, 24, 26, 28, and 30.

Also provided is a plant according to the invention wherein the number of copies of the recombinant DNA molecule according to the invention is modulated in the seed of said plant through breeding.

A fungal hexokinase that is identical to, hybridizes to, or is 70%, 75%, 80% 85%, 90%, 95%, 98%, or greater identity to at least one polynucleotide selected from the group consisting of SEQ ID NOs: 22, 24, 26, 28, or 30 is also provided herein.

Also provided herein are commodities, food and/or feed ingredients resulting from the milling and processing of seeds or plant tissues of the present invention containing the hexokinase described herein, e.g. oil, meal, flour or other end- or by-product. Food and feed products containing or made with at least one of these commodities, food or feed ingredient are also encompassed herein.

BRIEF DESCRIPTION OF THE FIGURES AND SEQUENCE LISTING

Figure 4:
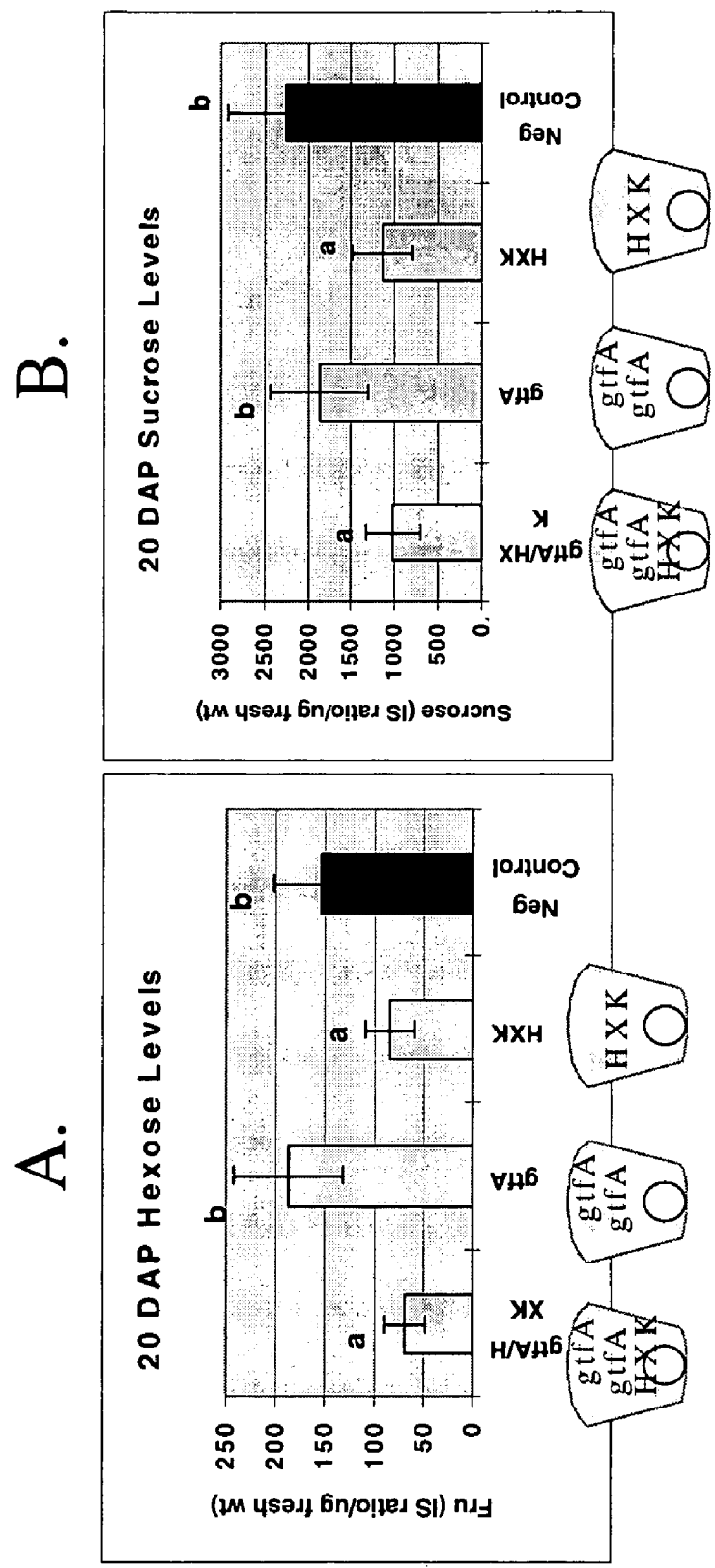

FIG. 4 is a graph showing sugar levels for each genotype expressed in units of an internal standard ratio/milligram fresh weight. The metabolites are relative to an internal standard, which therefore produces a ratio. The mean is shown with standard deviation. P-values were calculated to determine statistically significant differences. Differences significant at 90% or greater are shown. Negative control is wildtype elite corn germplasm type B kernels, 20 days after planting. Error bars show standard deviation. A.) Hexose levels B.) Sucrose levels.

Figure 5:
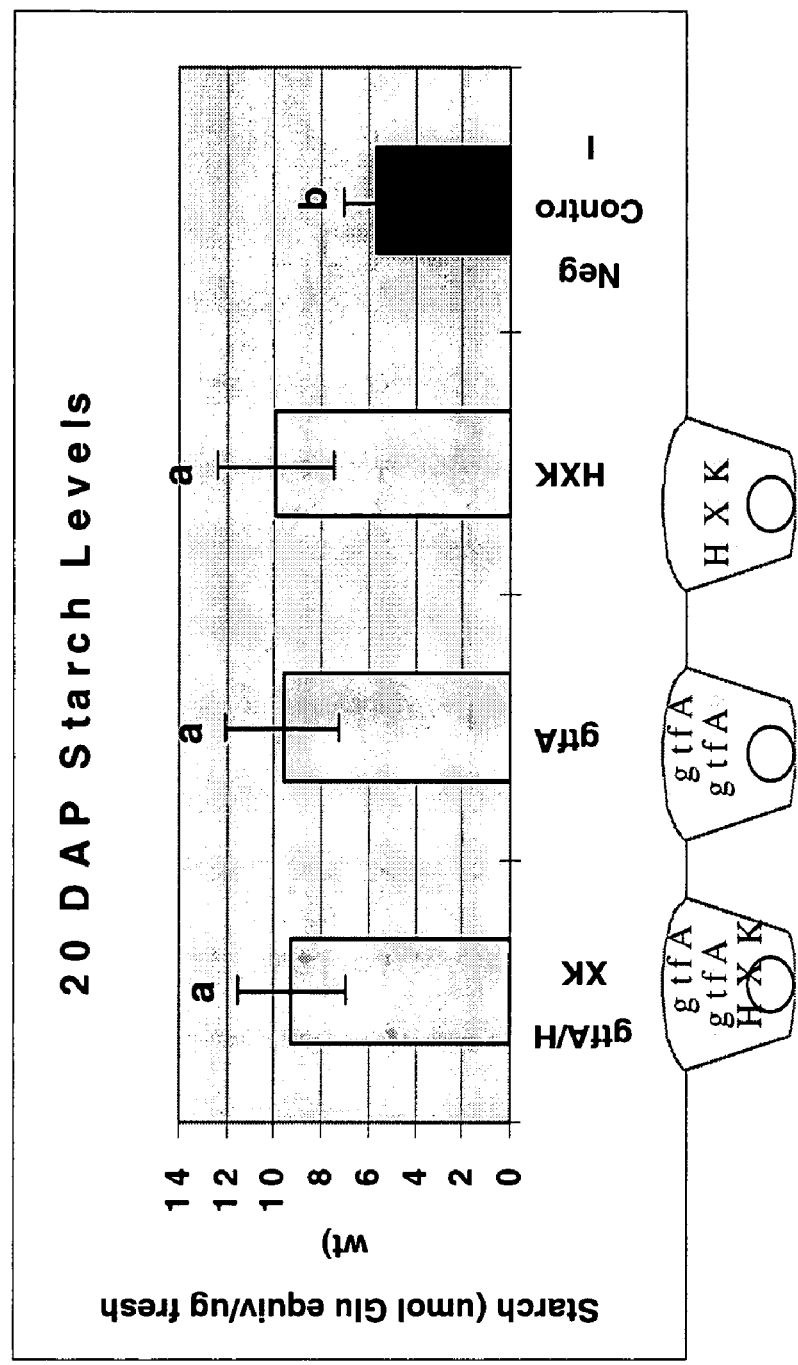

FIG. 5 shows a graph of in vivo starch levels for each genotype. The mean is shown with standard deviation. P-values were calculated to determine statistically significant differences. Differences significant at 90% or greater are shown. Negative control is wildtype elite corn germplasm type B kernels, 20 days after planting.

Figure 6:
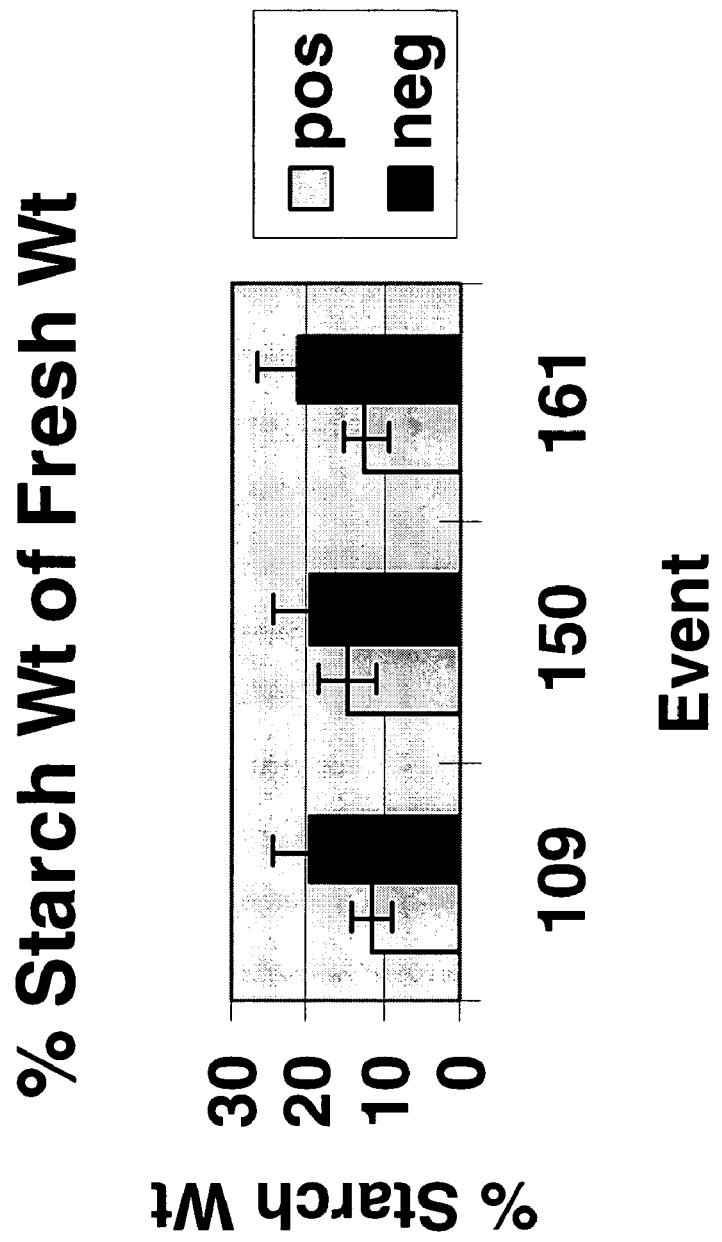

FIG. 6 shows a graph of starch weight. Starch weight was measured by weighing the starch pellet and relating back to fresh weight to determine the percent of fresh weight that is starch. Three events were measured, both positive and negative, as determined by Western analysis. Error bars show standard deviation.

Figure 7:
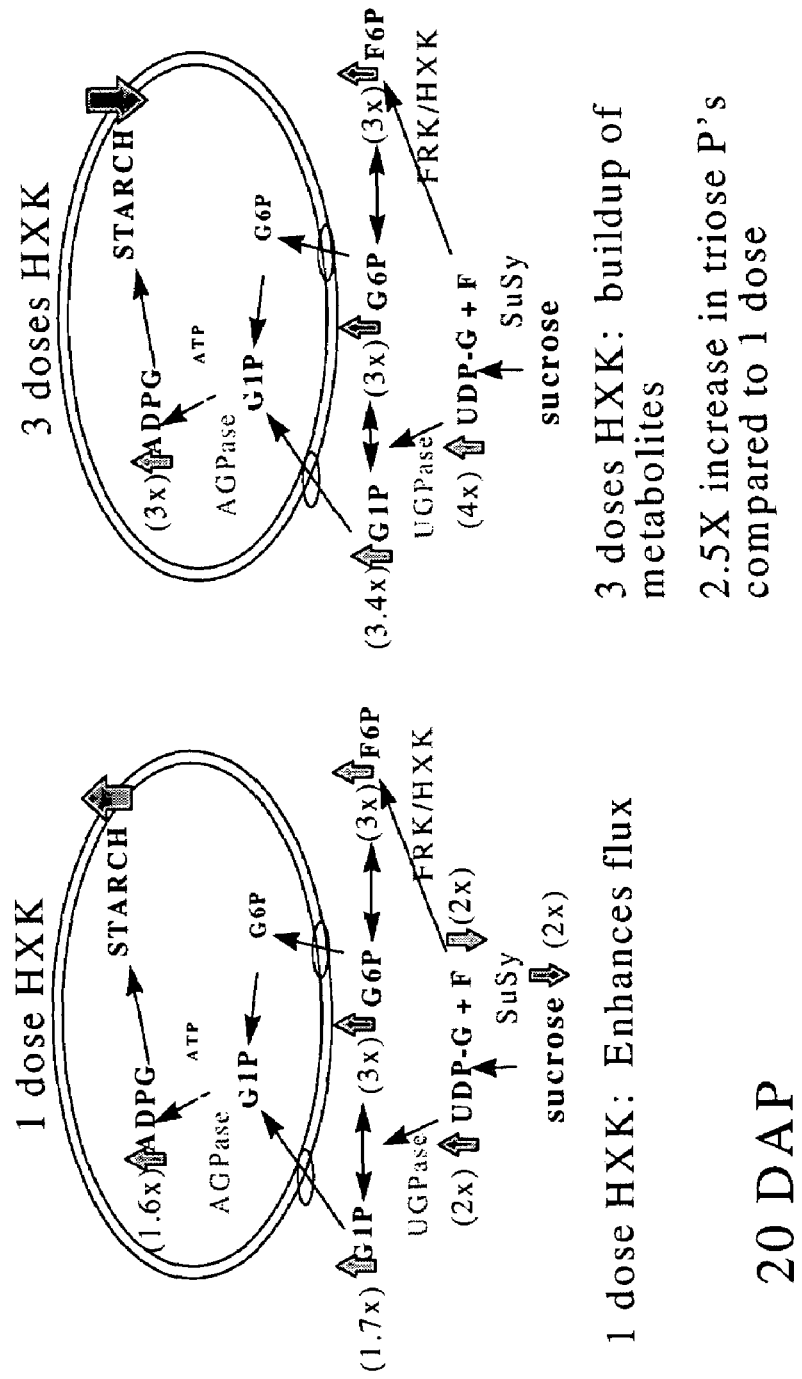

FIG. 7 shows a metabolite analysis of seed, wherein the seed contains one to three copies of the hexokinase transgene in the endosperm. Because the endosperm is triploid, two paternal and one maternal genome, one to three copies of the transgene can be selected by selecting the number of copies and the parents of origin.

Figure 8:
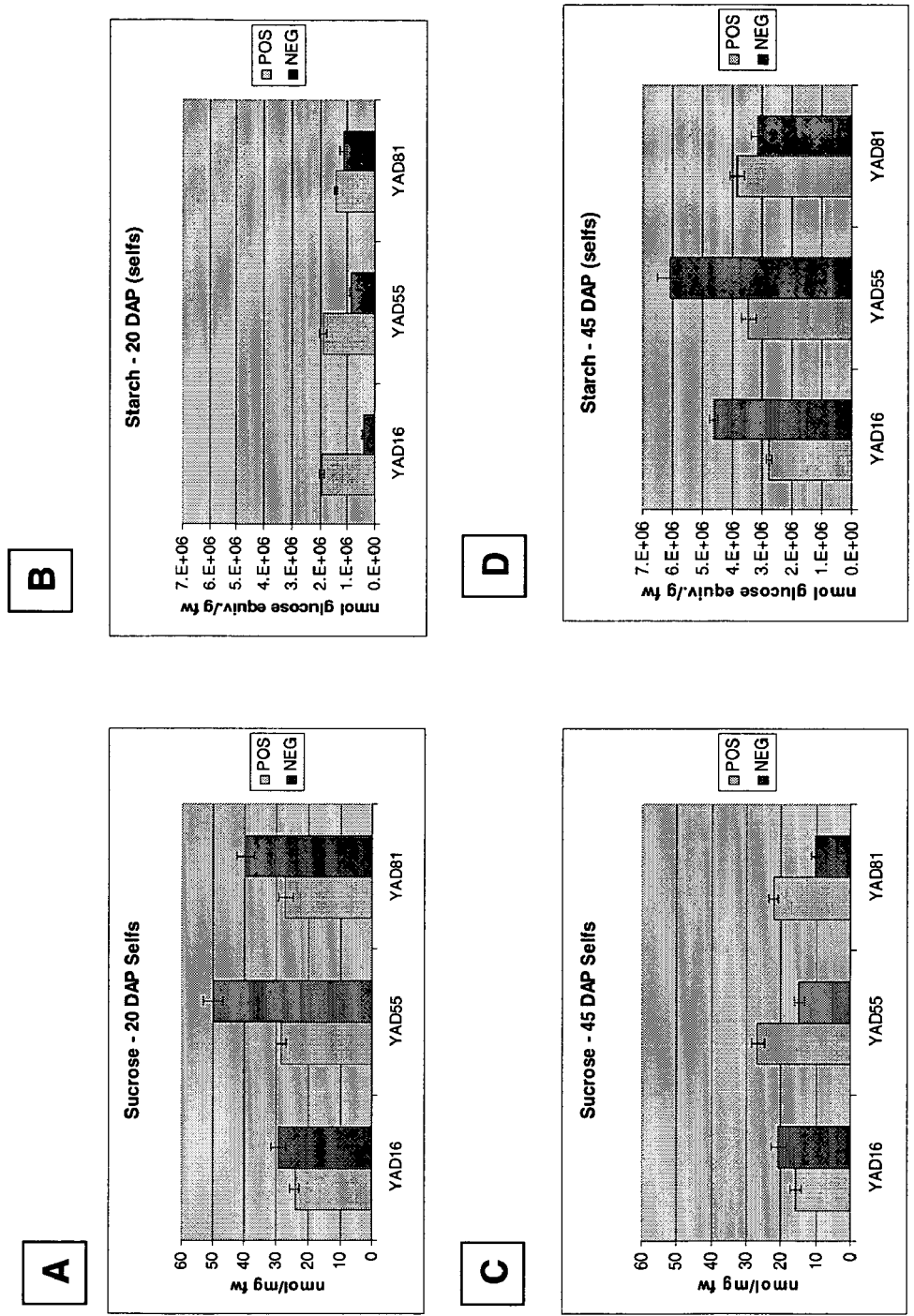

FIG. 8 shows Sucrose and starch results for selfed material. Sucrose is expressed in nmol sucrose/mg fresh weight. Starch is expressed in nmol glucose equivalents/mg fresh weight. A: Sucrose in 20 DAP kernels. B: Starch in 20 DAP kernels. C: Sucrose in 45 DAP kernels. D: Starch in 45 DAP kernels. Error bars represent standard error of the mean.

Figure 9:
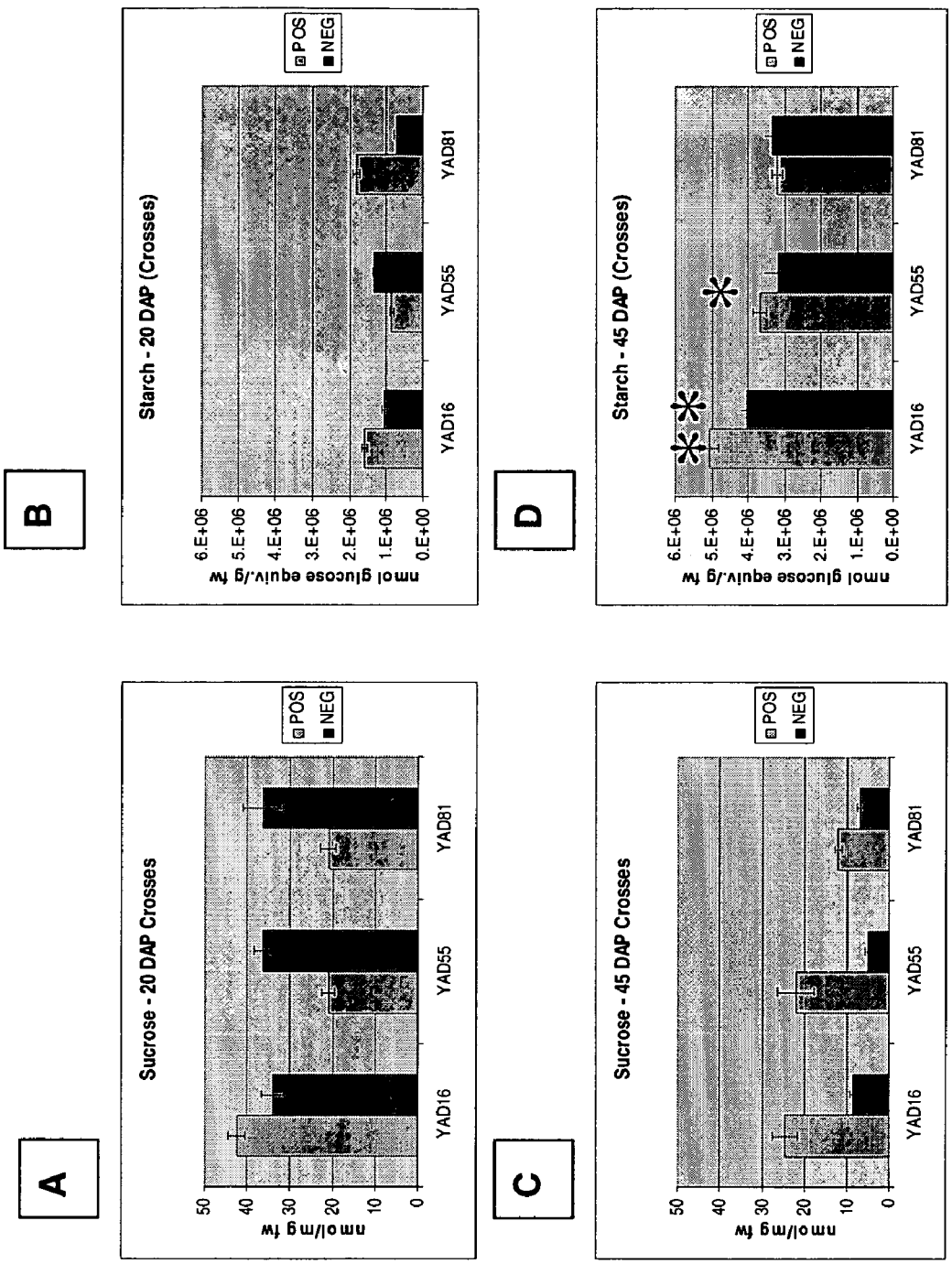

FIG. 9 shows sucrose and starch results for crossed material. Sucrose is expressed in nmol sucrose/mg fresh weight. Starch is expressed in nmol glucose equivalents/mg fresh weight. A: Sucrose in 20 DAP kernels. B: Starch in 20 DAP kernels. C: Sucrose in 45 DAP kernels. D: Starch in 45 DAP kernels. Error bars are standard error of the means. *$p<0.05$, **$p<0.01$.

Figure 10:
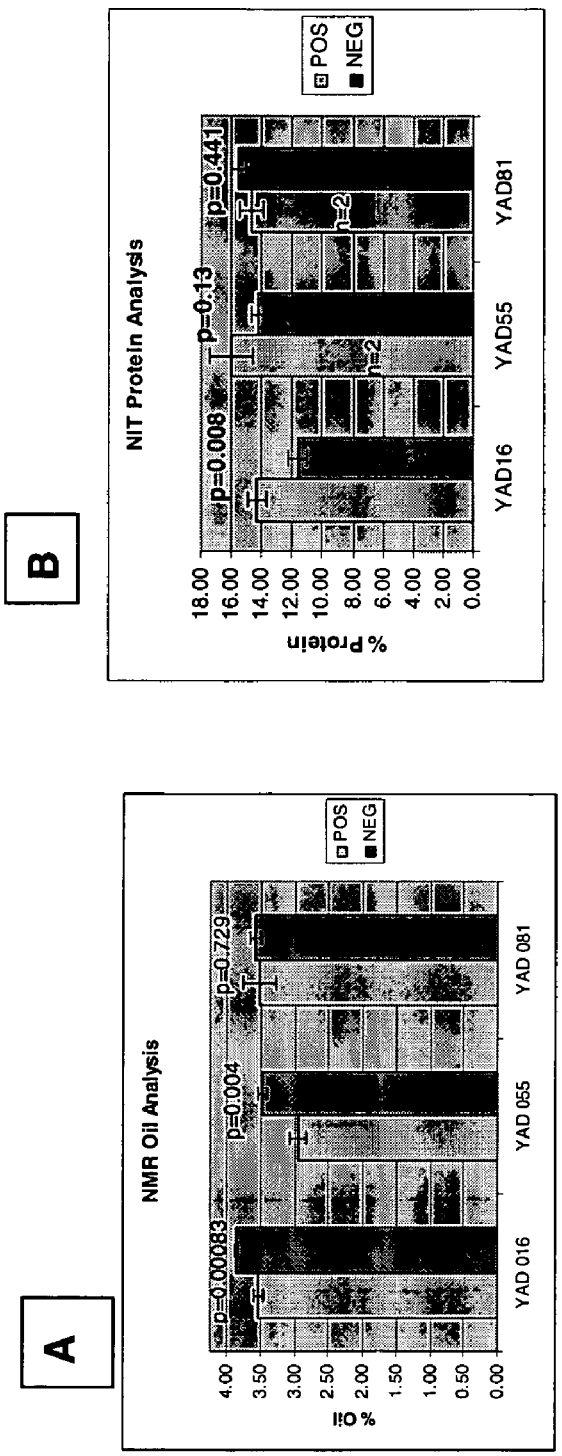

FIG. 10 shows kernel phenotypes of 45 DAP crossed material. A: Oil Content measured by NMR. B: Protein Content measured by NIT.

Figure 11:
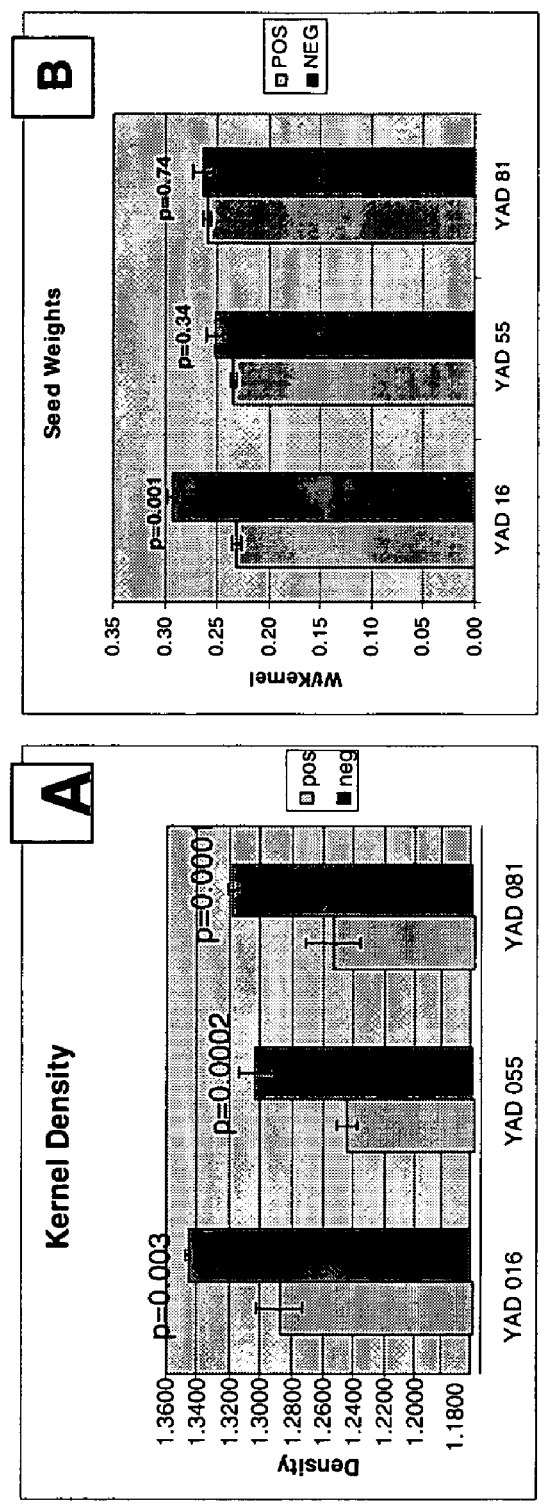

FIG. 11 shows A) Kernel density measured by Micromeritics AccuPyc Pycnometer, and B) Seed weights.

Figure 12:
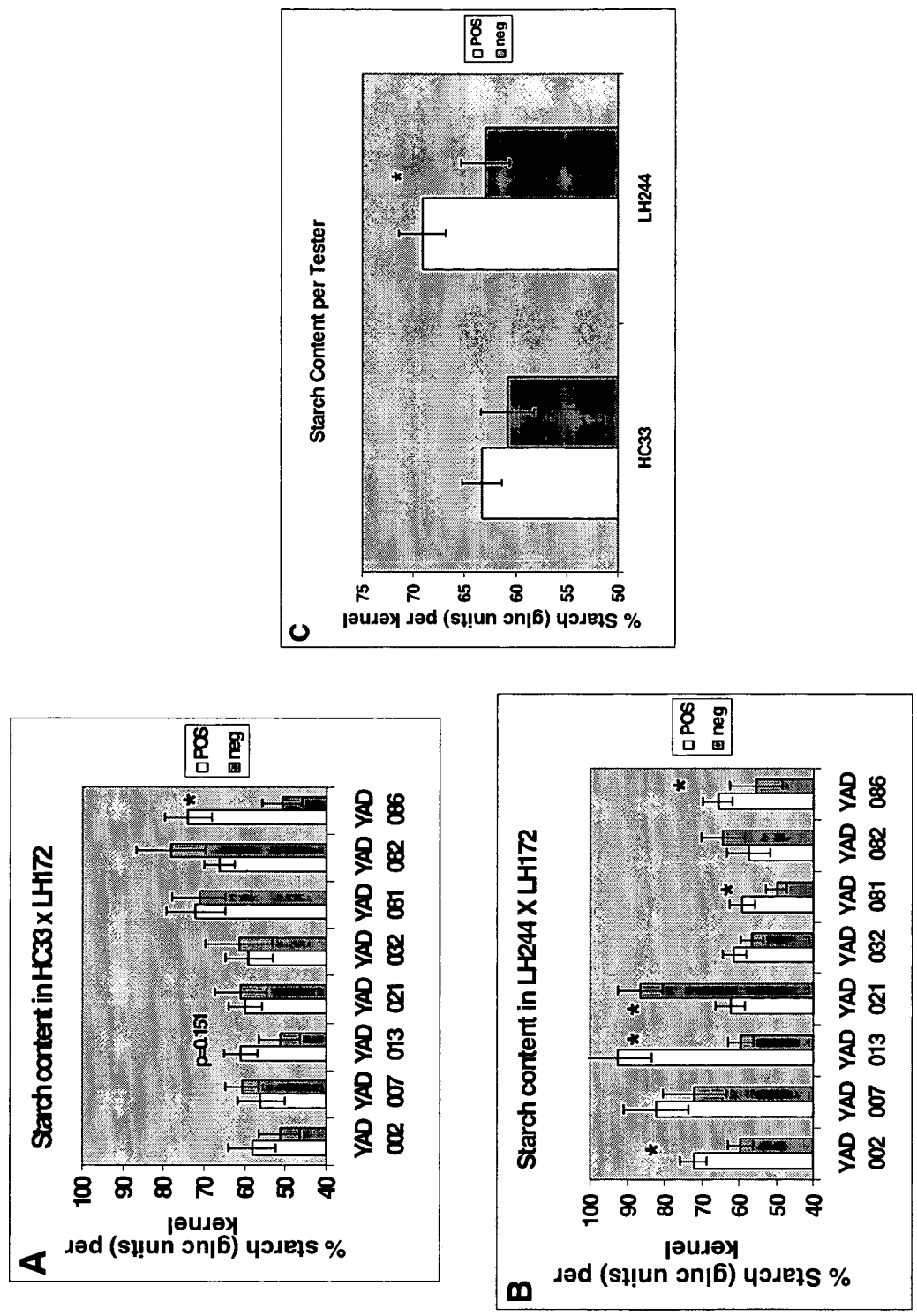

FIG. 12. Starch in mature kernels. A. Total starch of HC33× LH172. B. Total Starch of LH244×LH172. A and B, Each bar represents measurements from 15 ears. The average with the standard error are graphed. C. Overall total starch in kernels of each tester with the events averaged. P value less than 0.1 are noted with an asterisk.

Figure 13:
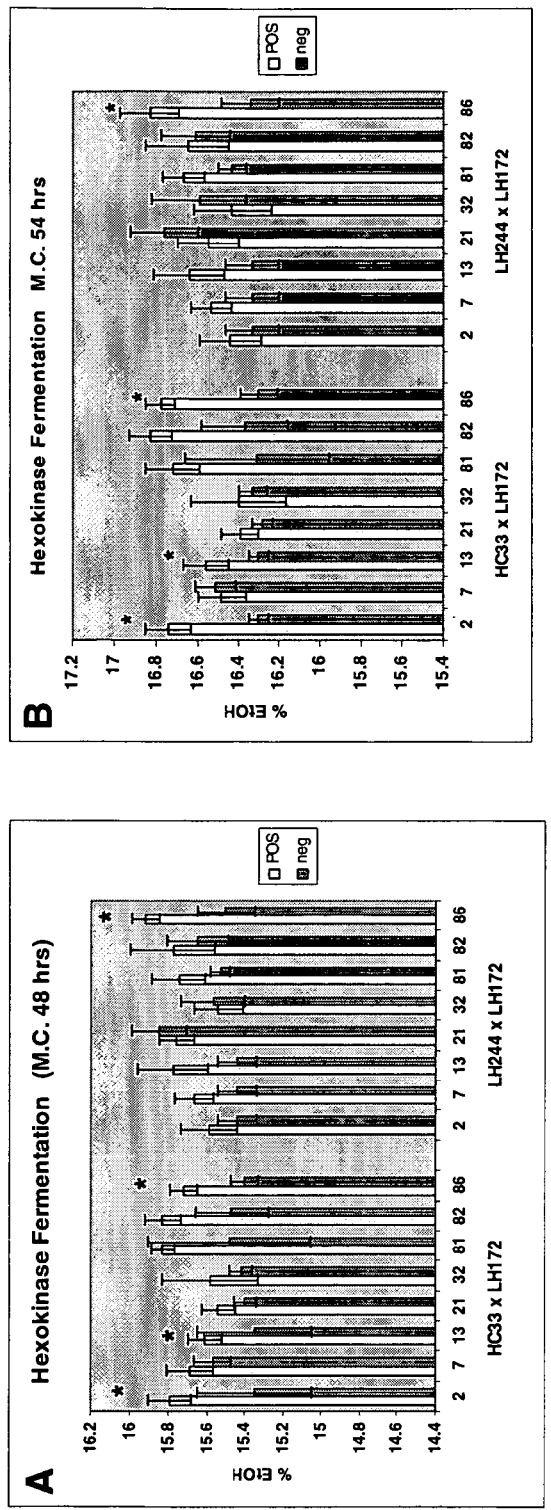

FIG. 13. Hexokinase Fermentation Results after 48 and 54 hours. The average with the standard error is graphed. P value less than 0.1 are noted. A. Fermentation at 48 hours. B. Fermentation at 54 hours.

Figure 14:
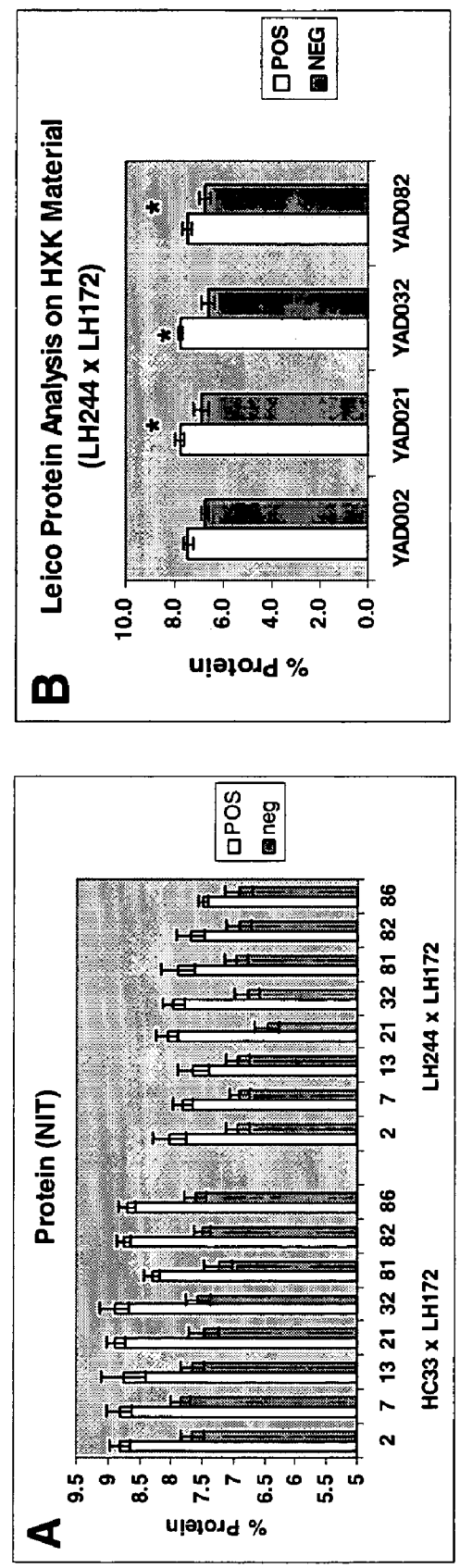

FIG. 14. Protein Results by NIR and by Leico. The average with the standard error is graphed. P value less than 0.1 are noted. A. Protein by NIR B. Leico analysis of 4 events in LH244×LH172.

Figure 15:
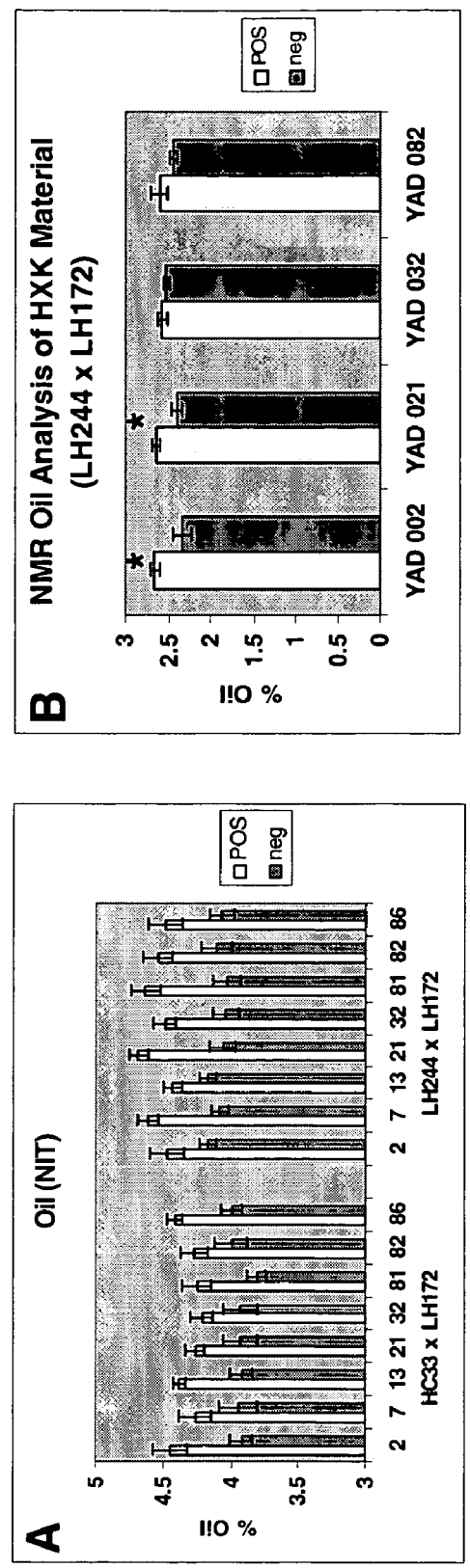

FIG. 15. Oil Results by NIT and by Bulk NMR. The average with the standard error is graphed. P value less than 0.1 are noted. A. Oil by NIT B. Bulk NMR results of 4 events in LH244×LH172.

The invention can be more fully understood from the following detailed description and the accompanying Sequence Listing that form a part of this application.

DETAILED DESCRIPTION OF THE INVENTION

It has been discovered that the preferential expression of a polynucleotide encoding a fungal hexokinase (SEQ ID NO:1 and 2) in the seeds and/or seed tissue of a plant unexpectedly increases the yield of the plant as measured by starch content in the seeds. Therefore, in a first aspect the present invention provides nucleic acid molecules encoding a fungal protein having the biological activity of a hexokinase. The nucleic acid of the invention may be in the form of RNA or DNA, including cDNA, synthetic DNA or genomic DNA. The DNA may be double-stranded or single-stranded, and if single-stranded can be either the coding strand or non-coding strand. An RNA analog may be for example, mRNA or a combination of ribo- and deoxy-ribonucleotides. Illustrative examples of a polynucleotide of the present invention are provided. As used herein, "fungus or fungal" refers to any of numerous eukaryotic organisms of the kingdom Fungi, which lack chlorophyll and vascular tissue and range in form from a single cell to a body mass of branched filamentous hyphae that often produce specialized fruiting bodies. The kingdom includes, but is not limited to, the yeasts, molds, smuts, and mushrooms.

A polynucleotide of the invention typically is at least fifteen (15) nucleotides (or base pairs, bp) in length. In some embodiments, a polynucleotide is about 20 to 100 nucleotides in length, or about 100 to 500 nucleotides in length. In other embodiments, a polynucleotide is greater than about 1000 nucleotides in length and encodes a polypeptide having the amino acid sequence of SEQ ID NOs: 2, 6, 8, 10, 12, 14, 16, 18, 20, 22, 24, 26, 28, or 30.

A polynucleotide of the present invention may encode analogs or derivatives of a polypeptide having the deduced amino acid sequence of SEQ ID NO:2, 6, 8, 10, 12, 14, 16, 18, 20, 22, 24, 26, 28, or 30. Such fragments, analogs or derivatives include, for example, naturally occurring allelic variants, non-naturally occurring allelic variants, deletion variants and insertion variants, that do not substantially alter the function of the polypeptide.

The present invention also comprises polynucleotides that hybridize specifically to a fungal hexokinase disclosed herein (SEQ ID NOs: 1, 5, 7, 9, 11, 13, 15 ,17 ,19, 21 ,23, 25, 27, or 29). Such a polynucleotide typically is at least 15 nucleotides in length, and more preferably at least 50 nucleotides in length. These polynucleotides hybridize specifically to a strand of a nucleic acid molecule of this invention, i.e., they do not or only to a small extent hybridize to nucleic acid sequences encoding other proteins. Hybridization typically involves a method by which the presence of DNA sequences in a target nucleic acid mixture are identified by hybridization to a labeled oligonucleotide or DNA fragment probe. Hybridization conditions are sequence dependent and will be different in different circumstances. As used herein "stringent conditions" are selected to be about 5° C. lower than the thermal melting point (Tm) for the specific sequence at a defined ionic strength and pH. The "thermal melting point" is the temperature (under defined ionic strength and pH) at which 50% of a target molecule hybridizes to a completely complementary molecule. Appropriate stringent conditions which promote DNA hybridization, for example, 6.0× sodium chloride/sodium citrate (SSC) at about 45° C., followed by a wash of 2.0×SSC at 50° C., are known to those skilled in the art or can be found in *Current Protocols in Molecular Biology*, John Wiley & Sons, N.Y. (1989), 6.3.1-6.3.6. For example, the salt concentration in the wash step can be selected from a low stringent condition of about 2.0×SSC at 50° C. to a high stringency of about 0.2×SSC at 50° C. In addition, the temperature in the wash step can be increased from low stringent conditions at room temperature, about 22° C., to high stringent conditions at about 65° C. Both temperature and salt concentration may be varied, or either the temperature or the salt concentration may be held constant while the other variable is changed. For the purposes of this disclosure, stringent conditions include at least one wash in 2.0×SSC at a temperature of at least about 50° C. for 20 minutes, or equivalent conditions. As is understood in the art, high stringency conditions are used to identify nucleic acids that have a high degree of homology to the probe used in the hybridization study.

A polynucleotide within the scope of this invention has at least about 70% sequence identity, preferably about 80% sequence identity, more preferably about 90% sequence identity and most preferably about 95% sequence identity to SEQ ID NOs: 1, 5, 7, 9, 11, 13, 15, 17, 19, 21, 23, 25, 27, or 29. Optimal alignment of sequences may be conducted by computer programs utilizing algorithms (GAP, BESTFIT, FASTA, and TFASTA in the Wisconsin Genetics Software Package Release 7.0-10.0, Genetics Computer Group, 575 Science Dr., Madison, Wis.). The reference nucleic acid or protein may be a full-length molecule or a portion of a longer molecule. Identity is determined typically by comparison of a first nucleic acid or protein sequence, when optimally aligned (with appropriate nucleotide or amino acid insertions or deletions totaling less than 20 percent of the reference sequence over the window of comparison) with the other nucleic acid (or its complementary strand) or protein over a comparison window of at least 20 nucleotide or amino acid positions; at least 50 nucleotide or amino acid positions, at least 100 nucleotide or amino acid positions; or over the entire length of the first nucleic acid or protein.

A polynucleotide of the invention may be obtained by chemical synthesis, isolation and cloning from fungal genomic DNA or other means known to the art, including the use of PCR technology carried out using oligonucleotides corresponding to SEQ ID NO:2, SEQ ID NO:3 or portions of SEQ ID NOs: 1, 5, 7, 9, 11, 13, 15, 17, 19, 21, 23, 25, 27, or 29. PCR refers to the technique in which a target nucleic acid is amplified in a manner similar to that described in U.S. Pat. No. 4,683,195, herein incorporated by reference hereto.

The proteins encoded by the various variants of the nucleic acid molecules of this invention exhibit certain common characteristics. Enzyme activity, molecular weight, immunological reactivity, conformation, etc. may be a part of such characteristics as well as physical properties such as mobility in gel electrophoresis, solubility, stability, pH-optimum, temperature optimum, etc.

A polypeptide of this invention comprises an isolated polypeptide having the amino acid sequence of SEQ ID NOs: 2, 6, 8, 10, 12, 14, 16, 18, 20, 22, 24, 26, 28, or 30 as well as derivatives and analogs thereof. It should also be appreciated that certain amino acid substitutions can be made in protein sequences without affecting the function of the protein. Generally, conservative amino acid substitutions or substitutions of similar amino acids are tolerated without affecting protein function. Similar amino acids can be those that are similar in size and/or charge properties. An "isolated" polypeptide or nucleic acid sequence is substantially separated or purified away from other nucleic acid sequences with which the protein or nucleic acid is normally associated in the cell of the organism in which the protein or nucleic acid naturally occurs, i.e., expression of a protein in a non-host organism or other chromosomal or extrachromosomal DNA. The term embraces proteins or nucleic acids that are biochemically purified so as to substantially remove contaminating proteins or nucleic acids and other cellular components. The term also embraces recombinant proteins or nucleic acids and chemically synthesized proteins or nucleic acids.

The invention further relates to vectors, especially plasmids, and other vectors common in genetic engineering, that contain the above-described polynucleotides. Preferably, the polynucleotides contained in the vectors are operably linked to regulatory elements that provide for the transcription and expression of a polypeptide or protein in eukaryotic cells. Typically, the recombinant DNA molecule containing the polynucleotide of the present invention will include in an operably linked manner, in the 5' to 3' direction of transcription, a transcription initiation control region capable of promoting, initiating and/or modulating transcription and translation in a plant cell (a promoter region), the polynucleotide encoding a fungal hexokinase, and a transcription and translation termination region (otherwise referred to as a 3' untranslated region). As used herein, a first nucleic acid sequence is "operably linked" with a second nucleic acid sequence when the sequences are so arranged that the first nucleic acid sequence affects the function of the second nucleic-acid sequence. Preferably, the two sequences are part of a single contiguous nucleic acid molecule and more preferably are adjacent. A "recombinant" nucleic acid or "recombinant DNA molecule" is made by an artificial combination of two otherwise separated segments of sequence, e.g., by chemical synthesis or by the manipulation of isolated segments of nucleic acids by genetic engineering techniques. The terms "recombinant DNA construct", "recombinant vector", "expression vector" or "expression cassette" refer to any agent such as a plasmid, cosmid, virus, BAC (bacterial artificial chromosome), autonomously replicating sequence, phage, or linear or circular single-stranded or double-stranded DNA or RNA nucleotide sequence, derived from any source, capable of genomic integration or autonomous replication, comprising a DNA molecule in which one or more DNA sequences have been linked in a functionally operative manner.

As used herein, a "promoter" refers to a DNA sequence that binds an RNA polymerase (and often other transcription factors as well) and promotes transcription of a downstream DNA sequence. Said sequence can be an RNA that has function, such as rRNA (ribosomal RNA) or tRNA (transfer RNA). Often, the RNA produced is a hetero-nuclear (hn) RNA that has introns that are spliced out to produce an mRNA (messenger RNA). A "plant promoter" is a native or non-native promoter that is functional in plant cells. Constitutive promoters are functional in most or all tissues of a plant throughout plant development. Tissue-, organ- or cell-specific promoters are expressed only or predominantly in a particular tissue, organ, or cell type, respectively. "Specifically" expressed and "enhanced" expression are used interchangeably herein. "Enhanced expression" is used herein to refer to any promoter that provides an increased expression in a single tissue or developmental stage, or under a particular environmental condition, but causes expression, even significant expression, in other tissue(s), or developmental stage(s), or environmental condition(s).

Temporally regulated promoters are functional only or predominantly during certain periods of plant development or at certain times of day, as in the case of genes associated with circadian rhythm, for example. Inducible promoters selectively express an operably linked DNA sequence in response to the presence of an endogenous or exogenous stimulus, for example by chemical compounds (chemical inducers) or in response to environmental, hormonal, chemical, and/or developmental signals. Inducible or regulated promoters include, for example, promoters regulated by light, heat, stress, flooding or drought, phytohormones, wounding, cold, or chemicals such as ethanol, jasmonate, salicylic acid, or safeners.

For the most part, any plant promoter can be used as a 5' regulatory sequence to modulate expression of a particular gene or genes, such as a plant RNA polymerase II promoter. When fused to heterologous DNA sequences, such promoters typically cause the fused sequence to be transcribed in a manner that is similar to that of the gene sequence with which the promoter is normally associated. Promoter fragments that include regulatory sequences can be added (for example, fused to the 5' end of, or inserted within, an active promoter having its own partial or complete regulatory sequences. Alternatively, heterologous regulatory sequences can be added to the 5' upstream region of an inactive, truncated promoter, e.g., a promoter including only the core TATA and, sometimes, the CCAAT sequences.

Promoters are typically comprised of multiple distinct "cis-acting transcriptional regulatory elements," or simply "cis-elements," each of which can confer a different aspect of the overall control of gene expression. The promoter sequences of the present invention may contain "cis elements" that modulate gene expression. Cis elements can be part of the promoter, or can be upstream or downstream of said promoter. Cis elements (or groups thereof), acting at a distance from a promoter are often referred to as repressors or enhancers. Enhancers act to upregulate the transcriptional initiation rate of RNA polymerase at a promoter, repressors act to decrease said rate. In some cases, the same elements can be found in a promoter and an enhancer or repressor. Cis elements are generally sites where transcription factors bind to the DNA and modulate the rate at which RNA polymerase binds to the promoter.

Examples of constitutive promoters that are active in plant cells include but are not limited to the nopaline synthase (NOS) promoters; the cauliflower mosaic virus (CaMV) 19S and 35S (sometimes called 35S herein, or a derivative of which is called e35S {as described in U.S. Pat. Nos. 5,359, 142, 5,196,525, 5,322,938, 5,164,316, and 5,424,200 each of which being hereby incorporated by reference hereto }); the tobacco mosaic virus promoter; the figwort mosaic virus promoters; and actin promoters, such as the *Arabidopsis* actin gene promoter.

The term "tissue-specific promoter" means a regulatory sequence that causes an enhancement of transcription from a downstream gene in specific cells or tissues at specific times during plant development, such as in vegetative tissues or reproductive tissues. Examples of tissue-specific promoters under developmental control include promoters that initiate transcription only (or primarily only) in certain tissues, such as vegetative tissues, e.g., roots, leaves or stems, or reproductive tissues, such as fruit, ovules, seeds, pollen, pistils, flowers, or any embryonic tissue. Reproductive tissue specific promoters may be, e.g., ovule-specific, embryo-specific, endosperm-specific, integument-specific, seed coat-specific, pollen-specific, petal-specific, sepal-specific, or some combination thereof. One skilled in the art will recognize that a tissue-specific promoter may drive expression of operably linked sequences in tissues other than the target tissue. Thus, as used herein a tissue-specific promoter is one that drives expression preferentially in the target tissue, but may also lead to expression in other tissues as well.

In a preferred embodiment of the invention, the fungal hexokinase of this invention is operably linked to a seed-specific or seed-enhanced promoter, or promoter that directs expression in the seed or some specific tissue or region therein.

Promoters derived from genes encoding embryonic storage proteins, which includes the gene encoding the 2S storage protein from *Brassica napus* (Dasgupta et al.,,Gene 133:301-302 (1993)); the 2s seed storage protein gene family from *Arabidopsis;* the gene encoding oleosin 20 kD from *Brassica napus* (GenBank No. M63985); the genes encoding oleosin A (GenBank No. U09118) and oleosin B (GenBank No. U09119) from soybean; the gene encoding oleosin from *Arabidopsis* (GenBank No. Z17657); the gene encoding oleosin 18 kD from maize (GenBank No. J05212, Lee, Plant Mol. Biol. 26:1981-1987 (1994)); and the gene encoding low molecular weight sulphur rich protein from soybean (Choi et al., Mol. Gen. Genet. 246:266-268 (1995)), can also be used. Promoters derived from zein encoding genes (including the 15 kD, 16 kD, 19 kD, 22 kD, 27 kD, and gamma genes) (Pedersen et al., Cell 29: 1015-1026 (1982)) can be also used. The zeins are a group of storage proteins found in maize endosperm.

Other examples of possible suitable regulatory sequences include introns, 3' non-coding regions such as poly A sequences, insulator regions and the like. Molecular biological techniques for identifying, obtaining and using such regulatory elements in combination with the polynucleotides of the present invention are known in the art.

The present invention further relates to transgenic plant cells and transgenic plants having been transformed to contain and express the fungal hexokinase polynucleotide of the invention. "Transformed", "transfected", or "transgenic" refers to a cell, tissue, organ, or organism into which has been introduced a foreign nucleic acid, such as a recombinant vector. Preferably, the introduced nucleic acid is integrated into the genomic DNA of the recipient cell, tissue, organ or organism such that the introduced nucleic acid is inherited by subsequent progeny. A "transgenic" or "transformed" cell or organism also includes progeny of the cell or organism and progeny produced from a breeding program employing such a "transgenic" plant as a parent in a cross and exhibiting an altered phenotype resulting from the presence of a recombinant construct or vector. The method of transformation is not critical to the current invention and various methods of plant transformation are currently known and available. For example, the introduction of DNA sequences into plants and/or plant cells can be accomplished by Agrobacterium mediated transformation, viral vector mediated transformation, electroporation, and microprojectile bombardment mediated transformation (particle gun or biolistics methods. The DNA sequence may also be transformed directly into the plastid genome by plastid transformation. As used herein, the term "plastid" means the class of plant cell organelles that includes amyloplasts, chloroplasts, chromoplasts, elaioplasts, eoplasts, etioplasts, leucoplasts, and proplastids. These organelles are self-replicating, and contain what is commonly referred to as the "chloroplast genome," a circular DNA molecule that ranges in size from about 120 to about 217 kb, depending upon the plant species, and which usually contains an inverted repeat region.

This invention is applicable to dicotyledonous and monocotyledonous species alike and is readily applicable to new and/or improved transformation techniques. For efficient production of transgenic plants from plant cells or plant tissue, it is desirable that the plant tissue used for transformation possess a high capacity for regeneration. Techniques are known in the art to regenerate plants from transformed plant tissue cultures of plant cells.

The transgenic plants produced in accordance with this invention may, as previously stated, be any dicotyledonous or monocotyledonous species and are preferably from useful species such as rice, maize (corn), peas, soybean, alfalfa, cassava, potato, cotton, and cereals (e.g., barley, oats, rye, triticale and wheat). Fertile transgenic plants so produced would produce transgenic seed that can be grown and selfed (or outcrossed and selfed) to obtain seeds homozygous for the fungal hexokinase polynucleotide. Seeds can be analyzed in order to identify those homozygotes having the desired expression level and pattern of the DNA molecule containing the selected seed specific promoter and polynucleotide encoding for a fungal hexokinase. The invention also relates to propagules and propagation material of the plants of the invention. As used herein, "propagule" includes all products of meiosis and mitosis, including but not limited to, seed and parts of the plant able to propagate a new plant. For example, propagule includes a shoot, root, or other plant part that is capable of growing into an entire plant. Propagule also includes grafts where one portion of a plant is grafted to another portion of a different plant (even one of a different species) to create a living organism. Propagule also includes all plants and seeds produced by cloning or by bringing together meiotic products, or allowing meiotic products to come together to form an embryo or fertilized egg (naturally or with human intervention). As used herein yeast regularly refers to *Saccharomyces cerevissiae* but could also include *Schizosacchoramyces pombe* and other varieties (from the genus *Pichia,* for example). Corn refers to *Zea Mays* and all species and varieties that can be bred with it. Wheat refers to all of *Triticum aestivum* varieties including but not limited to spring, winter, and all facultative wheat varieties. Wheat includes any other wheat species, including but not limited to durum wheat (*Triticum durum*), spelt (*Triticum spelta*), emmer (*Triticum dicoccum*), and wild wheat (*Triticum monococcum*). Wheat also includes any species that can be bred with any of the aforementioned wheat species. Soybeans refers to *Glycine max* and any species or variety that can be bred with it. Rice refers to *Oriza sativa* and any species or variety that can be bred with it. Barley refers to *Hordeum vulgare* and any species or variety that can be bred with it. Oats refers to *Avena sativa* and any species or variety that can be bred with it. Canola is a coined name recently given to seed, oil, and meal produced by genetically modified rapeseed plants, oilseed rape (*Brassica napus* L.) and turnip rape (*B. campestris* L), herein canola includes all rapeseed plants and organisms that can be bred with them. *Agrobacterium tumefaciens* as used herein includes all strains and types of this species. Cotton refers to all plants in the genus *Gossypium* and all plants that can be bred with them.

A method according to the invention comprises introducing a DNA molecule containing a promoter functional in plant cells operably linked to a nucleic acid sequence encoding a fungal, specifically a yeast, hexokinase and producing a plant (as well as fertile progeny plant of such a plant) from the transformed plant cell. Progeny includes fertile descendants of a particular plant or plant line.

The compositions, plants and methods according to the invention described herein are useful in that the transgenic plants produced hereby have desirable yield characteristics in the sink tissues, e.g. seed, manifested by increased starch content. The transgenic plants of the present invention may also be characterized as having decreased sugar content and/or decreased oil content as compared to a native or non-transformed plant of the same species. Plants and other organisms contain multiple forms of hexokinases, and these generally include glucokinases (EC 2.7.1.2) and fructokinases (EC 2.7.1.4). It is demonstrated herein that the activity of a fungal hexokinase, particularly yeast hexokinase A, is not inhibited by increased concentrations of fructose. The expression of fungal hexokinase in sink tissues, such as seeds, provides a way to maintain and enhance sucrose utilization by alleviating any buildup of hexose that may otherwise feedback inhibit sucrose synthase. This enhancement of sucrose synthase increases the flux of carbon through the pathway leading to increases in starch, sugar, and/or other carbohydrates leading to an increase in yield as measured by increasing seed weight and/or starch production.

Hexokinase is believed to function via the phosphorylation of hexose sugars within the seed. These phopohorylated sugars are then available for any catabolic or anabolic pathway. By introducing other transgenes that cause expression of other enzymes within the seed these sugars can be directed toward specific pathways or functions. One possible mechanism for this is the expression of a sucrose phosphorylase gene (gtfA) such as the gene from *Strepococcus mutans*. It has previously been shown that the expression of this enzyme in maize endosperm can result in an increase in starch accumulation (U.S. Pat. Nos. 6,235,971, 6,222,098, and 5,716,837 herein incorporated by reference hereto for a description of genes encoding sucrose phosphorylase). The addition of a fungal hexokinase to a plant or seed already expressing gtfA may further enhance the effects of gtfA by alleviating any fructose pool that potentially could inhibit sucrose synthase. Thus, a nucleic acid sequence encoding a fungal hexokinase may be used in conjunction with other useful genes to further enhance the yield of a plant as measured by starch accumulation or carbon assimilation in the seeds. Other useful genes for use in combination with yeast hexokinase includes, but is not limited to, sucrose phosphorylase, ADP- or UDP-glucose pyrophosphorylase, sedoheptulose 1,7-bisphosphatase enzyme, soluble starch synthase, starch branching enzyme, granule bound starch synthase, starch phosphorylases, starch debranching enzymes, isoamylases, disproportionating enzymes, fructose 1,6 biphosphate aldolase, acetyl coA carboxylase, oleate hydroxylase, 3-ketoacetyl coA sythase III, 3-ketoacetyl coA sythase II, 3-ketoacetyl coA sythase I, Malonyl CoA:ACP transcyclase, 3-ketoacetyl-ACP reductase, sucrose synthase, sucrose phosphate synthase, sucrose phosphate phosphorylase, phosphoglucomutases, phosphoglucoisomerases 2,3-trans-enoyl-ACP reductase, 3-hydroxyacyl-ACP dehydratase, β-GDH, and α-GDH, KAS I dependent FAS, KAS II dependent FAS, stearoyl-ACP desaturase, Palmitoyl-ACP thioesterase, oleoyl-ACP thioesterase, oleate elongase, acyl-CoA:glycerol-3-phosphate acyltransferase, acyl-CoA:lysophosphotidate acyltransferase, phosphotidate phosphatase, CDP-choline:diacylglycerol cholinephosphotransferase, oleate desaturase FAD2, linoleate desaturase FAD3, acyl-CoA:sn-1 acyllysophosphatidylcholine acyltransferase, and oleosin.

It may also be desirable to provide a transgenic seed of the present invention whereby the copy number of the transgene in the transgenic event is modulated in a manner to enhance yield. Modifications of the number of copies of a transgene in a seed can be modulated by controlling whether the transgene is present in a heterozygous or homozygous state within the parent plants, or is not present at all (nullizygous). This modification of copy number can be controlled, for example, by using a homozygous male and nullizygous female. This combination would create a seed wherein one copy of the transgene was present in the embryo and two copies would be present in the endosperm. The number of copies of the transgene can be controlled to create plants, wherein the seeds can have different numbers of copies of the transgene in the endosperm. Changing the number of copies of the transgene in the endosperm can lead to changes in the amount of transgene protein produced within the seed, and change aspects of yield. The copy number can vary from one to three copies if there is one transgene with one insertion site per haploid genome. The yield of the transgenic event is then modulated by the change in the amount and ratio of the carbon containing compounds in the seed resulting from the change in copy number of the transgene.

A seed of the present invention comprising a transgenic event as described herein may also be treated with a pesticide. It is believed that the combination of a transgenic seed exhibiting increased starch content and thereby increased yield as a result of the production of a fungal hexokinase of the invention within the cells of the transgenic seed or plant grown from the seed coupled with treatment of the seed with certain chemical or protein pesticides may provide unexpected synergistic advantages to seeds having such treatment, including unexpectedly superior efficacy for yield potential.

When it is said that some effects are "synergistic", it is meant to include the synergistic effects of the combination on the pesticidal activity (or efficacy) of the combination of the transgenic event and the pesticide.

Pesticides suitable for use in seed treatments in the invention include pyrethrins and synthetic pyrethroids; oxadizine derivatives; chloronicotinyls; nitroguanidine derivatives; triazoles; organophosphates; pyrrols; pyrazoles; phenyl pyrazoles; diacylhydrazines; biological/fermentation products; and carbamates. Known pesticides within these categories are listed in *The Pesticide Manual*, 11th Ed., C. D. S. Tomlin, Ed., British Crop Protection Council, Farnham, Surry, UK (1997). Particularly preferred synthetic pyrethroids are tefluthrin, lambda cyhalothrin, bifenthrin, permethrin and cyfluthrin. Even more preferred synthetic pyrethroids are tefluthrin and lambda cyhalothrin, and yet more preferred is tefluthrin. Insecticides that are oxadiazine derivatives are useful in the seed treatments and coatings along with compositions and seeds of the present invention. The oxadizine derivatives that are preferred for use in the present invention are those that are identified in U.S. Pat. No. 5,852,012.

Chloronicotinyl insecticides are also useful in the subject invention. Chloronicotinyls that are preferred for use in the subject composition are described in U.S. Pat. No. 5,952,358, and include acetamiprid ((E)-N-[(6-chloro-3-pyridinyl)methyl]-N'-cyano-N-methyleneimidamide, CAS RN 135410-20-7), imidacloprid (1-[(6-chloro-3-pyridinyl)methol]-N-nitro-2-imidazolidinimime, CAS RN 138261-41-3), and nitenpyram (N-[(6-chloro-3-pyridinyl)methyl]-N-ethyl-N'-methyl-2-nitro-1,1-ethenediamine, CAS RN 120738-89-8).

Nitroguanidine insecticides are useful in the present invention. Such nitroguanidines can include those described in U.S. Pat. Nos. 5,633,375, 5,034,404 and 5,245,040.

Pyrrols, pyrazoles and phenyl pyrazoles that are useful in the present invention include those that are described in U.S. Pat. No. 5,952,358. Diacylhydrazines that are useful in the present invention include halofenozide (4-chlorobenzoate-2-benzoyl-2-(1,1-dimethylethyl)-hydrazide, CAS RN 112226-61-6), methoxyfenozide (RH-2485; N-tert-butyl-N'-(3-methoxy-o-toluoyl)-3,5-xylohydrazide, CAS RN 161050-58-4), and tebufenozide (3,5-dimethylbenzoic acid 1-(1,1-dimethylethyl)-2,(4-ethylbenzoyl)hydrazide, CAS RN 112410-23-8).

Triazoles, such as amitrole (CAS RN 61-82-5) and triazamate are useful in the present invention. A preferred triazole is triazamate (ethyl [[1-[(dimethylamino)carbonyl]-3-(1,1-dimethylethyl)-1H-1,2,4-triazol-5-yl]thio]acetate, CAS RN 112143-82-5).

Biological/fermentation products, such as avermectin (abamectin, CAS RN 71751-41-2) and spinosad (XDE-105, CAS RN 131929-60-7) are useful in the present invention.

Organophosphate insecticides are also useful as one of the components of seed treatments and coatings in the present invention. Preferred organophophate insecticides include acephate (CAS RN 30560-19-1), chlorpyrifos (CAS RN 2921-88-2), chlorpyrifos-methyl (CAS RN 5598-13-0), diazinon-(CAS RN 333-41-5), fenamiphos (CAS RN 22224-92-6), and malathion (CAS RN 121-75-5). In addition, carbamate insecticides are useful in the present invention. Preferred carbamate insecticides are aldicarb (CAS RN 116-06-3), carbaryl (CAS RN 63-25-2), carbofuran (CAS RN 1563-66-2), oxamyl (CAS RN 23135-22-0) and thiodicarb (CAS, RN 59669-26-0).

When an insecticide is described herein for use in a seed treatment and/or seed coating, it is to be understood that the description is intended to include salt forms of the insecticide as well as any isomeric and/or tautomeric form of the insecticide that exhibits the same insecticidal activity as the form of the insecticide that is described.

The insecticides that are useful in the seed treatments and coatings of the present invention can be of any grade or purity that pass in the trade as such insecticide. Other materials that accompany the insecticides in commercial preparations as impurities can be tolerated in the subject methods and compositions, as long as such other materials do not destabilize the composition or significantly reduce or destroy the activity of any of the activities or components or the transgenic event. One of ordinary skill in the art of the production of insecticides can readily identify those impurities that can be tolerated and those that cannot.

It is preferred that the seed treatments and coatings described herein be used along with transgenic seeds of the present invention. Although it is believed that the seed treatments can be applied to a transgenic seed in any physiological state, it is preferred that the seed be in a sufficiently durable state that it incurs no damage during the treatment process. Typically, the seed would be a seed that had been harvested from the field; removed from the transgenic plant; and separated from any other non-seed plant material. The seed would preferably also be biologically stable to the extent that the treatment would cause no biological damage to the seed. In one embodiment, for example, the treatment can be applied to seed corn that has been harvested, cleaned and dried to a moisture content below about 15% by weight. In an alternative embodiment, the seed can be one that has been dried and then primed with water and/or another material and then re-dried before or during the treatment with the pesticide. Within the limitations just described, it is believed that the treatment can be applied to the seed at any time between harvest of the seed and sowing of the seed. As used herein, the term "unsown seed" is meant to include seed at any period between the harvest of the seed and the sowing of the seed in the ground for the purpose of germination and growth of the plant.

When it is said that unsown seed is "treated" with the pesticide, such treatment is not meant to include those practices in which the pesticide is applied to the soil, rather than to the seed. For example, such treatments as the application of the pesticide in bands, "T"-bands, or in-furrow, at the same time as the seed is sowed are not considered to be included in the present invention.

The pesticide, or combination of pesticides, can be applied "neat", that is, without any diluting or additional components present. However, the pesticide is typically applied to the seeds in the form of a pesticide formulation. This formulation may contain one or more other desirable components including but not limited to liquid diluents, binders to serve as a matrix for the pesticide, fillers for protecting the seeds during stress conditions, and plasticizers to improve flexibility, adhesion and/or spreadability of the coating. In addition, for oily pesticide formulations containing little or no filler, it may be desirable to add to the formulation drying agents such as calcium carbonate, kaolin or bentonite clay, perlite, diatomaceous earth or any other adsorbent material. Use of such components in seed treatments is known in the art. See, e.g., U.S. Pat. No. 5,876,739. The skilled artisan can readily select desirable components to use in the pesticide formulation depending on the seed type to be treated and the particular pesticide that is selected. In addition, readily available commercial formulations of known pesticides may be used, as demonstrated in the examples below.

The seeds may also be treated with one or more of the following ingredients: other pesticides, including compounds which act only below the ground; fungicides, such as captan, thiram, metalaxyl, (methoxam=resolved isomer of metalaxyl), fludioxonil, oxadixyl, and isomers of each of those materials, and the like; herbicides, including compounds selected from carbamates, thiocarbamates, acetamides, triazines, dinitroanilines, glycerol ethers, pyridazinones, uracils, phenoxys, ureas, and benzoic acids; herbicidal safeners such as benzoxazine, benzhydryl derivatives, N,N-diallyl dichloroacetamide, various dihaloacyl, oxazolidinyl and thiazolidinyl compounds, ethanone, naphthalic anhydride compounds, and oxime derivatives; fertilizers; and biocontrol agents such as naturally-occurring or recombinant bacteria and fungi from the genera *Rhizobium, Bacillus, Pseudomonas, Serratia, Trichodenna, Glomus, Gliocladium* and mycorrhizal fungi. These ingredients may be added as a separate layer on the seed or alternatively may be added as part of the pesticide composition.

Preferably, the amount of the novel composition or other ingredients used in the seed treatment should not inhibit generation of the seed, or cause phytotoxic damage to the seed.

The pesticide formulation that is used to treat the transgenic seed in the present invention can be in the form of a suspension; emulsion; slurry of particles in an aqueous medium (e.g., water); wettable powder; wettable granules (dry flowable); and dry granules. If formulated as a suspension or slurry, the concentration of the active ingredient in the formulation is preferably about 0.5% to about 99% by weight (w/w), preferably 5-40% or as otherwise formulated by those skilled in the art of applying such a formulation to the seed of a particular crop plant.

As mentioned above, other conventional inactive or inert ingredients can be incorporated into the formulation. Such inert ingredients include but are not limited to: conventional sticking agents, dispersing agents such as methylcellulose (Methocel A15LV or Methocel A15C, for example, serve as combined dispersant/sticking agents for use in seed treatments), polyvinyl alcohol (e.g., Elvanol 51-05), lecithin (e.g., Yelkinol P), polymeric dispersants (e.g., polyvinylpyrrolidone/vinyl acetate PVPIVA S-630), thickeners (e.g., clay thickeners such as Van Gel B to improve viscosity and reduce settling of particle suspensions), emulsion stabilizers, surfactants, antifreeze compounds (e.g., urea), dyes, colorants, and the like. Further inert ingredients useful in the present invention can be found in McCutcheon's, vol. 1, "*Emulsifiers and Detergents*," MC Publishing Company, Glen Rock, N.J., U.S.A., 1996. Additional inert ingredients useful in the present invention can be found in McCutcheon's, vol. 2, "*Functional Materials*," MC Publishing Company, Glen Rock, N.J., U.S.A., 1996.

The pesticides and pesticide formulations of the present invention can be applied to seeds by any standard seed treatment methodology, including but not limited to mixing in a container (e.g., a bottle or bag), mechanical application, tumbling, spraying, and immersion. Any conventional active or inert material can be used for contacting seeds with pesticides according to the present invention, such as conventional film-coating materials including but not limited to water-based film coating materials such as Sepiret (Seppic, Inc., Fairfield, N.J.) and Opacoat (Berwind Pharm. Services, Westpoint, Pa.).

The subject pesticides can be applied to a seed as a component of a seed coating. Seed coating methods and compositions that are known in the art are useful when they are modified by the addition of one of the embodiments of the combination of pesticides of the present invention. Such coating methods and apparatus for their application are disclosed in, for example, U.S. Pat. Nos. 5,918,413, 5,891,246, 5,554,445, 5,389,399, 5,107,787, 5,080,925, 4,759,945 and 4,465,017. Seed coating compositions are disclosed, for example, in U.S. Pat. Nos. 5,939,356, 5,882,713, 5,876,739, 5,849,320, 5,834,447, 5,791,084, 5,661,103, 5,622,003, 5,580,544, 5,328,942, 5,300,127, 4,735,015, 4,634,587, 4,383,391, 4,372,080, 4,339,456, 4,272,417 and 4,245,432, among others.

Useful seed coatings contain one or more binders and at least one of the subject combinations of pesticides. Binders that are useful in the present invention preferably comprise an adhesive polymer that may be natural or synthetic and is without phytotoxic effect on the seed to be coated. The binder may be selected from polyvinyl acetates; polyvinyl acetate copolymers; ethylene vinyl acetate (EVA) copolymers; polyvinyl alcohols; polyvinyl alcohol copolymers; celluloses, including ethylcelluloses, methylcelluloses, hydroxymethylcelluloses, hydroxypropylcelluloses and carboxymethylcellulose; polyvinylpyrrolidones; polysaccharides, including starch, modified starch, dextrins, maltodextrins, alginate and chitosans; fats; oils; proteins, including gelatin and zeins; gum arabics; shellacs; vinylidene chloride and vinylidene chloride copolymers; calcium lignosulfonates; acrylic copolymers; polyvinylacrylates; polyethylene oxide; acrylamide polymers and copolymers; polyhydroxyethyl acrylate, methylacrylamide monomers; and polychloroprene.

The amount of pesticide that is used for the treatment of the seed will vary depending upon the type of seed and the type of active ingredients, but the treatment will comprise contacting the seeds with an amount of the combination of pesticides that is pesticidally effective. When insects are the target pest, that amount will be an amount of the insecticide that is insecticidally effective and when fungi are the target pest, the amount will be an amount of the fungicide that is fungicidally effective. As used herein, an insecticidally effective amount means that amount of insecticide that will kill insect pests in the larvae or pupal state of growth, or will consistently reduce or retard the amount of damage produced by insect pests and a fungicidally effective amount means that amount that will kill, reduce, retard or inhibit fungal damage produced the target fungi.

In general, the amount of pesticide that is applied to the seed in the treatment will range from about 10 gm to about 2000 gm of the active ingredient of the pesticide per 100 kg of the weight of the seed. Preferably, the amount of pesticide will be within the range of about 50 gm to about 1000 gm active per 100 kg of seed, more preferably within the range of about 100 gm to about 600 gm active per 100 kg of seed, and even more preferably within the range of about 200 gm to about 500 gm of active per 100 kg of seed weight. Alternatively, it has been found to be preferred that the amount of the pesticide be over about 60 gm of the active ingredient of the pesticide per 100 kg of the seed, and more preferably over about 80 gm per 100 kg of seed.

The pesticides that are used in the treatment must not inhibit germination of the seed and should be efficacious in protecting the seed and/or the plant during that time in the target insect's life cycle in which it causes injury to the seed or plant. In general, the coating will be efficacious for approximately 0 to 120 days after sowing.

The pesticides of the subject invention can be applied to the seed in the form of a coating. The use of a coating is particularly effective in accommodating high pesticidal loads, as can be required to treat typically refractory pests, such as corn rootworm, while at the same time preventing unacceptable phytotoxicity due to the increased pesticidal load.

The coatings formed with the pesticide are preferably of the type that are capable of effecting a slow rate of release of the pesticide by diffusion or movement through the matrix to the surrounding medium.

In addition to the coating layer, the seed may be treated with one or more of the following ingredients: other pesticides including fungicides and herbicides; herbicidal safeners; fertilizers and/or biocontrol agents. These ingredients may be added as a separate layer or alternatively may be added in the pesticidal coating layer.

The pesticide formulation may be applied to the seeds using conventional coating techniques and machines, such as fluidized bed techniques, the roller mill method, rotostatic seed treaters, and drum coaters. Other methods, such as spouted beds may also be useful. The seeds may be presized before coating. After coating, the seeds are typically dried and then transferred to a sizing machine for sizing. Such procedures are known in the art.

The pesticide-treated seeds may also be enveloped with a film overcoating to protect the pesticide coating. Such overcoatings are known in the art and may be applied using conventional fluidized bed and drum film coating techniques.

In another embodiment of the present invention, a pesticide can be introduced onto or into a seed by use of solid matrix priming. For example, a quantity of the pesticide can be mixed with a solid matrix material and then the seed can be placed into contact with the solid matrix material for a period to allow the pesticide to be introduced to the seed. The seed can then optionally be separated from the solid matrix material and stored or used, or the mixture of solid matrix material plus seed can be stored or planted directly. Solid matrix materials which are useful in the present invention include polyacrylamide, starch, clay, silica, alumina, soil, sand, polyurea, polyacrylate, or any other material capable of absorbing or adsorbing the pesticide for a time and releasing that pesticide into or onto the seed. It is useful to make sure that the pesticide and the solid matrix material are compatible with each other. For example, the solid matrix material should be chosen so that it can release the pesticide at a reasonable rate, for example over a period of minutes, hours, or days.

The present invention further embodies imbibition as another method of treating seed with the pesticide. For example, plant seed can be combined for a period of time with a solution comprising from about 1% by weight to about 75% by weight of the pesticide in a solvent such as water. Preferably the concentration of the solution is from about 5% by weight to about 50% by weight, more preferably from about 10% by weight to about 25% by weight. During the period that the seed is combined with the solution, the seed takes up (imbibes) a portion of the pesticide. Optionally, the mixture of plant seed and solution can be agitated, for example by shaking, rolling, tumbling, or other means. After imbibition, the seed can be separated from the solution and optionally dried, for example by patting or air drying.

In yet another embodiment, a powdered pesticide can be mixed directly with seed. Optionally, a sticking agent can be used to adhere the powder to the seed surface. For example, a quantity of seed can be mixed with a sticking agent and optionally agitated to encourage uniform coating of the seed with the sticking agent. The seed coated with the sticking agent can then be mixed with the powdered pesticide. The mixture can be agitated, for example by tumbling, to encourage contact of the sticking agent with the powdered pesticide, thereby causing the powdered pesticide to stick to the seed.

The present invention also provides a transgenic corn seed that has been treated with a pesticide by the method described above.

The treated seeds of the present invention can be used for the propagation of corn plants in the same manner as conventional treated corn seed. The treated seeds can be stored, handled, sowed and tilled in the same manner as any other pesticide treated seed. Appropriate safety measures should be taken to limit contact of the treated seed with humans, food or feed materials, water and birds and wild or domestic animals.

Agronomically and commercially important products and/or compositions of matter including but not limited to animal feed, commodities, and seed products and by-products that are intended for use as food for human consumption or for use in compositions that are intended for human consumption including but not limited to flour, meal, syrup, oil, starch, foods containing seeds or seed parts and seed by-products, and the like are intended to be within the scope of the present invention if these products and compositions of matter contain detectable amounts of the nucleotide sequences set forth herein or are derived from or obtained directly from a seed containing a transgenic event of the present invention. Such products and/or compositions are also referred to herein as biological samples. The biological samples can be derived from the transgenic event of the present invention, either from the plant, the plant tissue, or the seed produced by the plant.

All publications and published patent documents cited in this specification are incorporated herein by reference to the same extent as if each individual publication or patent application is specifically and individually indicated to be incorporated by reference.

The following examples are included to demonstrate embodiments of the invention. It should be appreciated by those of skill in the art that the techniques disclosed in the examples that follow represent techniques discovered by the inventors to function well in the practice of the invention. However, those of skill in the art should, in light of the present disclosure, appreciate that many changes can be made in the specific embodiments which are disclosed and still obtain a like or similar result without departing from the spirit and scope of the invention, therefore all matter set forth or shown in the accompanying drawings and examples is to be interpreted as illustrative and not in a limiting sense.

EXAMPLES

Example 1

PCR of Hexokinase From Yeast and Cloning to Create pMON45006

The complete coding sequence of yeast hexokinase (yHxkA) (SEQ ID NO:1) was PCR amplified from yeast genomic DNA based upon publicly available sequence data (Genbank gi:171736, using primers ATAGGATCCATGGT-TCATTTAGGT [SEQ ID NO:2] and AAACTCGAGT-TAAGCGCCAATGAT [SEQ ID NO:3]). The 5' and 3' ends of the nucleotide sequence were modified to include a BamHI and XhoI restriction sites, respectively. This PCR product was isolated and cloned into the commercially available pET30a+vector (Moffatt, B. A. and Studier, F. W. (1986) *J. Mol. Biol.* 189, 113-130; Rosenberg, A. H., Lade, B. N., Chui, D., Lin, S., Dunn, J. J., and Studier, F. W. (1987) *Gene* 56, 125-135; Studier, F. W., Rosenberg, A. H., Dunn, J. J., and Dubendorff, J. W. (1990) *Meth. Enzymol.* 185, 60-89) from Invitrogen (Carlsbad, Calif.), using restriction enzymes. The pET30a+ vector and related vectors are available from Novagen, an affiliate of Merck KgAa, Darmstadt, Germany and details about said vector are available at the Novagen website. This vector provides a means to overexpress ykxkA in *E.coli*. Crude preparations of the recombinant protein from *E. coli* containing this vector have been shown to be insensitive to substrate inhibition by glucose and fructose up to 50 mM.

Example 2

Figure 1:
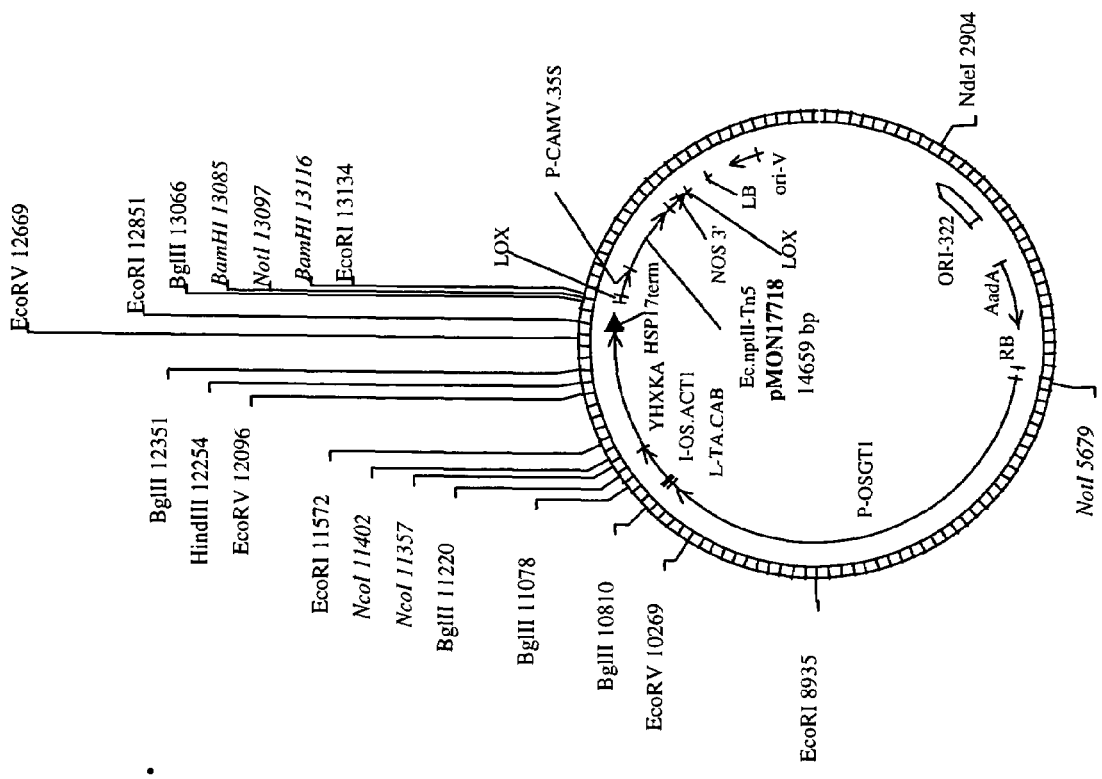
FIG. 1 shows a plasmid map for pMON 17718.
Figure 2:
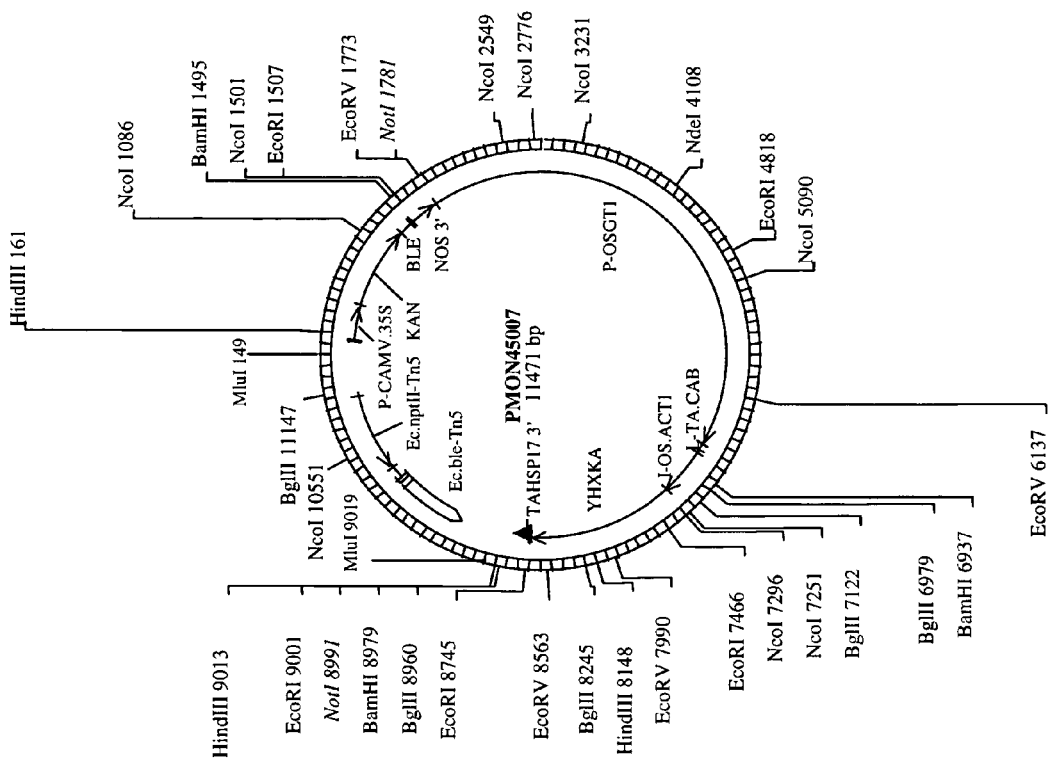
FIG. 2 shows a plasmid map for pMON45007.
Figure 3:
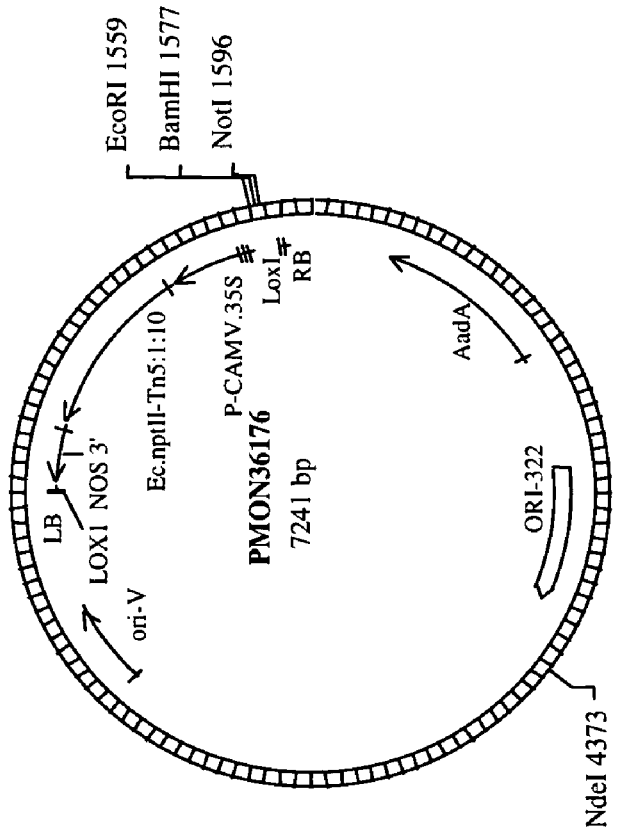
FIG. 3 shows a plasmid map for pMON36176.

Creation of Plasmid pMON17718 and 45007 pMON17718 (SEQ ID NO:33): This plasmid was used as the plant transformation vector for the creation of transgenic corn plants discussed in later examples. A portion of this sequence is shown in SEQ ID NO:34. The plasmid consists of a gene of interest expression cassette consisting of a glutelin-1 promoter (gt1), wild-type (wt) wheat cab (chlorophyll a/b binding protein) leader, rice actin 1 (ractin1) intron, yeast hexokinase A coding region (HXK) (SEQ ID NO:1) and an NOS 3' terminator. The plasmid also contains the selectable marker (NPTII). The vector was constructed by combining the Not 1 fragment containing gt 1 promoter, wt cab leader, rice actin1 intron/HXK, and NOS 3' terminator from pMON 45007 (SEQ ID NO: 32; FIG. 2) with the NotI fragment of pMON 36176 (FIG. 3) containing the selectable marker (NP-TII). The plasmid also contains the right and left border required for agrobacterium transformation. This vetor was used to transform corn plants via an agrobacterium mediated transformation process.

PMON45007 (SEQ ID NO:32) consists of a gene of interest expression cassette consisting of a glutelin-1 promoter (gt1), wild-type (wt) wheat cab (chlorophyll a/b binding protein) leader, rice actin 1 (ractin1) intron, yeast hexokinase A coding region (HXK) (SEQ ID NO:1) and an NOS 3' terminator. The plasmid also contains the selectable marker (NP-TII). The vector was constructed by combining the Not I fragment containing gt 1 promoter, wt cab leader, rice actinl intron/HXK, and NOS 3' terminator from pMON 45007 (SEQ ID NO:32) with the NotI fragment of pMON 36176 (FIG. 3) containing the selectable marker (NPTII). An MluI fragment from this plasmid was used for gun based transformation of corn.

All plasmids discussed above can be propagated in *E. coli* and transformed into *E. coli* using methods known to those skilled in the art. All plasmids can be isolated from *E. coli* via published protocols. For methods required to propagate bacteria, isolate DNA from bacteria, create and run agarose gels, isolate DNA from said gels, set up ligations, do restriction digests, transform bacteria, and for other required techniques please see Maniatis et al., Molecular Cloning: A Laboratory Manual, Second Edition (1989) Cold Spring Harbor Laboratory, Cold Spring Harbor, N.Y. and myriad other texts and references that discuss molecular biology techniques.

Example 3

Selection of Events in Corn. (pMON45007)

pMON45007 was transformed into corn plants using a particle gun mediated transformation.

The expression of yeast hexokinase A (HXK) in elite corn was confirmed by Western blot analysis using a rabbit antibody raised against HXK (Garvey, et al., *Methods in Immunology*, 3rd edition, W.A. Benjamin, Inc., Reading Mass., 1977, Part I). Homozygous material was identified from R2 seed by selfing plants identified as positive or negative at the R1 generation. Once homozygous material was obtained, experiments were initiated to determine the efficacy of HXK in the seed of a plant.

Example 4

Carbon-14 Labeling Experiment

Efficacy Studies (Elite Corn Germplasm Type B Genotype)

In order to determine whether the expression of hexokinase and GtfA (glucosyltransferase) in the seed of a plant had an effect on the seed, the following experiments was undertaken.

Crosses between gtfA containing and HXK containing plants were made to evaluate the efficacy of both genes together in a greenhouse experiment. It has been postulated that increased carbon in the seed due to the presence of a fungal hexokinase could be utilized by gtfA to increase aspects of yield. An independent event expressing the gtfA gene was used as the female parent and events expressing the HXK gene were used as the male parent in the following manner:

| 1 event gtfA(female) | | 2 events HXK(male) |
|---|---|---|
| pos | X | pos |
| pos | X | neg |
| neg | X | pos |
| neg | X | neg |

Both genes are targeted for expression in the endosperm. Endosperm tissue is triploid, receiving 2 polar nuclei from maternal and 1 from paternal gametes. Therefore, resulting positive HXK material will have 1 dose of HXK and the resulting positive gtfA material will have 2 doses of gtfA. This material was harvested on ice at 20 days post pollination (20DAP). Multiple ears from each cross were harvested to obtain a sample set that was representative of all crosses.

To evaluate HXK homozygous selfed material, HXK homozygous positive and negative material was selfed. The resulting HXK positive material contained 3 doses of HXK. This allowed us to evaluate metabolic differences between 1 and 3 doses of HXK.

Metabolite Profiling: Endosperm tissue was dissected, sectioned, and the fresh weight was recorded. The tissue was ground using 3×3 mm steel beads and shaking for 2 minutes in a 4° C. paint shaker. The metabolites were extracted using 80% ethanol with 0.1% formic acid. After centrifugation for 5 minutes at 8000 rpm, the soluble fraction (supernatant) was used to analyze the changes in sugars that are involved in the starch biosynthetic pathway. These metabolites were measured using an in-house method developed using LC/MS/MS (see below). The insoluble fraction (pellet) was analyzed for in vivo starch content by enzymatic digestion followed by glucose determination using a kit from Boehringer Mannheim (Ingelheim, Germany).

Endosperm Feeding: Endosperm tissue was sliced and dissected away from the other components of the seed. The carbon incorporation into starch was measured in vitro by using a sugar feeding assay which has been described previously (Felker, et al., *Plant Physiology* 94:996, 1990). Endosperm slices were fed 200 mM 14C-sucrose for 2 and 4 hours. The radioactivity incorporated in sucrose, fructose, glucose, and starch was determined. The amount of label in the sugars was determined by extracting the sugars in 80% EtOH and separating using a Supercosil 5 um, 4.6×250 mm LC-NH2 column on an HPLC, in line with a radiometric detector. The mobile phase was 75% Acetonitrile:25% water with a flow rate of 1 ml/min. The amount of label was quantified by constructing a standard curve using sucrose. The results are reported in micromole Glucose equivalents/micrograms fresh weight, therefore using the sucrose standard curve the result was multiplied by 2 to get to glucose equivalents. The amount of labeled carbon incorporation into starch was determined as well as the percentage of starch weight/fresh weight.

Activity Measurements: To determine the activity difference between material that contains 1 dose of HXK and 3 doses of HXK, activity assays were done. The method is the NADP coupled reaction shown below:

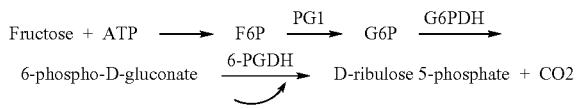

Results

Metabolite Profiling: In order to evaluate the effect of HXK on the starch biosynthesis pathway, it was important to look at any alterations in metabolites found in kernels expressing HXK. The data showed that there were no significant differences in any of the sugars when comparing gtfA+/HXK+ to gtfA−/HXK+ at this 20 DAP timepoint. The data for hexoses and sucrose is shown in FIG. 4.

There is a significant difference in the hexose and sucrose levels when 1 dose of HXK is present compared to gtfA alone or the negative control. The results indicate that the change seen in hexoses and sucrose is due to the presence of HXK at this 20 DAP timepoint The graph in FIG. 5 shows the in vivo starch measurement of the combination material.

The in vivo starch data indicates that the presence of 1 dose of HXK can increase the starch content relative to the negative control and that the level of increase is equivalent to that seen when gtfA is present. However, no synergistic gain is seen at 20 days after pollination when gtfA is combined with HXK.

The remaining metabolites measured in the starch biosynthetic pathway are shown in FIG. 6.

The results of analysis of the homozygous HXK material containing 3 doses of HXK, is remarkably different from the results seen when 1 dose of HXK is present. There were no significant changes in the hexoses or sucrose levels across 3 events comparing positive to its' negative isoline. There was a trend towards a decrease in in vivo starch in 2 of the 3 events. Under the conditions of this experiment (20 DAP), there was an average 37% decrease in % starch weight/fresh weight across 3 events as shown in FIG. 6.

The remaining metabolites measured are shown in FIG. 7 with the fold decrease compared to the negative. It appears that the level of expression of HXK is important based on the different results seen depending on the dosage of HXK. When 1 dose of HXK is present, it appears that levels of several carbon metabolites are increased and that the presence of the transgene is having the desired effect on hexose, sucrose, and starch. The level of HXK with 1 dose is sufficient to enhance the flux through the pathway without triggering any regulation that may decrease starch biosynthesis. The level of HXK with 3 doses appears to be reducing the production of starch and causing a transient backup of other metabolites in the pathway, under the conditions of this experiment.

In material containing 1 dose of HXK, sucrose and fructose are decreased as described in a previous figure. The levels of the hexose phosphates and APDG are elevated along with starch levels. The flux through the pathway is enhanced sufficiently enough to enhance starch synthesis but perhaps not enough to trigger any regulatory mechanisms. The levels of hexose phosphates and ADPG are elevated to a higher magnitude compared to 1 dose of hexokinase, however starch is decreased. The levels of triose phosphates are also much higher when 3 doses of HXK is present compared to 1 dose. It appears that when 3 doses of HXK is present, the starch biosynthesis pathway shuts down under the conditions of this experiment at 20 DAP. It may be due to regulatory mechanisms within the glycolytic or other pathways.

The metabolite analysis provides insight to what is occurring within the starch biosynthesis pathway in the endosperm. This reflects only what is occurring at 20 DAP and does not reflect what would happen at maturity. Since a positive effect on starch was seen when one dose of HXK is present, we want to determine what the effect is at seed maturity. Since we see an increase in starch at this timepoint, we will investigate if this translates into an increase in seed weight at maturity, due to the increase in starch. Also, to better understand the effect of the transgene on the pathway, it is important to measure the metabolites and starch levels at several stages of development. This would also be important for the material that is expressing 3 doses of HXK. We may be able to learn what stages of development are critical for increased starch in order to translate into increased seed weight. We can also learn which metabolites are altered and to what magnitude throughout development, when the transgene is present.

To further evaluate if HXK can enhance the effects seen with gtfA, similar types of experiments will be performed. As stated earlier, an increase in fructose was seen when gtfA was present compared to the negative control. However, the increase seen at 20 days after pollination was minimal compared to the increase seen later in development. The efficacy studies done thus far on material expressing both HXK and gtfA have been done at 20 DAP. At this timepoint we may not see a positive effect with both genes, because the fructose levels are not considerably increased. At later timepoints, when the fructose levels are higher, we may see a positive effect because HXK could act to alleviate any buildup of fructose and enhance the flow of carbon through the pathway. Again, if HXK could alleviate the buildup of fructose, then sucrose synthase would remain active and more sucrose would be hydrolyzed. Therefore, we will evaluate sugar and starch levels of material containing both HXK and gtfA at later stages of development.

In the future, we will also evaluate this approach in elite germplasms, LH 172, LH244 and possibly others. We will generate homozygous HXK material to perform similar efficacy studies to evaluate HXK alone and in combination with gtfA.

Example 6

Selection of Events in Elite Corn. (pMON 17718)

Expression of HXK in corn was confirmed in RO plants by Western analysis using a rabbit antibody raised against yeast HXK. The R1/F1 material was advanced and Taqman® (Applied Biosystems, Foster City, Calif.) analysis was done on leaf tissue to determine copy number and to identify putative homozygous material. The R2 seed was screened by Western analysis to confirm Taqman results. The R2/F2 seed was advanced and again sampled for Taqman® to identify additional homozygous events.

Example 9

An efficacy experiment was conducted in a field to investigate the effect of YHXKA on kernel metabolism in the LH172 genotype. The gene was evaluated in selfed material and also crossed onto LH244 (since the endosperm tissue is triploid, receiving 2 polar nuclei from maternal and 1 from paternal gametes, selfed YHXKA material will have 3 doses of YHXKA in the endosperm and the crossed material will have only 1 dose of YHXKA in the endosperm).

Planting & Sampling

Positive and negative selections of 3 homozygous events (YAD 016, 055, 081) were planted (2 rows per selection). All material was hand pollinated (selfed and crossed onto LH244). Kernel samples were harvested onto dry ice at 20 days after planting (DAP) and at 45 DAP. Multiple ears per source were harvested to obtain a sample set that was representative of all crosses. YHXKA expression was checked by Western analysis to confirm expression level and to unequivocally determine the transgenic status of the seed.

Sugar & Starch Extraction

20 DAP kernels were dissected to remove the pericarp and embryo, leaving only the endosperm. The kernels were cut in half, weighed, and placed in a 96 deep well plate (termed the extraction plate). 45 DAP kernels were ground into a powder using a Cemotec 1090 Sample Mill. The powder was weighed and transferred into a 96 deep well plate (termed the extraction plate). Two steel bars and 400 µl of 80% ethanol were added to each well in the extraction plate. The extraction plates were sealed with a capmat and placed in a Harbil 5G-HD paint shaker for 2 cycles of 3 minutes. The extraction plates were incubated in a 55° C. oven for 10 minutes, inverting by hand to mix 1-2 times during incubation. The plates were centrifuged for 5 minutes at 3000 rpm. 200 µl of the supernatant was removed into a new 96 deep well plate (the assay plate) which was used to measure sucrose. 250 µl of 80% ethanol was added to the extraction plates and mixed, incubated, and centrifuged as described above. 250 µl of the supernatant was removed and added to the assay plate for sucrose analysis. An additional 150 µl of 80% ethanol was added and the extraction plateand mixing, incubation, and centrifugation was repeated. 150 µl of the supernatant was removed and added to the assay plate for sucrose analysis. The assay plate for sucrose analysis was placed in the Speed-vac overnight to remove the ethanol. The plates were stored at −80° C. until ready to assay. 200 µl of water was added when ready to conduct the assay.

The pellet left from the ethanol extractions was washed with 200 µl of 100% ethanol, placed in a Harbil 5G-HD paint shaker for 3 minutes, and centrifuged for 5 minutes at 3000 rpm. The supernatant was discarded. This ethanol-washing procedure was repeated 4 times. The resulting pellet was placed in the SpeedVac for 1.5 hours and then placed in a 65° C. oven for 2 days to dry the pellet completely. The pellet was then used for starch measurements.

Assays

Sucrose was assayed using the procedure from Bergmeyer, H. U. & Bernt, E. (1974) in *Methods of Enzymatic Analysis* (2d ed., vol.3, pp. 1176-1179, Verlag Chemie, Weinheim/Academic Press Inc., New York and London).

The dried pellet was digested as follows to determine the starch content. 250 µl of 0.2 N potassium hydroxide was added to the dried pellet, inverted to mix, and placed at 80° C. for 2 hours. 200 µl of 0.25 M sodium acetate buffer (pH 4.65) was added, inverted to mix, and lo centrifuged for 5 minutes at 3000 rpm. 5 units of amyloglucosidase (in 100 mM acetate buffer, pH 4.65) was added to each well and mixed thoroughly. The plates were incubated at 55° C. overnight. The plates were centrifuged for 10 minutes at 3000 rpm. The extract was used to assay for glucose using the protocol from Bergmeyer, H. U. & Bernt, E. (1974) in Methods of Enzymatic Analysis.

Additional Kernel Analysis

Kernels from 45 DAP elite corn hybrids were dried to a moisture content of 8.5-11% in a 37° C. oven. The material was then used to measure kernel weight, protein, oil, and density.

Iodine Staining

The kernels were cut in half and stained using Kent Lugol's solution (potassium iodide and iodine) diluted 1:10. (can be ordered from Sigma-Aldrich Co., St. Louis, Mo. catalog # L6146).

Results

In kernels of the selfed ears at 20 DAP, sucrose levels were significantly reduced, and starch levels were increased in transgene-positive plants for all three events (FIG. 8). However, at maturity (45 DAP), sucrose levels were higher in two events and starch levels were reduced in two events. Starch levels were significantly increased in the YAD8 1 transgene positives at 45 DAP compared to the isogenic negative control (YAD8 1 is a specific insertion site created by a single insertion site, and the progeny of that plant, often this is referred to as an event).

The effect of the transgene on sucrose levels of kernels resulting from the cross were similar to those of the selfed ears (FIG. 9). In kernels from the crossed ears, sucrose levels were reduced in 2 of 3 events at 20 DAP, but sucrose levels were increased in all three events at maturity. However, the effect of the transgene on starch accumulation was more positive in kernels from the crossed ears than in kernels from the selfed ears. Starch levels were higher in transgene positive plants of 2 events at 20 DAP and in 2 events at 45 DAP.

Analysis of kernel protein and oil of mature kernels from the crossed ears was conducted by NIT and NMR, respectively. Interestingly, kernels from events that had increased starch at 45 DAP (FIG. 9) also had reduced oil content (FIG. 10A). Transgene positive kernels of these same events had increased protein (FIG. 10B).

To determine whether the difference in starch accumulation corresponded with differences in starch distribution, mature kernels were stained with iodine. In all three events, we observed that the iodine-resistant "hard" endosperm was reduced in kernels that contain the YHXKA transgene compared to transgene-negative controls (FIG. 12).

Density was measured for mature kernels of crossed ears, and was found to be reduced for all three events (FIG. 11). The decrease ranged from 4.3% to 4.9%. Seed weight was reduced for Event YAD16, but was unchanged for the other two events (FIG. 11). Note small sample size for seed weight data. The corn kernel densities were measured using Micromeritics AccuPyc 1130 Pycnometer. The AccuPyc works by measuring the amount of displaced gas. The pressures observed upon filling the sample chamber and then discharging it into a second empty chamber allow computation of the sample solid phase volume. Gas molecules rapidly fill the tiniest pores of the sample; only the truly solid phase of the sample displaces the gas.

Discussion

The results indicate that endosperm-targeted expression of the YHXKA transgene can result in an increase in starch in corn kernels at maturity (FIGS. 8 and 9). An increase in starch was observed in mature kernels of two events from crossed ears and in one event from selfed ears. The fact that starch was more consistently increased in kernels from the crossed ears could be due to an effect of dosage of the transgene (although other mechanisms are possible), since kernels of the selfed ears would have 3 doses of the transgene, while kernels of the crosses would have only one dose. This mechanism could also explain the differences in events in the selfed ears, if YAD81 has lower enzyme activity than the other events. Alternatively, the difference in results from selfed and crossed ears could be due to differences in the genetic backgrounds (although other mechanisms are possible). The selfs would be homozygous for LH172 alleles at all loci, while the crosses were heterozygous for all LH172 and LH244 at all alleles. The difference in kernel quality due to the different genetic background of the selfs and crosses was readily observed by kernel size.

The increase in kernel starch was accompanied by a small increase in kernel protein, and a decrease in kernel oil (FIG. 10). These composition changes resulted in an approximately 5% decrease in density of the kernel.

Fermentation Assay

The Fermentation method uses High Performance Liquid Chromatography (HPLC) with refractive index detection (RID) to separate and quantify ethanol. The fermentation requires a two step process. The first step is the liquefaction of the starch to soluble dextrins by adding water and alpha amylase to the 25.0 g flour sample and placing in an 85° C. water bath. The second step is the simultaneous hydrolysis of the dextrins and the fermentation of glucose using additional enzymes and yeast. The relative standard deviation for this method is ~2%.

Protein Assays

First pass protein analysis was conducted by NIT. To confirm the results, a sub-set of the events in one tester (Events 2, 21, 32, 82 in the LH244×LH172) were analyzed using Elemental Analysis from Leico which uses combustion GC analysis.

Oil Assays

First pass oil analysis was conducted by NIT. To confirm the results, a sub-set of the events from one tester (Events 2, 21, 32, 82 in the LH244×LH172) were analyzed by bulk NMR.

Results

Sucrose & Starch

There were no overall differences in sucrose in mature kernels when comparing positive to negative in either tester (data not shown). The measurement of total starch did reveal differences (FIG. 12). In the HC33 tester, one event (86) had a significant increase in total starch (FIG. 12A). Another event (13) had a trend towards an increase in starch, but the difference was not quite statistically significant. In the LH244 tester, 4 events (2, 13, 81, and 86) had a significant increase in total starch (FIG. 12B). One event (21) had a significant decrease in starch. When the starch values from all the events were averaged across each tester, there was a 9.8% increase in LH244 tester when comparing transgene negative and positive seeds (FIG. 12C). There was no statistical difference in the HC33 tester (FIG. 12C).

Fermentation

Fermentation results are shown in FIG. 13 for 48 and 54 hours. Results are given in % ethanol yield on a moisture corrected basis. Standard calibration curve(s) were used. Three events (2, 13, 86) had a statistically significant increase (2-3%) in ethanol at both 48 and 54 hours in the HC33× LH172 background. One event (86) had an increase in ethanol at both timepoints in the LH244×LH172 background.

Protein Results

Protein results from NIT and Leico methods are shown in FIG. 14. All events tested by NIT showed an increase in protein (~15%) when comparing the positive to its negative isoline. Four events were chosen for confirmation of protein content using the Leico method. 3 events out of the 4 tested by Leico showed an increase in protein (10-13%).

Oil Results

Oil results from NIT and bulk NMR are shown in FIG. 15. All events tested by NIT showed an increase in oil (~10%) when comparing positive to its negative isoline. Four events were chosen for confirmation by NMR. 2 events out of the 4 showed an increase in oil by bulk NMR (10-14%). These two methods produced different values for the percent oil. These differences are due to the different calibrations used for the two methods.

These data indicate that endosperm-targeted expression of YHXKA results in composition changes in mature kernels. Kernels from hybrid material were used in which ¼ of the kernels would be negative for the transgene and the other ¾ of the kernels would have different doses of HXK. One advantage to using this material is that it gives a clear picture of how the transgene behaves in true field conditions in the hybrid setting. The experiment showed that total starch was increased in mature kernels, specifically in the LH172× LH244 hybrid. Several events also had an increase in ethanol produced by fermentation of kernel extracts. These increases may be due to an increase in the amount of extractable starch, so that more starch was available for the assay.

What is claimed is:

1. A corn plant containing in its genome a recombinant DNA molecule comprising, in the 5' to 3' direction, a promoter providing expression in a plant seed operably linked to DNA encoding a fungal hexokinase.

2. A seed from a corn plant of claim 1 wherein said seed has in its genome a recombinant DNA molecule comprising, in the 5' to 3' direction, a promoter providing expression in a plant seed operably linked to DNA encoding a fungal hexokinase.

* * * * *

SEQUENCE LISTING

```
<160> NUMBER OF SEQ ID NOS: 34

<210> SEQ ID NO 1
<211> LENGTH: 1458
<212> TYPE: DNA
<213> ORGANISM: Saccharomyces cerevisiae
<220> FEATURE:
<221> NAME/KEY: CDS
<222> LOCATION: (1)..(1458)

<400> SEQUENCE: 1 atg gtt cat tta ggt cca aag aaa cca cag gct aga aag ggt tcc atg      48
Met Val His Leu Gly Pro Lys Lys Pro Gln Ala Arg Lys Gly Ser Met
1               5                   10                  15 gct gat gtg ccc aag gaa ttg atg gat gaa att cat cag ttg gaa gat      96
Ala Asp Val Pro Lys Glu Leu Met Asp Glu Ile His Gln Leu Glu Asp
                20                  25                  30 atg ttt aca gtt gac agc gag acc ttg aga aag gtt gtt aag cac ttt     144
Met Phe Thr Val Asp Ser Glu Thr Leu Arg Lys Val Val Lys His Phe
            35                  40                  45 atc gac gaa ttg aat aaa ggt ttg aca aag aag gga ggt aac att cca     192
Ile Asp Glu Leu Asn Lys Gly Leu Thr Lys Lys Gly Gly Asn Ile Pro
        50                  55                  60 atg att ccc ggt tgg gtc atg gaa ttc cca aca ggt aaa gaa tct ggt     240
Met Ile Pro Gly Trp Val Met Glu Phe Pro Thr Gly Lys Glu Ser Gly
65                  70                  75                  80 aac tat ttg gcc att gat ttg ggt ggt act aac tta aga gtc gtg ttg     288
Asn Tyr Leu Ala Ile Asp Leu Gly Gly Thr Asn Leu Arg Val Val Leu
                85                  90                  95 gtc aag ttg agc ggt aac cat acc ttt gac acc act caa tcc aag tat     336
```

```
                  Val Lys Leu Ser Gly Asn His Thr Phe Asp Thr Thr Gln Ser Lys Tyr
                                  100                 105                 110 aaa cta cca cat gac atg aga acc act aag cac caa gag gag tta tgg           384
Lys Leu Pro His Asp Met Arg Thr Thr Lys His Gln Glu Glu Leu Trp
            115                 120                 125 tcc ttt att gcc gac tct ttg aag gac ttt atg gtc gag caa gaa ttg           432
Ser Phe Ile Ala Asp Ser Leu Lys Asp Phe Met Val Glu Gln Glu Leu
        130                 135                 140 cta aac acc aag gac acc tta cca tta ggt ttc acc ttc tcg tac cca           480
Leu Asn Thr Lys Asp Thr Leu Pro Leu Gly Phe Thr Phe Ser Tyr Pro
145                 150                 155                 160 gct tcc caa aac aag att aac gaa ggt att ttg caa aga tgg acc aag           528
Ala Ser Gln Asn Lys Ile Asn Glu Gly Ile Leu Gln Arg Trp Thr Lys
                165                 170                 175 ggt ttc gat att cca aat gtc gaa ggc cac gat gtc gtc cca ttg cta           576
Gly Phe Asp Ile Pro Asn Val Glu Gly His Asp Val Val Pro Leu Leu
            180                 185                 190 caa aac gaa att tcc aag aga gag ttg cct att gaa att gta gca ttg           624
Gln Asn Glu Ile Ser Lys Arg Glu Leu Pro Ile Glu Ile Val Ala Leu
        195                 200                 205 att aat gat act gtc ggt act tta gtt gcc tca tac tac act gac cca           672
Ile Asn Asp Thr Val Gly Thr Leu Val Ala Ser Tyr Tyr Thr Asp Pro
210                 215                 220 gag act aag atg ggt gtg att ttc ggt act ggt gtc aac ggt gct ttc           720
Glu Thr Lys Met Gly Val Ile Phe Gly Thr Gly Val Asn Gly Ala Phe
225                 230                 235                 240 tat gat gtt gtt tcc gat atc gaa aag ttg gag ggc aaa tta gca gac           768
Tyr Asp Val Val Ser Asp Ile Glu Lys Leu Glu Gly Lys Leu Ala Asp
                245                 250                 255 gat att cca agt aac tct cca atg gct atc aat tgt gaa tat ggt tcc           816
Asp Ile Pro Ser Asn Ser Pro Met Ala Ile Asn Cys Glu Tyr Gly Ser
            260                 265                 270 ttc gat aat gaa cat ttg gtc ttg cca aga acc aag tac gat gtt gct           864
Phe Asp Asn Glu His Leu Val Leu Pro Arg Thr Lys Tyr Asp Val Ala
        275                 280                 285 gtc gac gaa caa tct cca aga cct ggt caa caa gct ttt gaa aag atg           912
Val Asp Glu Gln Ser Pro Arg Pro Gly Gln Gln Ala Phe Glu Lys Met
290                 295                 300 acc tcc ggt tac tac ttg ggt gaa ttg ttg cgt cta gtg tta ctt gaa           960
Thr Ser Gly Tyr Tyr Leu Gly Glu Leu Leu Arg Leu Val Leu Leu Glu
305                 310                 315                 320 tta aac gag aag ggc ttg atg ttg aag gat caa gat cta agc aag ttg          1008
Leu Asn Glu Lys Gly Leu Met Leu Lys Asp Gln Asp Leu Ser Lys Leu
                325                 330                 335 aaa caa cca tac atc atg gat acc tcc tac cca gca aga atc gag gat          1056
Lys Gln Pro Tyr Ile Met Asp Thr Ser Tyr Pro Ala Arg Ile Glu Asp
            340                 345                 350 gat cca ttt gaa aac ttg gaa gat act gat gac atc ttc caa aag gac          1104
Asp Pro Phe Glu Asn Leu Glu Asp Thr Asp Asp Ile Phe Gln Lys Asp
        355                 360                 365 ttt ggt gtc aag acc act ctg cca gaa cgt aag ttg att aga aga ctt          1152
Phe Gly Val Lys Thr Thr Leu Pro Glu Arg Lys Leu Ile Arg Arg Leu
370                 375                 380 tgt gaa ttg atc ggt acc aga gct gct aga tta gct gtt tgt ggt att          1200
Cys Glu Leu Ile Gly Thr Arg Ala Ala Arg Leu Ala Val Cys Gly Ile
385                 390                 395                 400 gcc gct att tgc caa aag aga ggt tac aag act ggt cac att gcc gct          1248
Ala Ala Ile Cys Gln Lys Arg Gly Tyr Lys Thr Gly His Ile Ala Ala
                405                 410                 415
```

```
gac ggt tct gtc tat aac aaa tac cca ggt ttc aag gaa gcc gcc gct    1296
Asp Gly Ser Val Tyr Asn Lys Tyr Pro Gly Phe Lys Glu Ala Ala Ala
            420                 425                 430 aag ggt ttg aga gat atc tat gga tgg act ggt ggc gca agc aac gat    1344
Lys Gly Leu Arg Asp Ile Tyr Gly Trp Thr Gly Gly Ala Ser Asn Asp
435                 440                 445 cca att acg att gtt cca gct gag gat ggt tcc ggt gca ggt gct gct    1392
Pro Ile Thr Ile Val Pro Ala Glu Asp Gly Ser Gly Ala Gly Ala Ala
    450                 455                 460 gtt att gct gca ttg tcc gaa aaa aga att gcc gaa ggt aag tct ctt    1440
Val Ile Ala Ala Leu Ser Glu Lys Arg Ile Ala Glu Gly Lys Ser Leu
465                 470                 475                 480 ggt atc att ggc gct taa                                            1458
Gly Ile Ile Gly Ala
                485

<210> SEQ ID NO 2
<211> LENGTH: 485
<212> TYPE: PRT
<213> ORGANISM: Saccharomyces cerevisiae

<400> SEQUENCE: 2

Met Val His Leu Gly Pro Lys Lys Pro Gln Ala Arg Lys Gly Ser Met
1               5                   10                  15

Ala Asp Val Pro Lys Glu Leu Met Asp Glu Ile His Gln Leu Glu Asp
            20                  25                  30

Met Phe Thr Val Asp Ser Glu Thr Leu Arg Lys Val Val Lys His Phe
        35                  40                  45

Ile Asp Glu Leu Asn Lys Gly Leu Thr Lys Lys Gly Gly Asn Ile Pro
    50                  55                  60

Met Ile Pro Gly Trp Val Met Glu Phe Pro Thr Gly Lys Glu Ser Gly
65                  70                  75                  80

Asn Tyr Leu Ala Ile Asp Leu Gly Gly Thr Asn Leu Arg Val Val Leu
                85                  90                  95

Val Lys Leu Ser Gly Asn His Thr Phe Asp Thr Thr Gln Ser Lys Tyr
            100                 105                 110

Lys Leu Pro His Asp Met Arg Thr Thr Lys His Gln Glu Glu Leu Trp
        115                 120                 125

Ser Phe Ile Ala Asp Ser Leu Lys Asp Phe Met Val Glu Gln Glu Leu
    130                 135                 140

Leu Asn Thr Lys Asp Thr Leu Pro Leu Gly Phe Thr Phe Ser Tyr Pro
145                 150                 155                 160

Ala Ser Gln Asn Lys Ile Asn Glu Gly Ile Leu Gln Arg Trp Thr Lys
                165                 170                 175

Gly Phe Asp Ile Pro Asn Val Glu Gly His Asp Val Val Pro Leu Leu
            180                 185                 190

Gln Asn Glu Ile Ser Lys Arg Glu Leu Pro Ile Glu Ile Val Ala Leu
        195                 200                 205

Ile Asn Asp Thr Val Gly Thr Leu Val Ala Ser Tyr Tyr Thr Asp Pro
    210                 215                 220

Glu Thr Lys Met Gly Val Ile Phe Gly Thr Gly Val Asn Gly Ala Phe
225                 230                 235                 240

Tyr Asp Val Val Ser Asp Ile Glu Lys Leu Glu Gly Lys Leu Ala Asp
                245                 250                 255

Asp Ile Pro Ser Asn Ser Pro Met Ala Ile Asn Cys Glu Tyr Gly Ser
            260                 265                 270
```

-continued

```
Phe Asp Asn Glu His Leu Val Leu Pro Arg Thr Lys Tyr Asp Val Ala
        275                 280                 285

Val Asp Glu Gln Ser Pro Arg Pro Gly Gln Gln Ala Phe Glu Lys Met
    290                 295                 300

Thr Ser Gly Tyr Tyr Leu Gly Glu Leu Arg Leu Val Leu Leu Glu
305                 310                 315                 320

Leu Asn Glu Lys Gly Leu Met Leu Lys Asp Gln Asp Leu Ser Lys Leu
                325                 330                 335

Lys Gln Pro Tyr Ile Met Asp Thr Ser Tyr Pro Ala Arg Ile Glu Asp
            340                 345                 350

Asp Pro Phe Glu Asn Leu Glu Asp Thr Asp Ile Phe Gln Lys Asp
        355                 360                 365

Phe Gly Val Lys Thr Thr Leu Pro Glu Arg Lys Leu Ile Arg Arg Leu
    370                 375                 380

Cys Glu Leu Ile Gly Thr Arg Ala Ala Arg Leu Ala Val Cys Gly Ile
385                 390                 395                 400

Ala Ala Ile Cys Gln Lys Arg Gly Tyr Lys Thr Gly His Ile Ala Ala
                405                 410                 415

Asp Gly Ser Val Tyr Asn Lys Tyr Pro Gly Phe Lys Glu Ala Ala Ala
            420                 425                 430

Lys Gly Leu Arg Asp Ile Tyr Gly Trp Thr Gly Gly Ala Ser Asn Asp
        435                 440                 445

Pro Ile Thr Ile Val Pro Ala Glu Asp Gly Ser Gly Ala Gly Ala Ala
    450                 455                 460

Val Ile Ala Ala Leu Ser Glu Lys Arg Ile Ala Glu Gly Lys Ser Leu
465                 470                 475                 480

Gly Ile Ile Gly Ala
                485

<210> SEQ ID NO 3
<211> LENGTH: 24
<212> TYPE: DNA
<213> ORGANISM: Artificial Sequence
<220> FEATURE:
<223> OTHER INFORMATION: Yeast hexokinase sequence with 5' artificial
      addition
<220> FEATURE:
<221> NAME/KEY: Artificial
<222> LOCATION: (1)..(9)
<223> OTHER INFORMATION: ATA plus BamHI restriction site

<400> SEQUENCE: 3
ataggatcca tggttcattt aggt                                          24

<210> SEQ ID NO 4
<211> LENGTH: 24
<212> TYPE: DNA
<213> ORGANISM: Artificial sequence
<220> FEATURE:
<223> OTHER INFORMATION: Yeast hexokinase with 3' artificial addition
<220> FEATURE:
<221> NAME/KEY: Artificial_5' addititon with XhoI restriction site
<222> LOCATION: (1)..(9)
<223> OTHER INFORMATION: AAA plus XhoI restriction site

<400> SEQUENCE: 4
aaactcgagt taagcgccaa tgat                                          24

<210> SEQ ID NO 5
<211> LENGTH: 1437
<212> TYPE: DNA
```

<213> ORGANISM: Debaryomyces occidentalis
<220> FEATURE:
<221> NAME/KEY: CDS
<222> LOCATION: (1)..(1437)

<400> SEQUENCE: 5

```
atg gtt cac tta ggt cca aaa cct cca caa cat aga aaa gga tcc ttc       48
Met Val His Leu Gly Pro Lys Pro Pro Gln His Arg Lys Gly Ser Phe
1               5                   10                  15 ttg gat gtt cct gaa tat ttg ttg aag gaa ttg aca gaa ctc gaa gga       96
Leu Asp Val Pro Glu Tyr Leu Leu Lys Glu Leu Thr Glu Leu Glu Gly
            20                  25                  30 tta tta aca gtt tca ggt gaa aca tta agg aag att act gat cac ttt      144
Leu Leu Thr Val Ser Gly Glu Thr Leu Arg Lys Ile Thr Asp His Phe
        35                  40                  45 att tca gaa ttg gaa aaa ggt tta tct aaa caa ggg gga aat att cct      192
Ile Ser Glu Leu Glu Lys Gly Leu Ser Lys Gln Gly Gly Asn Ile Pro
    50                  55                  60 atg att cca gga tgg gtt atg gac ttc cca aca gga aaa gaa atg ggt      240
Met Ile Pro Gly Trp Val Met Asp Phe Pro Thr Gly Lys Glu Met Gly
65                  70                  75                  80 gat tac ttg gct att gat tta ggt ggt act aat ttg aga gtt gtt tta      288
Asp Tyr Leu Ala Ile Asp Leu Gly Gly Thr Asn Leu Arg Val Val Leu
                85                  90                  95 gtt aag tta ggt ggt aac agg gac ttt gac act act caa tcc aag ttc      336
Val Lys Leu Gly Gly Asn Arg Asp Phe Asp Thr Thr Gln Ser Lys Phe
            100                 105                 110 gca ttg cca gaa aac atg aga act gcc aag tct gaa gag tta tgg gaa      384
Ala Leu Pro Glu Asn Met Arg Thr Ala Lys Ser Glu Glu Leu Trp Glu
        115                 120                 125 ttt att gct gag tgt tta caa aag ttc gtg gaa gaa gaa ttt cga aat      432
Phe Ile Ala Glu Cys Leu Gln Lys Phe Val Glu Glu Glu Phe Arg Asn
    130                 135                 140 ggt gtt ctg tca aat tta cca tta ggt ttc acc ttt tca tac cca gca      480
Gly Val Leu Ser Asn Leu Pro Leu Gly Phe Thr Phe Ser Tyr Pro Ala
145                 150                 155                 160 tct caa ggt tct atc aat gaa ggg tat ttg caa aga tgg acc aaa ggt      528
Ser Gln Gly Ser Ile Asn Glu Gly Tyr Leu Gln Arg Trp Thr Lys Gly
                165                 170                 175 ttc gac att gaa ggt gtt gag gga cac gat gtt gtt cca atg tta caa      576
Phe Asp Ile Glu Gly Val Glu Gly His Asp Val Val Pro Met Leu Gln
            180                 185                 190 gct gca att gaa aaa cgt aag gtt cca att gaa gtt gtt gcg tta atc      624
Ala Ala Ile Glu Lys Arg Lys Val Pro Ile Glu Val Val Ala Leu Ile
        195                 200                 205 aat gac acc aca ggt act tta gtt gct tct atg tac acc gat cca gaa      672
Asn Asp Thr Thr Gly Thr Leu Val Ala Ser Met Tyr Thr Asp Pro Glu
    210                 215                 220 gct aaa atg ggt tta ttt tcc ggt act ggt tgt aat ggt gct tac tac      720
Ala Lys Met Gly Leu Phe Ser Gly Thr Gly Cys Asn Gly Ala Tyr Tyr
225                 230                 235                 240 gat gtt gtc gat aac att cca aaa tta gaa gga aag gtt cca gat gac      768
Asp Val Val Asp Asn Ile Pro Lys Leu Glu Gly Lys Val Pro Asp Asp
                245                 250                 255 att aaa agc tct tcc cca atg gcc atc aac tgt gaa tac ggt gct ttc      816
Ile Lys Ser Ser Ser Pro Met Ala Ile Asn Cys Glu Tyr Gly Ala Phe
            260                 265                 270 gat aat gag cat atc att ttg cct aga act aaa tac gat atc caa atc      864
Asp Asn Glu His Ile Ile Leu Pro Arg Thr Lys Tyr Asp Ile Gln Ile
        275                 280                 285
```

-continued

```
gat gaa gaa tca cca aga cca gga caa cag gct ttc gaa aag atg atc    912
Asp Glu Glu Ser Pro Arg Pro Gly Gln Gln Ala Phe Glu Lys Met Ile
    290             295                 300 tct ggt tac tac tta ggt gaa gtt tta aga ttg att tta ctt gat tta    960
Ser Gly Tyr Tyr Leu Gly Glu Val Leu Arg Leu Ile Leu Leu Asp Leu
305                 310                 315                 320 acc tct aaa caa tta att ttc aaa gac caa gat ttg tct aaa tta caa   1008
Thr Ser Lys Gln Leu Ile Phe Lys Asp Gln Asp Leu Ser Lys Leu Gln
                325                 330                 335 gtt cca ttc att tta gat acc tca atc cca gct aga att gaa gaa gat   1056
Val Pro Phe Ile Leu Asp Thr Ser Ile Pro Ala Arg Ile Glu Glu Asp
            340                 345                 350 ccg ttt gaa aac tta tct gat gtc caa gaa tta ttt caa gaa att tta   1104
Pro Phe Glu Asn Leu Ser Asp Val Gln Glu Leu Phe Gln Glu Ile Leu
        355                 360                 365 ggt att caa act act tct cca gaa aga aaa atc atc cgt cgt cta gcg   1152
Gly Ile Gln Thr Thr Ser Pro Glu Arg Lys Ile Ile Arg Arg Leu Ala
370                 375                 380 gaa ttg atc ggt gaa aga tca gcc aga tta tca att tgt ggt att gct   1200
Glu Leu Ile Gly Glu Arg Ser Ala Arg Leu Ser Ile Cys Gly Ile Ala
385                 390                 395                 400 gct att tgc aag aag aga ggc tac aaa acc gct cat tgt gcc gct gat   1248
Ala Ile Cys Lys Lys Arg Gly Tyr Lys Thr Ala His Cys Ala Ala Asp
                405                 410                 415 ggt tca gtc tac aac aaa tac cca ggt ttc aaa gaa aga gct gct aaa   1296
Gly Ser Val Tyr Asn Lys Tyr Pro Gly Phe Lys Glu Arg Ala Ala Lys
            420                 425                 430 ggt ttg aga gat atc ttt caa tgg gaa tct gaa gaa gat cca att gtc   1344
Gly Leu Arg Asp Ile Phe Gln Trp Glu Ser Glu Glu Asp Pro Ile Val
        435                 440                 445 att gtg cct gca gaa gat ggt tta ggt gca ggt gcc gct atc att gct   1392
Ile Val Pro Ala Glu Asp Gly Leu Gly Ala Gly Ala Ala Ile Ile Ala
    450                 455                 460 gca ttg act gaa aaa aga tta aag gat gga tta ccg ttg gta tga       1437
Ala Leu Thr Glu Lys Arg Leu Lys Asp Gly Leu Pro Leu Val
465                 470                 475
```

<210> SEQ ID NO 6
<211> LENGTH: 478
<212> TYPE: PRT
<213> ORGANISM: Debaryomyces occidentalis

<400> SEQUENCE: 6

```
Met Val His Leu Gly Pro Lys Pro Gln His Arg Lys Gly Ser Phe
1               5                   10                  15

Leu Asp Val Pro Glu Tyr Leu Leu Lys Glu Leu Thr Glu Leu Glu Gly
                20                  25                  30

Leu Leu Thr Val Ser Gly Glu Thr Leu Arg Lys Ile Thr Asp His Phe
            35                  40                  45

Ile Ser Glu Leu Glu Lys Gly Leu Ser Lys Gln Gly Gly Asn Ile Pro
        50                  55                  60

Met Ile Pro Gly Trp Val Met Asp Phe Pro Thr Gly Lys Glu Met Gly
65                  70                  75                  80

Asp Tyr Leu Ala Ile Asp Leu Gly Gly Thr Asn Leu Arg Val Val Leu
                85                  90                  95

Val Lys Leu Gly Gly Asn Arg Asp Phe Asp Thr Thr Gln Ser Lys Phe
            100                 105                 110

Ala Leu Pro Glu Asn Met Arg Thr Ala Lys Ser Glu Glu Leu Trp Glu
        115                 120                 125
```

```
Phe Ile Ala Glu Cys Leu Gln Lys Phe Val Glu Glu Phe Arg Asn
        130                 135                 140
Gly Val Leu Ser Asn Leu Pro Leu Gly Phe Thr Phe Ser Tyr Pro Ala
145                 150                 155                 160
Ser Gln Gly Ser Ile Asn Glu Gly Tyr Leu Gln Arg Trp Thr Lys Gly
                165                 170                 175
Phe Asp Ile Glu Gly Val Glu Gly His Asp Val Val Pro Met Leu Gln
            180                 185                 190
Ala Ala Ile Glu Lys Arg Lys Val Pro Ile Glu Val Ala Leu Ile
        195                 200                 205
Asn Asp Thr Thr Gly Thr Leu Val Ala Ser Met Tyr Thr Asp Pro Glu
210                 215                 220
Ala Lys Met Gly Leu Phe Ser Gly Thr Gly Cys Asn Gly Ala Tyr Tyr
225                 230                 235                 240
Asp Val Val Asp Asn Ile Pro Lys Leu Glu Gly Lys Val Pro Asp Asp
                245                 250                 255
Ile Lys Ser Ser Ser Pro Met Ala Ile Asn Cys Glu Tyr Gly Ala Phe
                260                 265                 270
Asp Asn Glu His Ile Ile Leu Pro Arg Thr Lys Tyr Asp Ile Gln Ile
            275                 280                 285
Asp Glu Glu Ser Pro Arg Pro Gly Gln Gln Ala Phe Glu Lys Met Ile
        290                 295                 300
Ser Gly Tyr Tyr Leu Gly Glu Val Leu Arg Leu Ile Leu Leu Asp Leu
305                 310                 315                 320
Thr Ser Lys Gln Leu Ile Phe Lys Asp Gln Asp Leu Ser Lys Leu Gln
                325                 330                 335
Val Pro Phe Ile Leu Asp Thr Ser Ile Pro Ala Arg Ile Glu Glu Asp
                340                 345                 350
Pro Phe Glu Asn Leu Ser Asp Val Gln Glu Leu Phe Gln Glu Ile Leu
        355                 360                 365
Gly Ile Gln Thr Thr Ser Pro Glu Arg Lys Ile Ile Arg Arg Leu Ala
370                 375                 380
Glu Leu Ile Gly Glu Arg Ser Ala Arg Leu Ser Ile Cys Gly Ile Ala
385                 390                 395                 400
Ala Ile Cys Lys Lys Arg Gly Tyr Lys Thr Ala His Cys Ala Ala Asp
                405                 410                 415
Gly Ser Val Tyr Asn Lys Tyr Pro Gly Phe Lys Glu Arg Ala Ala Lys
            420                 425                 430
Gly Leu Arg Asp Ile Phe Gln Trp Glu Ser Glu Glu Asp Pro Ile Val
        435                 440                 445
Ile Val Pro Ala Glu Asp Gly Leu Gly Ala Gly Ala Ala Ile Ile Ala
    450                 455                 460
Ala Leu Thr Glu Lys Arg Leu Lys Asp Gly Leu Pro Leu Val
465                 470                 475

<210> SEQ ID NO 7
<211> LENGTH: 1458
<212> TYPE: DNA
<213> ORGANISM: Kluyveromyces lactis
<220> FEATURE:
<221> NAME/KEY: CDS
<222> LOCATION: (1)..(1458)

<400> SEQUENCE: 7 atg gtt cgt tta ggt cca aag aag cct cca gcc aga aag ggg tcc atg         48
```

```
Met Val Arg Leu Gly Pro Lys Lys Pro Ala Arg Lys Gly Ser Met
1               5                   10                  15 gca gat gtg cca gct aat ttg atg gaa caa atc cac ggt ttg gaa act    96
Ala Asp Val Pro Ala Asn Leu Met Glu Gln Ile His Gly Leu Glu Thr
                20                  25                  30 ttg ttc acc gtc tct tca gaa aaa atg aga agc att gtc aag cat ttc    144
Leu Phe Thr Val Ser Ser Glu Lys Met Arg Ser Ile Val Lys His Phe
            35                  40                  45 atc agt gaa ttg gac aaa ggt ttg tcc aaa aag ggt ggt aac att cct    192
Ile Ser Glu Leu Asp Lys Gly Leu Ser Lys Lys Gly Gly Asn Ile Pro
        50                  55                  60 atg att cca ggt tgg gtt gtt gag tat cca act ggt aag gaa act ggt    240
Met Ile Pro Gly Trp Val Val Glu Tyr Pro Thr Gly Lys Glu Thr Gly
65                  70                  75                  80 gat ttc tta gct ctt gat ttg ggt ggt acc aac ttg aga gtt gtg ttg    288
Asp Phe Leu Ala Leu Asp Leu Gly Gly Thr Asn Leu Arg Val Val Leu
                85                  90                  95 gtt aaa ttg ggt ggt aat cat gat ttc gac acc act caa aac aag tac    336
Val Lys Leu Gly Gly Asn His Asp Phe Asp Thr Thr Gln Asn Lys Tyr
            100                 105                 110 aga tta cca gac cat ttg aga act ggt act tct gaa caa ttg tgg tca    384
Arg Leu Pro Asp His Leu Arg Thr Gly Thr Ser Glu Gln Leu Trp Ser
        115                 120                 125 ttt att gca aag tgt ttg aag gaa ttc gtc gat gaa tgg tac cca gat    432
Phe Ile Ala Lys Cys Leu Lys Glu Phe Val Asp Glu Trp Tyr Pro Asp
130                 135                 140 ggt gtt tct gaa cca ttg cca ttg ggt ttc act ttc tca tac cct gca    480
Gly Val Ser Glu Pro Leu Pro Leu Gly Phe Thr Phe Ser Tyr Pro Ala
145                 150                 155                 160 tct caa aag aag atc aat tcc ggt gtg ttg caa cgt tgg acc aag ggt    528
Ser Gln Lys Lys Ile Asn Ser Gly Val Leu Gln Arg Trp Thr Lys Gly
                165                 170                 175 ttc gat att gaa ggt gtt gaa ggt cac gat gtt gtt cca atg cta caa    576
Phe Asp Ile Glu Gly Val Glu Gly His Asp Val Val Pro Met Leu Gln
            180                 185                 190 gaa cag att gaa aag ctg aat atc cca atc aat gtc gtt cga ttg atc    624
Glu Gln Ile Glu Lys Leu Asn Ile Pro Ile Asn Val Val Arg Leu Ile
        195                 200                 205 aac gat acc act ggt acc ttg gtt gcc tct ttg tac act gat cct caa    672
Asn Asp Thr Thr Gly Thr Leu Val Ala Ser Leu Tyr Thr Asp Pro Gln
210                 215                 220 act aag atg ggt atc att atc ggt act ggt gtc aac ggt gct tac tac    720
Thr Lys Met Gly Ile Ile Ile Gly Thr Gly Val Asn Gly Ala Tyr Tyr
225                 230                 235                 240 gat gtt gtt tct ggt att gag aaa ttg gaa ggt ttg ttg cca gaa gat    768
Asp Val Val Ser Gly Ile Glu Lys Leu Glu Gly Leu Leu Pro Glu Asp
                245                 250                 255 atc ggt cca gat tct cca atg gca atc aac tgt gaa tat ggt tcc ttc    816
Ile Gly Pro Asp Ser Pro Met Ala Ile Asn Cys Glu Tyr Gly Ser Phe
            260                 265                 270 gat aac gaa cat ttg gtg ttg cca aga acc aaa tac gat gtt ata atc    864
Asp Asn Glu His Leu Val Leu Pro Arg Thr Lys Tyr Asp Val Ile Ile
        275                 280                 285 gat gaa gaa tct cca aga cca ggt caa caa gct ttc gaa aag atg act    912
Asp Glu Glu Ser Pro Arg Pro Gly Gln Gln Ala Phe Glu Lys Met Thr
290                 295                 300 tct ggt tac tat cta ggt gaa atc atg cgt cta gta cta ttg gac ttg    960
Ser Gly Tyr Tyr Leu Gly Glu Ile Met Arg Leu Val Leu Leu Asp Leu
305                 310                 315                 320
```

```
tac gac agt ggt ttc atc ttt aag gac caa gat atc tcc aag ttg aaa      1008
Tyr Asp Ser Gly Phe Ile Phe Lys Asp Gln Asp Ile Ser Lys Leu Lys
            325                 330                 335 gag gct tac gtc atg gac acc agt tat cca tct aag atc gaa gat gat      1056
Glu Ala Tyr Val Met Asp Thr Ser Tyr Pro Ser Lys Ile Glu Asp Asp
            340                 345                 350 cca ttc gaa aac ttg gaa gac act gac gat ctg ttc aag act aac ttg      1104
Pro Phe Glu Asn Leu Glu Asp Thr Asp Asp Leu Phe Lys Thr Asn Leu
            355                 360                 365 aac atc gaa act acc gtt gtt gag aga aag ttg att aga aaa tta gcc      1152
Asn Ile Glu Thr Thr Val Val Glu Arg Lys Leu Ile Arg Lys Leu Ala
370                 375                 380 gaa ttg gtc gga aca aga gct gca aga ttg act gtt tgt ggt gtt tct      1200
Glu Leu Val Gly Thr Arg Ala Ala Arg Leu Thr Val Cys Gly Val Ser
385                 390                 395                 400 gct atc tgt gac aag aga ggc tac aag act gct cac att gca gct gat      1248
Ala Ile Cys Asp Lys Arg Gly Tyr Lys Thr Ala His Ile Ala Ala Asp
            405                 410                 415 ggt tct gtc ttc aac aga tac cca ggt tac aag gaa aag gcc gct caa      1296
Gly Ser Val Phe Asn Arg Tyr Pro Gly Tyr Lys Glu Lys Ala Ala Gln
            420                 425                 430 gcc ttg aag gat atc tac aac tgg gat gtc gaa aag atg gaa gac cac      1344
Ala Leu Lys Asp Ile Tyr Asn Trp Asp Val Glu Lys Met Glu Asp His
            435                 440                 445 cca atc caa ttg gtg gct gct gaa gat ggt tcc ggt gtt ggt gct gct      1392
Pro Ile Gln Leu Val Ala Ala Glu Asp Gly Ser Gly Val Gly Ala Ala
450                 455                 460 atc att gct tgt ttg act caa aag aga ttg gct gcc ggt aag tct gtt      1440
Ile Ile Ala Cys Leu Thr Gln Lys Arg Leu Ala Ala Gly Lys Ser Val
465                 470                 475                 480 ggt att aaa ggc gaa tag                                              1458
Gly Ile Lys Gly Glu
            485
```

<210> SEQ ID NO 8
<211> LENGTH: 485
<212> TYPE: PRT
<213> ORGANISM: Kluyveromyces lactis

<400> SEQUENCE: 8

Met Val Arg Leu Gly Pro Lys Lys Pro Ala Arg Lys Gly Ser Met
1               5                   10                  15

Ala Asp Val Pro Ala Asn Leu Met Glu Gln Ile His Gly Leu Glu Thr
                20                  25                  30

Leu Phe Thr Val Ser Ser Glu Lys Met Arg Ser Ile Val Lys His Phe
            35                  40                  45

Ile Ser Glu Leu Asp Lys Gly Leu Ser Lys Lys Gly Gly Asn Ile Pro
50                  55                  60

Met Ile Pro Gly Trp Val Val Glu Tyr Pro Thr Gly Lys Glu Thr Gly
65                  70                  75                  80

Asp Phe Leu Ala Leu Asp Leu Gly Gly Thr Asn Leu Arg Val Val Leu
                85                  90                  95

Val Lys Leu Gly Gly Asn His Asp Phe Asp Thr Thr Gln Asn Lys Tyr
            100                 105                 110

Arg Leu Pro Asp His Leu Arg Thr Gly Thr Ser Glu Gln Leu Trp Ser
        115                 120                 125

Phe Ile Ala Lys Cys Leu Lys Glu Phe Val Asp Glu Trp Tyr Pro Asp
    130                 135                 140

-continued

```
Gly Val Ser Glu Pro Leu Pro Leu Gly Phe Thr Phe Ser Tyr Pro Ala
145                 150                 155                 160

Ser Gln Lys Lys Ile Asn Ser Gly Val Leu Gln Arg Trp Thr Lys Gly
            165                 170                 175

Phe Asp Ile Glu Gly Val Glu Gly His Asp Val Val Pro Met Leu Gln
        180                 185                 190

Glu Gln Ile Glu Lys Leu Asn Ile Pro Ile Asn Val Val Arg Leu Ile
    195                 200                 205

Asn Asp Thr Thr Gly Thr Leu Val Ala Ser Leu Tyr Thr Asp Pro Gln
210                 215                 220

Thr Lys Met Gly Ile Ile Ile Gly Thr Gly Val Asn Gly Ala Tyr Tyr
225                 230                 235                 240

Asp Val Val Ser Gly Ile Glu Lys Leu Glu Gly Leu Pro Glu Asp
            245                 250                 255

Ile Gly Pro Asp Ser Pro Met Ala Ile Asn Cys Glu Tyr Gly Ser Phe
        260                 265                 270

Asp Asn Glu His Leu Val Leu Pro Arg Thr Lys Tyr Asp Val Ile Ile
    275                 280                 285

Asp Glu Glu Ser Pro Arg Pro Gly Gln Gln Ala Phe Glu Lys Met Thr
290                 295                 300

Ser Gly Tyr Tyr Leu Gly Glu Ile Met Arg Leu Val Leu Leu Asp Leu
305                 310                 315                 320

Tyr Asp Ser Gly Phe Ile Phe Lys Asp Gln Asp Ile Ser Lys Leu Lys
            325                 330                 335

Glu Ala Tyr Val Met Asp Thr Ser Tyr Pro Ser Lys Ile Glu Asp Asp
        340                 345                 350

Pro Phe Glu Asn Leu Glu Asp Thr Asp Leu Phe Lys Thr Asn Leu
    355                 360                 365

Asn Ile Glu Thr Thr Val Val Glu Arg Lys Leu Ile Arg Lys Leu Ala
370                 375                 380

Glu Leu Val Gly Thr Arg Ala Ala Arg Leu Thr Val Cys Gly Val Ser
385                 390                 395                 400

Ala Ile Cys Asp Lys Arg Gly Tyr Lys Thr Ala His Ile Ala Ala Asp
            405                 410                 415

Gly Ser Val Phe Asn Arg Tyr Pro Gly Tyr Lys Glu Lys Ala Ala Gln
        420                 425                 430

Ala Leu Lys Asp Ile Tyr Asn Trp Asp Val Glu Lys Met Glu Asp His
    435                 440                 445

Pro Ile Gln Leu Val Ala Ala Glu Asp Gly Ser Gly Val Gly Ala Ala
450                 455                 460

Ile Ile Ala Cys Leu Thr Gln Lys Arg Leu Ala Ala Gly Lys Ser Val
465                 470                 475                 480

Gly Ile Lys Gly Glu
            485

<210> SEQ ID NO 9
<211> LENGTH: 1494
<212> TYPE: DNA
<213> ORGANISM: Tuber borchii
<220> FEATURE:
<221> NAME/KEY: CDS
<222> LOCATION: (1)..(1494)

<400> SEQUENCE: 9 atg tat ctc aat gca tct cgc aag ccg cct agc cgc aaa ggc tcc atg    48
Met Tyr Leu Asn Ala Ser Arg Lys Pro Pro Ser Arg Lys Gly Ser Met
```

```
                -continued
1               5               10              15 cac gat gtg ccg aac gat ctt atg aag cat atc cat gac ctc gag aag    96
His Asp Val Pro Asn Asp Leu Met Lys His Ile His Asp Leu Glu Lys
            20              25              30 atg ttc acc atc gat acc aca aag ctc cat gag gtt gtg tcc gta ttc    144
Met Phe Thr Ile Asp Thr Thr Lys Leu His Glu Val Val Ser Val Phe
            35              40              45 cag gag gaa ctc gtc aag ggg tta tcc gtg aca gga ggc aca att ccc    192
Gln Glu Glu Leu Val Lys Gly Leu Ser Val Thr Gly Gly Thr Ile Pro
        50              55              60 atg aac ccg act tgg gtg att gga tat cct act ggt gat gag aca ggc    240
Met Asn Pro Thr Trp Val Ile Gly Tyr Pro Thr Gly Asp Glu Thr Gly
65              70              75              80 acc tac ctc gct ctt gat atg ggt gga aca aat ctt cgt gtt tgc gaa    288
Thr Tyr Leu Ala Leu Asp Met Gly Gly Thr Asn Leu Arg Val Cys Glu
                85              90              95 gtt gag ctt cct gaa gag cag ggc cag tat gac atc tat cag tcc aag    336
Val Glu Leu Pro Glu Glu Gln Gly Gln Tyr Asp Ile Tyr Gln Ser Lys
            100             105             110 tat cgc ctt cct gaa gag atc aaa tcc ggc acc ggt gaa caa ctt ttc    384
Tyr Arg Leu Pro Glu Glu Ile Lys Ser Gly Thr Gly Glu Gln Leu Phe
            115             120             125 gat tac att gcc gag tgt gtc aag cag ttc ttg atc gcc aat cac gag    432
Asp Tyr Ile Ala Glu Cys Val Lys Gln Phe Leu Ile Ala Asn His Glu
        130             135             140 ggc caa gac atc aag gat ttg aag gag cta cat ctt ggt ttt aca ttc    480
Gly Gln Asp Ile Lys Asp Leu Lys Glu Leu His Leu Gly Phe Thr Phe
145             150             155             160 tca tac ccg tgc gag cag aac gcc att gat cac ggt atc ttg cag cgt    528
Ser Tyr Pro Cys Glu Gln Asn Ala Ile Asp His Gly Ile Leu Gln Arg
                165             170             175 tgg act aaa ggt ttc gat att gaa ggt gtt gag ggt cat gac gtt gtt    576
Trp Thr Lys Gly Phe Asp Ile Glu Gly Val Glu Gly His Asp Val Val
            180             185             190 ccc atg ttc gaa gag gct ctt gag aga aaa ggg gtc cct atc aag att    624
Pro Met Phe Glu Glu Ala Leu Glu Arg Lys Gly Val Pro Ile Lys Ile
            195             200             205 act gct tta gtc aat gac act acc gga act ctt atc gct tcc gct tat    672
Thr Ala Leu Val Asn Asp Thr Thr Gly Thr Leu Ile Ala Ser Ala Tyr
        210             215             220 acc gac aac act acc aga att ggt tgc att ttc ggt act ggt tgc aac    720
Thr Asp Asn Thr Thr Arg Ile Gly Cys Ile Phe Gly Thr Gly Cys Asn
225             230             235             240 gct gcc tac atg gag act atc ggc tgc att cct aaa ctt gct cat atg    768
Ala Ala Tyr Met Glu Thr Ile Gly Cys Ile Pro Lys Leu Ala His Met
                245             250             255 aat ctc gat cct agt ctt gag att gcc att aac tgt gaa tgg gga gcg    816
Asn Leu Asp Pro Ser Leu Glu Ile Ala Ile Asn Cys Glu Trp Gly Ala
            260             265             270 ttc gac aat gaa cat cgc gtc ctt cct cgt act gta tat gac aag cat    864
Phe Asp Asn Glu His Arg Val Leu Pro Arg Thr Val Tyr Asp Lys His
            275             280             285 atc gat gaa aac tct ccc cgc ccg ggg cag caa aca ttt gag aag atg    912
Ile Asp Glu Asn Ser Pro Arg Pro Gly Gln Gln Thr Phe Glu Lys Met
        290             295             300 gtt gcc ggt ctt tac tta gga gaa atc ttc cgt ttg gtt ctc gtc gat    960
Val Ala Gly Leu Tyr Leu Gly Glu Ile Phe Arg Leu Val Leu Val Asp
305             310             315             320 ctc tat tct aat cct gat gtt tca att ttt gaa aag cag gac att agt    1008
```

```
Leu Tyr Ser Asn Pro Asp Val Ser Ile Phe Glu Lys Gln Asp Ile Ser
            325                 330                 335 act ctt cag gct gag tac tct ttg gat gca tcc ttc cta gcc gag att   1056
Thr Leu Gln Ala Glu Tyr Ser Leu Asp Ala Ser Phe Leu Ala Glu Ile
        340                 345                 350 gag agc gat cct tgg gag aat ttg atg gaa act cat gct ctc ttt gag   1104
Glu Ser Asp Pro Trp Glu Asn Leu Met Glu Thr His Ala Leu Phe Glu
            355                 360                 365 aag aag ttg aag att gtg acc acc gag cct gag cgt aag ctc atc cgc   1152
Lys Lys Leu Lys Ile Val Thr Thr Glu Pro Glu Arg Lys Leu Ile Arg
        370                 375                 380 cgc ctt gcg gag ctc atc gga act cgc gct gct cgt ctt ggg gcc tgt   1200
Arg Leu Ala Glu Leu Ile Gly Thr Arg Ala Ala Arg Leu Gly Ala Cys
385                 390                 395                 400 ggt gtt gcc gcc att tgc aag atg aag aat att gag tct tgc cat gtt   1248
Gly Val Ala Ala Ile Cys Lys Met Lys Asn Ile Glu Ser Cys His Val
                405                 410                 415 ggt gct gac ggc tca gtg ttc aac aag tat ccc aac ttc cag gag cgt   1296
Gly Ala Asp Gly Ser Val Phe Asn Lys Tyr Pro Asn Phe Gln Glu Arg
            420                 425                 430 ggt gca aag gct ctt cgc gaa atc ttc ggc tgg gga aga aca att aga   1344
Gly Ala Lys Ala Leu Arg Glu Ile Phe Gly Trp Gly Arg Thr Ile Arg
        435                 440                 445 aag gat cct atc cag att gtt ccc tct gag gac gga agt ggc gtc ggc   1392
Lys Asp Pro Ile Gln Ile Val Pro Ser Glu Asp Gly Ser Gly Val Gly
450                 455                 460 gcc gct ttg atc gca gca ctc acc atg aag cgt att agg aag ggt att   1440
Ala Ala Leu Ile Ala Ala Leu Thr Met Lys Arg Ile Arg Lys Gly Ile
                465                 470                 475                 480 cat gct ggt gtt aac gtc aag cgc aag aac tcg ttg att cct ccg gtc   1488
His Ala Gly Val Asn Val Lys Arg Lys Asn Ser Leu Ile Pro Pro Val
            485                 490                 495 cca taa                                                           1494
Pro

<210> SEQ ID NO 10
<211> LENGTH: 497
<212> TYPE: PRT
<213> ORGANISM: Tuber borchii

<400> SEQUENCE: 10

Met Tyr Leu Asn Ala Ser Arg Lys Pro Pro Ser Arg Lys Gly Ser Met
1               5                   10                  15

His Asp Val Pro Asn Asp Leu Met Lys His Ile His Asp Leu Glu Lys
            20                  25                  30

Met Phe Thr Ile Asp Thr Thr Lys Leu His Glu Val Val Ser Val Phe
        35                  40                  45

Gln Glu Glu Leu Val Lys Gly Leu Ser Val Thr Gly Gly Thr Ile Pro
    50                  55                  60

Met Asn Pro Thr Trp Val Ile Gly Tyr Pro Thr Gly Asp Glu Thr Gly
65                  70                  75                  80

Thr Tyr Leu Ala Leu Asp Met Gly Gly Thr Asn Leu Arg Val Cys Glu
                85                  90                  95

Val Glu Leu Pro Glu Glu Gln Gly Gln Tyr Asp Ile Tyr Gln Ser Lys
            100                 105                 110

Tyr Arg Leu Pro Glu Glu Ile Lys Ser Gly Thr Gly Glu Gln Leu Phe
        115                 120                 125

Asp Tyr Ile Ala Glu Cys Val Lys Gln Phe Leu Ile Ala Asn His Glu
```

```
            130                 135                 140
Gly Gln Asp Ile Lys Asp Leu Lys Glu Leu His Leu Gly Phe Thr Phe
145                 150                 155                 160

Ser Tyr Pro Cys Glu Gln Asn Ala Ile Asp His Gly Ile Leu Gln Arg
                165                 170                 175

Trp Thr Lys Gly Phe Asp Ile Glu Gly Val Glu Gly His Asp Val Val
            180                 185                 190

Pro Met Phe Glu Glu Ala Leu Glu Arg Lys Gly Val Pro Ile Lys Ile
        195                 200                 205

Thr Ala Leu Val Asn Asp Thr Thr Gly Thr Leu Ile Ala Ser Ala Tyr
210                 215                 220

Thr Asp Asn Thr Thr Arg Ile Gly Cys Ile Phe Gly Thr Gly Cys Asn
225                 230                 235                 240

Ala Ala Tyr Met Glu Thr Ile Gly Cys Ile Pro Lys Leu Ala His Met
                245                 250                 255

Asn Leu Asp Pro Ser Leu Glu Ile Ala Ile Asn Cys Glu Trp Gly Ala
            260                 265                 270

Phe Asp Asn Glu His Arg Val Leu Pro Arg Thr Val Tyr Asp Lys His
        275                 280                 285

Ile Asp Glu Asn Ser Pro Arg Pro Gly Gln Gln Thr Phe Glu Lys Met
290                 295                 300

Val Ala Gly Leu Tyr Leu Gly Glu Ile Phe Arg Leu Val Leu Val Asp
305                 310                 315                 320

Leu Tyr Ser Asn Pro Asp Val Ser Ile Phe Glu Lys Gln Asp Ile Ser
                325                 330                 335

Thr Leu Gln Ala Glu Tyr Ser Leu Asp Ala Ser Phe Leu Ala Glu Ile
            340                 345                 350

Glu Ser Asp Pro Trp Glu Asn Leu Met Glu Thr His Ala Leu Phe Glu
        355                 360                 365

Lys Lys Leu Lys Ile Val Thr Thr Glu Pro Glu Arg Lys Leu Ile Arg
370                 375                 380

Arg Leu Ala Glu Leu Ile Gly Thr Arg Ala Ala Arg Leu Gly Ala Cys
385                 390                 395                 400

Gly Val Ala Ala Ile Cys Lys Met Lys Asn Ile Glu Ser Cys His Val
                405                 410                 415

Gly Ala Asp Gly Ser Val Phe Asn Lys Tyr Pro Asn Phe Gln Glu Arg
            420                 425                 430

Gly Ala Lys Ala Leu Arg Glu Ile Phe Gly Trp Gly Arg Thr Ile Arg
        435                 440                 445

Lys Asp Pro Ile Gln Ile Val Pro Ser Glu Asp Gly Ser Gly Val Gly
450                 455                 460

Ala Ala Leu Ile Ala Ala Leu Thr Met Lys Arg Ile Arg Lys Gly Ile
465                 470                 475                 480

His Ala Gly Val Asn Val Lys Arg Lys Asn Ser Leu Ile Pro Pro Val
                485                 490                 495

Pro

<210> SEQ ID NO 11
<211> LENGTH: 1900
<212> TYPE: DNA
<213> ORGANISM: Schizosaccharomyces pombe
<220> FEATURE:
<221> NAME/KEY: CDS
<222> LOCATION: (327)..(1577)
```

<400> SEQUENCE: 11

```
ctctaaagtt gcttttgaaa ttttaaagat cttttctt tcctacgtaa ctccaagtgt      60
caaggaattg ccatctttc acttcttcct ttcttttgtg tatcactact gaagttatca    120
aaatgtcctt gcacgacgct taccattggc cttctcgtac acctagtcgt aagggttcaa    180
atatcaaatt gaacaaaact ttacaagatc atttggatga actggaagaa caattcacca    240
ttcccactga acttttacat cgcgttaccg atcgctttgt ttctgagctt tacaagggct    300
taaccacgaa cccgggtgat gttcca atg gtc ccc aca tgg atc att ggt act    353
                              Met Val Pro Thr Trp Ile Ile Gly Thr
                                1               5 cct gat ggc aat gag cat ggc tct tat ttg gca tta gat tta ggt ggt      401
Pro Asp Gly Asn Glu His Gly Ser Tyr Leu Ala Leu Asp Leu Gly Gly
 10              15                  20                  25 act aac ttg cgt gtt tgt gca gtt gag gtt caa ggc aac ggt aaa ttc      449
Thr Asn Leu Arg Val Cys Ala Val Glu Val Gln Gly Asn Gly Lys Phe
                 30                  35                  40 gac att act caa agc aaa tac cgt cta cct caa gaa ctc aaa gtt ggc      497
Asp Ile Thr Gln Ser Lys Tyr Arg Leu Pro Gln Glu Leu Lys Val Gly
             45                  50                  55 act cgt gag gcc ctc ttt gat tac att gcc gac tgt atc aag aaa ttt      545
Thr Arg Glu Ala Leu Phe Asp Tyr Ile Ala Asp Cys Ile Lys Lys Phe
         60                  65                  70 gtg gaa gag gtt cac cca ggt aaa agc caa aat ttg gaa att ggt ttc      593
Val Glu Glu Val His Pro Gly Lys Ser Gln Asn Leu Glu Ile Gly Phe
 75                  80                  85 acc ttt tct tac ccc tgt gtt caa cgc tcc att aac gat gct tca tta      641
Thr Phe Ser Tyr Pro Cys Val Gln Arg Ser Ile Asn Asp Ala Ser Leu
 90                  95                 100                 105 gtt gcc tgg act aag ggc ttt gat att gat ggc gtt gag ggt gaa agt      689
Val Ala Trp Thr Lys Gly Phe Asp Ile Asp Gly Val Glu Gly Glu Ser
                110                 115                 120 gta ggt cct ctt tta tca gca gcc ttg aag cgt gtt ggg tgt aac aac      737
Val Gly Pro Leu Leu Ser Ala Ala Leu Lys Arg Val Gly Cys Asn Asn
            125                 130                 135 gtt aga ctc aat gcc att ttg agt gat act act ggt aca ttg gtt gct      785
Val Arg Leu Asn Ala Ile Leu Ser Asp Thr Thr Gly Thr Leu Val Ala
        140                 145                 150 tcc aac tat gcc agc cca ggt act gag att ggt gtc atc ttt gga act      833
Ser Asn Tyr Ala Ser Pro Gly Thr Glu Ile Gly Val Ile Phe Gly Thr
155                 160                 165 gga tgt aat gct tgt tac att gaa aag ttc tca gaa att cct aag ctt      881
Gly Cys Asn Ala Cys Tyr Ile Glu Lys Phe Ser Glu Ile Pro Lys Leu
170                 175                 180                 185 cat aag tat gac ttc cct gaa gat atg aac atg atc atc aac tgt gaa      929
His Lys Tyr Asp Phe Pro Glu Asp Met Asn Met Ile Ile Asn Cys Glu
                190                 195                 200 tgg tgc gat ttt gac aac cag cat gtt gtc ctt cct cgt acc aaa tac      977
Trp Cys Asp Phe Asp Asn Gln His Val Val Leu Pro Arg Thr Lys Tyr
            205                 210                 215 gat gtt gct att gat gaa gag tct ccc aga ccc ggt ctt caa acg tac     1025
Asp Val Ala Ile Asp Glu Glu Ser Pro Arg Pro Gly Leu Gln Thr Tyr
        220                 225                 230 gag aaa atg att gct gga tgc tat ttg ggt gat atc ttg cgt cgt att     1073
Glu Lys Met Ile Ala Gly Cys Tyr Leu Gly Asp Ile Leu Arg Arg Ile
    235                 240                 245 ctt ctt gac ctt tat gaa cag gga gct ctc ttt aac ggt cag gac gtt     1121
Leu Leu Asp Leu Tyr Glu Gln Gly Ala Leu Phe Asn Gly Gln Asp Val
250                 255                 260                 265
```

```
acc aag att cgt gac ccc ttg gcc atg gat acc tct gtg ctc agc gct    1169
Thr Lys Ile Arg Asp Pro Leu Ala Met Asp Thr Ser Val Leu Ser Ala
            270                 275                 280 att gaa gtt gac ccc ttt gag aac ctt gat gaa act caa acc cta ttt    1217
Ile Glu Val Asp Pro Phe Glu Asn Leu Asp Glu Thr Gln Thr Leu Phe
        285                 290                 295 gag gaa acc tat ggt ctc aag acc acc gaa gaa gag cgt caa ttc att    1265
Glu Glu Thr Tyr Gly Leu Lys Thr Thr Glu Glu Glu Arg Gln Phe Ile
    300                 305                 310 cgt cgt gca tgc gaa ttg att gga act cgt tct gcc cgt ctt tct gcg    1313
Arg Arg Ala Cys Glu Leu Ile Gly Thr Arg Ser Ala Arg Leu Ser Ala
315                 320                 325 tgt ggt gta tgc gcc ctt gtt cgt aaa atg aat aag cca tct atg att    1361
Cys Gly Val Cys Ala Leu Val Arg Lys Met Asn Lys Pro Ser Met Ile
330                 335                 340                 345 gta ggt act gat ggt agt gtc tac aac tta tac cct cgt ttt aag gat    1409
Val Gly Thr Asp Gly Ser Val Tyr Asn Leu Tyr Pro Arg Phe Lys Asp
            350                 355                 360 cgt ctt gct caa gca ttt aag gat atc ctt ggt gag gaa att ggc agc    1457
Arg Leu Ala Gln Ala Phe Lys Asp Ile Leu Gly Glu Glu Ile Gly Ser
        365                 370                 375 aaa gtt gtt acc atc ccc gcc gaa gac ggt agt ggc gta ggt gct gca    1505
Lys Val Val Thr Ile Pro Ala Glu Asp Gly Ser Gly Val Gly Ala Ala
    380                 385                 390 ttg gtc agt gct ctt gaa gcc aaa ggc aag gcc ctc act tct gat att    1553
Leu Val Ser Ala Leu Glu Ala Lys Gly Lys Ala Leu Thr Ser Asp Ile
395                 400                 405 ctt gcc gag cat ctt aag aat taa gtccactcat tgttttagg ttttacggat    1607
Leu Ala Glu His Leu Lys Asn
410                 415 actcatttga ttttgtgtca ctgaactcca cgaagtgttc gacaaactgt tttatactgc    1667 acttttat tgtttcatac tccatctttt tgcgtacaat tgttccagc aattttatg       1727 gttacacttt tctttgtcta ctaatcacgt atcagggcgt ttttacaaaa aggtgctcca    1787
cctgataaaa tattttcttt tttgctctag tgtttctgtg gatacgatat ctgcctctga    1847
ttgctagaat actttaaata aaggttagag ttttgttata aaaaaaaaaa aaa           1900
```

<210> SEQ ID NO 12
<211> LENGTH: 416
<212> TYPE: PRT
<213> ORGANISM: Schizosaccharomyces pombe

<400> SEQUENCE: 12

```
Met Val Pro Thr Trp Ile Ile Gly Thr Pro Asp Gly Asn Glu His Gly
1               5                   10                  15

Ser Tyr Leu Ala Leu Asp Leu Gly Gly Thr Asn Leu Arg Val Cys Ala
            20                  25                  30

Val Glu Val Gln Gly Asn Gly Lys Phe Asp Ile Thr Gln Ser Lys Tyr
        35                  40                  45

Arg Leu Pro Gln Glu Leu Lys Val Gly Thr Arg Glu Ala Leu Phe Asp
    50                  55                  60

Tyr Ile Ala Asp Cys Ile Lys Lys Phe Val Glu Glu Val His Pro Gly
65                  70                  75                  80

Lys Ser Gln Asn Leu Glu Ile Gly Phe Thr Phe Ser Tyr Pro Cys Val
                85                  90                  95

Gln Arg Ser Ile Asn Asp Ala Ser Leu Val Ala Trp Thr Lys Gly Phe
            100                 105                 110
```

-continued

Asp Ile Asp Gly Val Glu Gly Glu Ser Val Gly Pro Leu Leu Ser Ala
        115                 120                 125

Ala Leu Lys Arg Val Gly Cys Asn Asn Val Arg Leu Asn Ala Ile Leu
    130                 135                 140

Ser Asp Thr Thr Gly Thr Leu Val Ala Ser Asn Tyr Ala Ser Pro Gly
145                 150                 155                 160

Thr Glu Ile Gly Val Ile Phe Gly Thr Gly Cys Asn Ala Cys Tyr Ile
                165                 170                 175

Glu Lys Phe Ser Glu Ile Pro Lys Leu His Lys Tyr Asp Phe Pro Glu
            180                 185                 190

Asp Met Asn Met Ile Ile Asn Cys Glu Trp Cys Asp Phe Asp Asn Gln
        195                 200                 205

His Val Val Leu Pro Arg Thr Lys Tyr Asp Val Ala Ile Asp Glu Glu
    210                 215                 220

Ser Pro Arg Pro Gly Leu Gln Thr Tyr Glu Lys Met Ile Ala Gly Cys
225                 230                 235                 240

Tyr Leu Gly Asp Ile Leu Arg Arg Ile Leu Leu Asp Leu Tyr Glu Gln
                245                 250                 255

Gly Ala Leu Phe Asn Gly Gln Asp Val Thr Lys Ile Arg Asp Pro Leu
            260                 265                 270

Ala Met Asp Thr Ser Val Leu Ser Ala Ile Glu Val Asp Pro Phe Glu
        275                 280                 285

Asn Leu Asp Glu Thr Gln Thr Leu Phe Glu Gly Thr Tyr Gly Leu Lys
    290                 295                 300

Thr Thr Glu Glu Glu Arg Gln Phe Ile Arg Arg Ala Cys Glu Leu Ile
305                 310                 315                 320

Gly Thr Arg Ser Ala Arg Leu Ser Ala Cys Gly Val Cys Ala Leu Val
                325                 330                 335

Arg Lys Met Asn Lys Pro Ser Met Ile Val Gly Thr Asp Gly Ser Val
            340                 345                 350

Tyr Asn Leu Tyr Pro Arg Phe Lys Asp Arg Leu Ala Gln Ala Phe Lys
        355                 360                 365

Asp Ile Leu Gly Glu Glu Ile Gly Ser Lys Val Val Thr Ile Pro Ala
    370                 375                 380

Glu Asp Gly Ser Gly Val Gly Ala Ala Leu Val Ser Ala Leu Glu Ala
385                 390                 395                 400

Lys Gly Lys Ala Leu Thr Ser Asp Ile Leu Ala Glu His Leu Lys Asn
                405                 410                 415

<210> SEQ ID NO 13
<211> LENGTH: 1416
<212> TYPE: DNA
<213> ORGANISM: Pichia angusta
<220> FEATURE:
<221> NAME/KEY: CDS
<222> LOCATION: (1)..(1416)

<400> SEQUENCE: 13

```
atg agt ttg gat act gaa gtc gat aag att gtg tcg gag ttt gcc gtc      48
Met Ser Leu Asp Thr Glu Val Asp Lys Ile Val Ser Glu Phe Ala Val
1               5                   10                  15 acc cag gag aca ctc caa aag ggt gtg gag cgt ttc att gag ctt gca      96
Thr Gln Glu Thr Leu Gln Lys Gly Val Glu Arg Phe Ile Glu Leu Ala
                20                  25                  30 act gcc gga ctg aat agt gat gag gac aag tat ggt ctg cca atg atc     144
Thr Ala Gly Leu Asn Ser Asp Glu Asp Lys Tyr Gly Leu Pro Met Ile
```

-continued

|  | 35 |  |  |  | 40 |  |  |  | 45 |  |  |  |  |
|---|---|---|---|---|---|---|---|---|---|---|---|---|---|
| cca | act | ttt | gtt | acc | tcc | atc | cca | acc | ggt | aaa | gag | aag | ggc | att | ctt | 192 |
| Pro | Thr | Phe | Val | Thr | Ser | Ile | Pro | Thr | Gly | Lys | Glu | Lys | Gly | Ile | Leu |  |
|  | 50 |  |  |  | 55 |  |  |  |  |  | 60 |  |  |  |  |  |

```
cca act ttt gtt acc tcc atc cca acc ggt aaa gag aag ggc att ctt    192
Pro Thr Phe Val Thr Ser Ile Pro Thr Gly Lys Glu Lys Gly Ile Leu
    50              55                  60 ttt gcc gca gac ttg gga gga acc aat ttc aga gtt tgc tct gtt gcc    240
Phe Ala Ala Asp Leu Gly Gly Thr Asn Phe Arg Val Cys Ser Val Ala
65              70                  75                  80 ttg aac gga gat cac act ttc aaa ctg atc cag cag aag tca cat att    288
Leu Asn Gly Asp His Thr Phe Lys Leu Ile Gln Gln Lys Ser His Ile
                85                  90                  95 cct gcc gaa ctg atg acc tcc acc tcg gac gaa ttg ttt tcg tat ctt    336
Pro Ala Glu Leu Met Thr Ser Thr Ser Asp Glu Leu Phe Ser Tyr Leu
            100                 105                 110 gca agc aag gtc aag aat ttc tta gag act cat cat gaa ggg gct gtt    384
Ala Ser Lys Val Lys Asn Phe Leu Glu Thr His His Glu Gly Ala Val
        115                 120                 125 act tct aca gga agc cag aaa ttc aag atg ggt ttc act ttc agt ttc    432
Thr Ser Thr Gly Ser Gln Lys Phe Lys Met Gly Phe Thr Phe Ser Phe
    130                 135                 140 cct gtc tcg cag acc gcc tta aac gcc ggt act ttg cta aga tgg acc    480
Pro Val Ser Gln Thr Ala Leu Asn Ala Gly Thr Leu Leu Arg Trp Thr
145                 150                 155                 160 aag gga ttc aat att ccg gat act gtt ggt caa gag gtt gtt tct cta    528
Lys Gly Phe Asn Ile Pro Asp Thr Val Gly Gln Glu Val Val Ser Leu
                165                 170                 175 ttc caa atg cat tta gac gcc cag gaa att cct gtt act gtg tct gcc    576
Phe Gln Met His Leu Asp Ala Gln Glu Ile Pro Val Thr Val Ser Ala
            180                 185                 190 ctg tcc aac gat act gtg gga acc ctt ctt gca aga tcc tac acg ggt    624
Leu Ser Asn Asp Thr Val Gly Thr Leu Leu Ala Arg Ser Tyr Thr Gly
        195                 200                 205 tcc aat aag gag ggc act act gtt cta gga tgc atc ttc gga acg gga    672
Ser Asn Lys Glu Gly Thr Thr Val Leu Gly Cys Ile Phe Gly Thr Gly
    210                 215                 220 aca aac ggt gct tac aac gag aag ctc gag aat atc aag aag ctt ccg    720
Thr Asn Gly Ala Tyr Asn Glu Lys Leu Glu Asn Ile Lys Lys Leu Pro
225                 230                 235                 240 gcc gag gtg aga gag aag ctg aag gct caa ggt gtc acc cac atg gtc    768
Ala Glu Val Arg Glu Lys Leu Lys Ala Gln Gly Val Thr His Met Val
                245                 250                 255 att aat act gaa tgg ggt tcc ttc gat aac cag ctc aag gtt ttg cca    816
Ile Asn Thr Glu Trp Gly Ser Phe Asp Asn Gln Leu Lys Val Leu Pro
            260                 265                 270 aat acg aag tat gac gct caa gtt gac gaa ctt acc ggc aat aag ggc    864
Asn Thr Lys Tyr Asp Ala Gln Val Asp Glu Leu Thr Gly Asn Lys Gly
        275                 280                 285 ttc cac atg ttt gaa aag cgt gtt tcc gga atg ttc ttg ggt gag att    912
Phe His Met Phe Glu Lys Arg Val Ser Gly Met Phe Leu Gly Glu Ile
    290                 295                 300 ctg aga cat att ttg gtc gac ctt cac tct aag gga gtg cta ttt act    960
Leu Arg His Ile Leu Val Asp Leu His Ser Lys Gly Val Leu Phe Thr
305                 310                 315                 320 cag tac gcc agc tac gaa tcc ctg ccc cac aga ttg agg acg ccg tgg   1008
Gln Tyr Ala Ser Tyr Glu Ser Leu Pro His Arg Leu Arg Thr Pro Trp
                325                 330                 335 gat ctg gac tct gag gtt ctc tca ctg att gag atc gac gaa tcc acc   1056
Asp Leu Asp Ser Glu Val Leu Ser Leu Ile Glu Ile Asp Glu Ser Thr
            340                 345                 350 aat ttg cag gcc act gag ctg tct ttg aaa cag gca ttg aga ctg cca   1104
Asn Leu Gln Ala Thr Glu Leu Ser Leu Lys Gln Ala Leu Arg Leu Pro
```

-continued

```
                Asn Leu Gln Ala Thr Glu Leu Ser Leu Lys Gln Ala Leu Arg Leu Pro
                                355                 360                 365 act act act gag gag aga ctt gct att caa aaa ctt act cgt gct gtg       1152
Thr Thr Thr Glu Glu Arg Leu Ala Ile Gln Lys Leu Thr Arg Ala Val
370                 375                 380 gcc aag aga tct gcc tat ctt gct gct att cct att gct gct att cta       1200
Ala Lys Arg Ser Ala Tyr Leu Ala Ala Ile Pro Ile Ala Ala Ile Leu
385                 390                 395                 400 cac atg acc gag tct ttt aag ggc cac aac gtt gag gtg gac gtt gga       1248
His Met Thr Glu Ser Phe Lys Gly His Asn Val Glu Val Asp Val Gly
                405                 410                 415 gca gac ggg tct gtg gtt gag ttc tac cct gga ttc aga act atg atg       1296
Ala Asp Gly Ser Val Val Glu Phe Tyr Pro Gly Phe Arg Thr Met Met
                420                 425                 430 aga gac gcc att gcg cag acg cag ata ggt gcc aaa gga gag aga aga       1344
Arg Asp Ala Ile Ala Gln Thr Gln Ile Gly Ala Lys Gly Glu Arg Arg
            435                 440                 445 ctg cac att aac att gcc aaa gac ggc tca tct gtg ggc gct gca ttg       1392
Leu His Ile Asn Ile Ala Lys Asp Gly Ser Ser Val Gly Ala Ala Leu
        450                 455                 460 tgc gca tta agc gag aaa gac taa                                       1416
Cys Ala Leu Ser Glu Lys Asp
465                 470
```

<210> SEQ ID NO 14
<211> LENGTH: 471
<212> TYPE: PRT
<213> ORGANISM: Pichia angusta

<400> SEQUENCE: 14

```
Met Ser Leu Asp Thr Glu Val Asp Lys Ile Val Ser Glu Phe Ala Val
1               5                   10                  15

Thr Gln Glu Thr Leu Gln Lys Gly Val Glu Arg Phe Ile Glu Leu Ala
            20                  25                  30

Thr Ala Gly Leu Asn Ser Asp Glu Asp Lys Tyr Gly Leu Pro Met Ile
        35                  40                  45

Pro Thr Phe Val Thr Ser Ile Pro Thr Gly Lys Glu Lys Gly Ile Leu
    50                  55                  60

Phe Ala Ala Asp Leu Gly Gly Thr Asn Phe Arg Val Cys Ser Val Ala
65                  70                  75                  80

Leu Asn Gly Asp His Thr Phe Lys Leu Ile Gln Gln Lys Ser His Ile
                85                  90                  95

Pro Ala Glu Leu Met Thr Ser Thr Ser Asp Glu Leu Phe Ser Tyr Leu
            100                 105                 110

Ala Ser Lys Val Lys Asn Phe Leu Glu Thr His His Glu Gly Ala Val
        115                 120                 125

Thr Ser Thr Gly Ser Gln Lys Phe Lys Met Gly Phe Thr Phe Ser Phe
    130                 135                 140

Pro Val Ser Gln Thr Ala Leu Asn Ala Gly Thr Leu Leu Arg Trp Thr
145                 150                 155                 160

Lys Gly Phe Asn Ile Pro Asp Thr Val Gly Gln Glu Val Val Ser Leu
                165                 170                 175

Phe Gln Met His Leu Asp Ala Gln Glu Ile Pro Val Thr Val Ser Ala
            180                 185                 190

Leu Ser Asn Asp Thr Val Gly Thr Leu Leu Ala Arg Ser Tyr Thr Gly
        195                 200                 205

Ser Asn Lys Glu Gly Thr Thr Val Leu Gly Cys Ile Phe Gly Thr Gly
```

```
                    210                 215                 220
Thr Asn Gly Ala Tyr Asn Glu Lys Leu Glu Asn Ile Lys Lys Leu Pro
225                 230                 235                 240

Ala Glu Val Arg Glu Lys Leu Lys Ala Gln Gly Val Thr His Met Val
                245                 250                 255

Ile Asn Thr Glu Trp Gly Ser Phe Asp Asn Gln Leu Lys Val Leu Pro
                260                 265                 270

Asn Thr Lys Tyr Asp Ala Gln Val Asp Glu Leu Thr Gly Asn Lys Gly
                275                 280                 285

Phe His Met Phe Glu Lys Arg Val Ser Gly Met Phe Leu Gly Glu Ile
290                 295                 300

Leu Arg His Ile Leu Val Asp Leu His Ser Lys Gly Val Leu Phe Thr
305                 310                 315                 320

Gln Tyr Ala Ser Tyr Glu Ser Leu Pro His Arg Leu Arg Thr Pro Trp
                325                 330                 335

Asp Leu Asp Ser Glu Val Leu Ser Leu Ile Glu Ile Asp Glu Ser Thr
                340                 345                 350

Asn Leu Gln Ala Thr Glu Leu Ser Leu Lys Gln Ala Leu Arg Leu Pro
                355                 360                 365

Thr Thr Thr Glu Glu Arg Leu Ala Ile Gln Lys Leu Thr Arg Ala Val
370                 375                 380

Ala Lys Arg Ser Ala Tyr Leu Ala Ala Ile Pro Ile Ala Ala Ile Leu
385                 390                 395                 400

His Met Thr Glu Ser Phe Lys Gly His Asn Val Glu Val Asp Val Gly
                405                 410                 415

Ala Asp Gly Ser Val Val Glu Phe Tyr Pro Gly Phe Arg Thr Met Met
                420                 425                 430

Arg Asp Ala Ile Ala Gln Thr Gln Ile Gly Ala Lys Gly Glu Arg Arg
                435                 440                 445

Leu His Ile Asn Ile Ala Lys Asp Gly Ser Ser Val Gly Ala Ala Leu
                450                 455                 460

Cys Ala Leu Ser Glu Lys Asp
465                 470

<210> SEQ ID NO 15
<211> LENGTH: 1461
<212> TYPE: DNA
<213> ORGANISM: Saccharomyces cerevisiae
<220> FEATURE:
<221> NAME/KEY: CDS
<222> LOCATION: (1)..(1461)

<400> SEQUENCE: 15 atg gtt cat tta ggt cca aaa aaa cca caa gcc aga aag ggt tcc atg    48
Met Val His Leu Gly Pro Lys Lys Pro Gln Ala Arg Lys Gly Ser Met
1               5                   10                  15 gcc gat gtg cca aag gaa ttg atg caa caa att gag aat ttt gaa aaa    96
Ala Asp Val Pro Lys Glu Leu Met Gln Gln Ile Glu Asn Phe Glu Lys
            20                  25                  30 att ttc act gtt cca act gaa act tta caa gcc gtt acc aag cac ttc   144
Ile Phe Thr Val Pro Thr Glu Thr Leu Gln Ala Val Thr Lys His Phe
        35                  40                  45 att tcc gaa ttg gaa aag ggt ttg tcc aag aag ggt ggt aac att cca   192
Ile Ser Glu Leu Glu Lys Gly Leu Ser Lys Lys Gly Gly Asn Ile Pro
    50                  55                  60 atg att cca ggt tgg gtt atg gat ttc cca act ggt aag gaa tcc ggt   240
Met Ile Pro Gly Trp Val Met Asp Phe Pro Thr Gly Lys Glu Ser Gly
```

-continued

```
                  65                  70                  75                  80
gat ttc ttg gcc att gat ttg ggt ggt acc aac ttg aga gtt gtc tta          288
Asp Phe Leu Ala Ile Asp Leu Gly Gly Thr Asn Leu Arg Val Val Leu
                          85                  90                  95 gtc aag ttg ggc ggt gac cgt acc ttt gac acc act caa tct aag tac          336
Val Lys Leu Gly Gly Asp Arg Thr Phe Asp Thr Thr Gln Ser Lys Tyr
                         100                 105                 110 aga tta cca gat gct atg aga act act caa aat cca gac gaa ttg tgg          384
Arg Leu Pro Asp Ala Met Arg Thr Thr Gln Asn Pro Asp Glu Leu Trp
                 115                 120                 125 gaa ttt att gcc gac tct ttg aaa gct ttt att gat gag caa ttc cca          432
Glu Phe Ile Ala Asp Ser Leu Lys Ala Phe Ile Asp Glu Gln Phe Pro
         130                 135                 140 caa ggt atc tct gag cca att cca ttg ggt ttc acc ttt tct ttc cca          480
Gln Gly Ile Ser Glu Pro Ile Pro Leu Gly Phe Thr Phe Ser Phe Pro
     145                 150                 155                 160 gct tct caa aac aaa atc aat gaa ggt atc ttg caa aga tgg act aaa          528
Ala Ser Gln Asn Lys Ile Asn Glu Gly Ile Leu Gln Arg Trp Thr Lys
                         165                 170                 175 ggt ttt gat att cca aac att gaa aac cac gat gtt gtt cca atg ttg          576
Gly Phe Asp Ile Pro Asn Ile Glu Asn His Asp Val Val Pro Met Leu
                 180                 185                 190 caa aag caa atc act aag agg aat atc cca att gaa gtt gtt gct ttg          624
Gln Lys Gln Ile Thr Lys Arg Asn Ile Pro Ile Glu Val Val Ala Leu
         195                 200                 205 ata aac gac act acc ggt act ttg gtt gct tct tac tac act gac cca          672
Ile Asn Asp Thr Thr Gly Thr Leu Val Ala Ser Tyr Tyr Thr Asp Pro
     210                 215                 220 gaa act aag atg ggt gtt atc ttc ggt act ggt gtc aat ggt gct tac          720
Glu Thr Lys Met Gly Val Ile Phe Gly Thr Gly Val Asn Gly Ala Tyr
225                 230                 235                 240 tac gat gtt tgt tcc gat atc gaa aag cta caa gga aaa cta tct gat          768
Tyr Asp Val Cys Ser Asp Ile Glu Lys Leu Gln Gly Lys Leu Ser Asp
                 245                 250                 255 gac att cca cca tct gct cca atg gcc atc aac tgt gaa tac ggt tcc          816
Asp Ile Pro Pro Ser Ala Pro Met Ala Ile Asn Cys Glu Tyr Gly Ser
         260                 265                 270 ttc gac aat gaa cat gtc gtt ttg cca aga act aaa tac gat atc acc          864
Phe Asp Asn Glu His Val Val Leu Pro Arg Thr Lys Tyr Asp Ile Thr
     275                 280                 285 att gat gaa gaa tct cca aga cca ggc caa caa acc ttt gaa aaa atg          912
Ile Asp Glu Glu Ser Pro Arg Pro Gly Gln Gln Thr Phe Glu Lys Met
         290                 295                 300 tct tct ggt tac tac tta ggt gaa att ttg cgt ttg gcc ttg atg gac          960
Ser Ser Gly Tyr Tyr Leu Gly Glu Ile Leu Arg Leu Ala Leu Met Asp
305                 310                 315                 320 atg tac aaa caa ggt ttc atc ttc aaa aac caa gac ttg tct aag ttc         1008
Met Tyr Lys Gln Gly Phe Ile Phe Lys Asn Gln Asp Leu Ser Lys Phe
                 325                 330                 335 gac aag cct ttc gtc atg gac act tct tac cca gcc aga atc gag gaa         1056
Asp Lys Pro Phe Val Met Asp Thr Ser Tyr Pro Ala Arg Ile Glu Glu
         340                 345                 350 gat cca ttc gag aac cta gaa gat acc gat gac ttg ttc caa aat gag         1104
Asp Pro Phe Glu Asn Leu Glu Asp Thr Asp Asp Leu Phe Gln Asn Glu
     355                 360                 365 ttc ggt atc aac act act gtt caa gaa cgt aaa ttg atc aga cgt tta         1152
Phe Gly Ile Asn Thr Thr Val Gln Glu Arg Lys Leu Ile Arg Arg Leu
         370                 375                 380 tct gaa ttg att ggt gct aga gct gct aga ttg tcc gtt tgt ggt att         1200
```

```
Ser Glu Leu Ile Gly Ala Arg Ala Ala Arg Leu Ser Val Cys Gly Ile
385                 390                 395                 400 gct gct atc tgt caa aag aga ggt tac aag acc ggt cac atc gct gca      1248
Ala Ala Ile Cys Gln Lys Arg Gly Tyr Lys Thr Gly His Ile Ala Ala
                405                 410                 415 gac ggt tcc gtt tac aac aga tac cca ggt ttc aaa gaa aag gct gcc      1296
Asp Gly Ser Val Tyr Asn Arg Tyr Pro Gly Phe Lys Glu Lys Ala Ala
            420                 425                 430 aat gct ttg aag gac att tac ggc tgg act caa acc tca cta gac gac      1344
Asn Ala Leu Lys Asp Ile Tyr Gly Trp Thr Gln Thr Ser Leu Asp Asp
        435                 440                 445 tac cca atc aag att gtt cct gct gaa gat ggt tcc ggt gct ggt gcc      1392
Tyr Pro Ile Lys Ile Val Pro Ala Glu Asp Gly Ser Gly Ala Gly Ala
    450                 455                 460 gct gtt att gct gct ttg gcc caa aaa aga att gct gaa ggt aag tcc      1440
Ala Val Ile Ala Ala Leu Ala Gln Lys Arg Ile Ala Glu Gly Lys Ser
465                 470                 475                 480 gtt ggt atc atc ggt gct taa                                          1461
Val Gly Ile Ile Gly Ala
                485
```

<210> SEQ ID NO 16
<211> LENGTH: 486
<212> TYPE: PRT
<213> ORGANISM: Saccharomyces cerevisiae

<400> SEQUENCE: 16

```
Met Val His Leu Gly Pro Lys Lys Pro Gln Ala Arg Lys Gly Ser Met
1               5                   10                  15

Ala Asp Val Pro Lys Glu Leu Met Gln Gln Ile Glu Asn Phe Glu Lys
            20                  25                  30

Ile Phe Thr Val Pro Thr Glu Thr Leu Gln Ala Val Thr Lys His Phe
        35                  40                  45

Ile Ser Glu Leu Glu Lys Gly Leu Ser Lys Lys Gly Gly Asn Ile Pro
    50                  55                  60

Met Ile Pro Gly Trp Val Met Asp Phe Pro Thr Gly Lys Glu Ser Gly
65                  70                  75                  80

Asp Phe Leu Ala Ile Asp Leu Gly Gly Thr Asn Leu Arg Val Val Leu
                85                  90                  95

Val Lys Leu Gly Gly Asp Arg Thr Phe Asp Thr Thr Gln Ser Lys Tyr
            100                 105                 110

Arg Leu Pro Asp Ala Met Arg Thr Thr Gln Asn Pro Asp Glu Leu Trp
        115                 120                 125

Glu Phe Ile Ala Asp Ser Leu Lys Ala Phe Ile Asp Glu Gln Phe Pro
    130                 135                 140

Gln Gly Ile Ser Glu Pro Ile Pro Leu Gly Phe Thr Phe Ser Phe Pro
145                 150                 155                 160

Ala Ser Gln Asn Lys Ile Asn Glu Gly Ile Leu Gln Arg Trp Thr Lys
                165                 170                 175

Gly Phe Asp Ile Pro Asn Ile Glu Asn His Asp Val Val Pro Met Leu
            180                 185                 190

Gln Lys Gln Ile Thr Lys Arg Asn Ile Pro Ile Glu Val Val Ala Leu
        195                 200                 205

Ile Asn Asp Thr Thr Gly Thr Leu Val Ala Ser Tyr Tyr Thr Asp Pro
    210                 215                 220

Glu Thr Lys Met Gly Val Ile Phe Gly Thr Gly Val Asn Gly Ala Tyr
225                 230                 235                 240
```

```
Tyr Asp Val Cys Ser Asp Ile Glu Lys Leu Gln Gly Lys Leu Ser Asp
                245                 250                 255

Asp Ile Pro Pro Ser Ala Pro Met Ala Ile Asn Cys Glu Tyr Gly Ser
            260                 265                 270

Phe Asp Asn Glu His Val Val Leu Pro Arg Thr Lys Tyr Asp Ile Thr
        275                 280                 285

Ile Asp Glu Glu Ser Pro Arg Pro Gly Gln Gln Thr Phe Glu Lys Met
    290                 295                 300

Ser Ser Gly Tyr Tyr Leu Gly Glu Ile Leu Arg Leu Ala Leu Met Asp
305                 310                 315                 320

Met Tyr Lys Gln Gly Phe Ile Phe Lys Asn Gln Asp Leu Ser Lys Phe
                325                 330                 335

Asp Lys Pro Phe Val Met Asp Thr Ser Tyr Pro Ala Arg Ile Glu Glu
            340                 345                 350

Asp Pro Phe Glu Asn Leu Glu Asp Thr Asp Asp Leu Phe Gln Asn Glu
        355                 360                 365

Phe Gly Ile Asn Thr Thr Val Gln Glu Arg Lys Leu Ile Arg Arg Leu
    370                 375                 380

Ser Glu Leu Ile Gly Ala Arg Ala Ala Arg Leu Ser Val Cys Gly Ile
385                 390                 395                 400

Ala Ala Ile Cys Gln Lys Arg Gly Tyr Lys Thr Gly His Ile Ala Ala
                405                 410                 415

Asp Gly Ser Val Tyr Asn Arg Tyr Pro Gly Phe Lys Glu Lys Ala Ala
            420                 425                 430

Asn Ala Leu Lys Asp Ile Tyr Gly Trp Thr Gln Thr Ser Leu Asp Asp
        435                 440                 445

Tyr Pro Ile Lys Ile Val Pro Ala Glu Asp Gly Ser Gly Ala Gly Ala
    450                 455                 460

Ala Val Ile Ala Ala Leu Ala Gln Lys Arg Ile Ala Glu Gly Lys Ser
465                 470                 475                 480

Val Gly Ile Ile Gly Ala
                485

<210> SEQ ID NO 17
<211> LENGTH: 1696
<212> TYPE: DNA
<213> ORGANISM: Yarrowia lipolytica
<220> FEATURE:
<221> NAME/KEY: CDS
<222> LOCATION: (77)..(1681)

<400> SEQUENCE: 17
tacagataaa acacaaaggt ttcgttcacc ctatactccg aatcaacgct acctactgca      60
tttctctacc gcaaca atg gtt cat ctt ggt ccc cga aaa ccc ccg tcc cga    112
               Met Val His Leu Gly Pro Arg Lys Pro Pro Ser Arg
                 1               5                  10 aag ggc tca atg gca gac gtc ccg cgg gac ctg ctg gag caa atc tcc      160
Lys Gly Ser Met Ala Asp Val Pro Arg Asp Leu Leu Glu Gln Ile Ser
            15                  20                  25 cag ctt gaa acc atc ttc acc gtt tcg ccc gaa aag ctg cgt caa atc      208
Gln Leu Glu Thr Ile Phe Thr Val Ser Pro Glu Lys Leu Arg Gln Ile
        30                  35                  40 acc gac cac ttt gtg tcc gag ctc gct aaa ggc ctc aca aag gag ggt      256
Thr Asp His Phe Val Ser Glu Leu Ala Lys Gly Leu Thr Lys Glu Gly
45                  50                  55                  60 gga gat atc ccc atg aac ccc acc tgg att ctg gga tgg ccc acc gga      304
```

```
Gly Asp Ile Pro Met Asn Pro Thr Trp Ile Leu Gly Trp Pro Thr Gly
             65                  70                  75 aag gag agc ggc tgc tat ctg gct ctc gac atg ggt ggc acc aac ctg      352
Lys Glu Ser Gly Cys Tyr Leu Ala Leu Asp Met Gly Gly Thr Asn Leu
             80                  85                  90 cga gtt gtc aag gtg act ctg gac ggc gac cga ggc ttc gac gtc atg      400
Arg Val Val Lys Val Thr Leu Asp Gly Asp Arg Gly Phe Asp Val Met
             95                 100                 105 cag tcc aag tac cac atg ccc ccc aac atc aag gtc ggc aag caa gag      448
Gln Ser Lys Tyr His Met Pro Pro Asn Ile Lys Val Gly Lys Gln Glu
       110                 115                 120 gag ctg tgg gag tac att gcc gaa tgt ctg ggc aag ttc ttg gcc gac      496
Glu Leu Trp Glu Tyr Ile Ala Glu Cys Leu Gly Lys Phe Leu Ala Asp
125                 130                 135                 140 aat tat cct gag gct ctt gat gcc cat gag cga gga cga gat gtc gac      544
Asn Tyr Pro Glu Ala Leu Asp Ala His Glu Arg Gly Arg Asp Val Asp
                145                 150                 155 aga acc gct gcg cag agc ttc act cga gac aag tct cct cct ccc cac      592
Arg Thr Ala Ala Gln Ser Phe Thr Arg Asp Lys Ser Pro Pro Pro His
                160                 165                 170 aac cag cac att tcg tgt tct cct ggc ttc gac atc cac aag att cct      640
Asn Gln His Ile Ser Cys Ser Pro Gly Phe Asp Ile His Lys Ile Pro
        175                 180                 185 ctc ggt ttc acc ttt tca tat ccc tgc tct cag ccc gcc gtc aac cga      688
Leu Gly Phe Thr Phe Ser Tyr Pro Cys Ser Gln Pro Ala Val Asn Arg
        190                 195                 200 ggt gta ctg cag cga tgg acc aag ggt ttc gac att gag gga gtc gag      736
Gly Val Leu Gln Arg Trp Thr Lys Gly Phe Asp Ile Glu Gly Val Glu
205                 210                 215                 220 ggc gag gac gtg gtc ccc atg ctg gaa gct gcc ctc gaa aga aag aac      784
Gly Glu Asp Val Val Pro Met Leu Glu Ala Ala Leu Glu Arg Lys Asn
                225                 230                 235 att cct att tcc atc acc gcc ctg atc aac gac acc acc gga act atg      832
Ile Pro Ile Ser Ile Thr Ala Leu Ile Asn Asp Thr Thr Gly Thr Met
                240                 245                 250 gtg gcc tcc aac tac cac gac ccc cag atc aag ctg ggt aac atc ttt      880
Val Ala Ser Asn Tyr His Asp Pro Gln Ile Lys Leu Gly Asn Ile Phe
        255                 260                 265 ggt act ggt gtc aac gcc gcc tac tac gag aag gtc aag gac att ccc      928
Gly Thr Gly Val Asn Ala Ala Tyr Tyr Glu Lys Val Lys Asp Ile Pro
        270                 275                 280 aag ctc aag ggt ctc atc ccc gac agc att gat ccc gag acc ccc atg      976
Lys Leu Lys Gly Leu Ile Pro Asp Ser Ile Asp Pro Glu Thr Pro Met
285                 290                 295                 300 gcc gtc aat tgc gag tat gga gcc ttc gac aat gag cac aag gtt ctc     1024
Ala Val Asn Cys Glu Tyr Gly Ala Phe Asp Asn Glu His Lys Val Leu
                305                 310                 315 cct aga acc aag tgg gac atc atc atc gat gag gag tct ccc cga ccc     1072
Pro Arg Thr Lys Trp Asp Ile Ile Ile Asp Glu Glu Ser Pro Arg Pro
                320                 325                 330 ggt cag cag acc ttc gag aag atg agt gct ggc tac tac ctg gga gaa     1120
Gly Gln Gln Thr Phe Glu Lys Met Ser Ala Gly Tyr Tyr Leu Gly Glu
        335                 340                 345 ttg ctt cgt ctg gtt ctt ctg gac ctg tac aag gac ggg ttt gtg ttc     1168
Leu Leu Arg Leu Val Leu Leu Asp Leu Tyr Lys Asp Gly Phe Val Phe
        350                 355                 360 gag aac cag ggc aag aac ggt cag gag ctt gga aac ggc aac atc aac     1216
Glu Asn Gln Gly Lys Asn Gly Gln Glu Leu Gly Asn Gly Asn Ile Asn
365                 370                 375                 380
```

-continued

```
aag tcg tat ttc ttc gac acc tct ttc ctg tct ctg att gag gag gat    1264
Lys Ser Tyr Phe Phe Asp Thr Ser Phe Leu Ser Leu Ile Glu Glu Asp
            385                 390                 395 ccc tgg gag aac ttg act gat gtc gag att ctc ttc aag gag aag ctt    1312
Pro Trp Glu Asn Leu Thr Asp Val Glu Ile Leu Phe Lys Glu Lys Leu
400                 405                 410 ggt att aac acc act gag ccc gag cga aag ctc att cgt cga ctg gcc    1360
Gly Ile Asn Thr Thr Glu Pro Glu Arg Lys Leu Ile Arg Arg Leu Ala
    415                 420                 425 gag ctc att ggt act cga tcc gct cga atc tct gcc tgt ggt gtc gct    1408
Glu Leu Ile Gly Thr Arg Ser Ala Arg Ile Ser Ala Cys Gly Val Ala
        430                 435                 440 gcc atc tgt aag aag gct ggc tac aag gag gct cac gct gga gct gac    1456
Ala Ile Cys Lys Lys Ala Gly Tyr Lys Glu Ala His Ala Gly Ala Asp
445                 450                 455                 460 gga tcc gtg ttc aac aag tac ccc gga ttc aag gag cga ggc gcc cag    1504
Gly Ser Val Phe Asn Lys Tyr Pro Gly Phe Lys Glu Arg Gly Ala Gln
                465                 470                 475 gct ctc aac gag att ttt gag tgg aac ctg ccc aac cct aag gac cac    1552
Ala Leu Asn Glu Ile Phe Glu Trp Asn Leu Pro Asn Pro Lys Asp His
            480                 485                 490 ccc atc aaa atc gtt ccc gct gag gat ggt agc ggt gtt gga gct gct    1600
Pro Ile Lys Ile Val Pro Ala Glu Asp Gly Ser Gly Val Gly Ala Ala
        495                 500                 505 ctg tgc gct gct ctc acc atc aag cga gtc aag cag ggt ctt ccc gtt    1648
Leu Cys Ala Ala Leu Thr Ile Lys Arg Val Lys Gln Gly Leu Pro Val
510                 515                 520 ggt gtc aag ccc ggt gtc aag tac gat att tag atgaccaaca aagat       1696
Gly Val Lys Pro Gly Val Lys Tyr Asp Ile
525                 530

<210> SEQ ID NO 18
<211> LENGTH: 534
<212> TYPE: PRT
<213> ORGANISM: Yarrowia lipolytica

<400> SEQUENCE: 18

Met Val His Leu Gly Pro Arg Lys Pro Ser Arg Lys Gly Ser Met
1               5                   10                  15

Ala Asp Val Pro Arg Asp Leu Leu Glu Gln Ile Ser Gln Leu Glu Thr
                20                  25                  30

Ile Phe Thr Val Ser Pro Glu Lys Leu Arg Gln Ile Thr Asp His Phe
            35                  40                  45

Val Ser Glu Leu Ala Lys Gly Leu Thr Lys Glu Gly Asp Ile Pro
        50                  55                  60

Met Asn Pro Thr Trp Ile Leu Gly Trp Pro Thr Gly Lys Glu Ser Gly
65                  70                  75                  80

Cys Tyr Leu Ala Leu Asp Met Gly Gly Thr Asn Leu Arg Val Val Lys
                85                  90                  95

Val Thr Leu Asp Gly Asp Arg Gly Phe Asp Val Met Gln Ser Lys Tyr
            100                 105                 110

His Met Pro Pro Asn Ile Lys Val Gly Lys Gln Glu Glu Leu Trp Glu
        115                 120                 125

Tyr Ile Ala Glu Cys Leu Gly Lys Phe Leu Ala Asp Asn Tyr Pro Glu
    130                 135                 140

Ala Leu Asp Ala His Glu Arg Gly Arg Asp Val Asp Arg Thr Ala Ala
145                 150                 155                 160

Gln Ser Phe Thr Arg Asp Lys Ser Pro Pro His Asn Gln His Ile
```

```
                  165                 170                 175
Ser Cys Ser Pro Gly Phe Asp Ile His Lys Ile Pro Leu Gly Phe Thr
        180                 185                 190
Phe Ser Tyr Pro Cys Ser Gln Pro Ala Val Asn Arg Gly Val Leu Gln
    195                 200                 205
Arg Trp Thr Lys Gly Phe Asp Ile Glu Gly Val Glu Gly Glu Asp Val
210                 215                 220
Val Pro Met Leu Glu Ala Ala Leu Glu Arg Lys Asn Ile Pro Ile Ser
225                 230                 235                 240
Ile Thr Ala Leu Ile Asn Asp Thr Thr Gly Thr Met Val Ala Ser Asn
                245                 250                 255
Tyr His Asp Pro Gln Ile Lys Leu Gly Asn Ile Phe Gly Thr Gly Val
            260                 265                 270
Asn Ala Ala Tyr Tyr Glu Lys Val Lys Asp Ile Pro Lys Leu Lys Gly
        275                 280                 285
Leu Ile Pro Asp Ser Ile Asp Pro Glu Thr Pro Met Ala Val Asn Cys
    290                 295                 300
Glu Tyr Gly Ala Phe Asp Asn Glu His Lys Val Leu Pro Arg Thr Lys
305                 310                 315                 320
Trp Asp Ile Ile Ile Asp Glu Glu Ser Pro Arg Pro Gly Gln Gln Thr
                325                 330                 335
Phe Glu Lys Met Ser Ala Gly Tyr Tyr Leu Gly Glu Leu Leu Arg Leu
            340                 345                 350
Val Leu Leu Asp Leu Tyr Lys Asp Gly Phe Val Phe Glu Asn Gln Gly
        355                 360                 365
Lys Asn Gly Gln Glu Leu Gly Asn Gly Asn Ile Asn Lys Ser Tyr Phe
    370                 375                 380
Phe Asp Thr Ser Phe Leu Ser Leu Ile Glu Glu Asp Pro Trp Glu Asn
385                 390                 395                 400
Leu Thr Asp Val Glu Ile Leu Phe Lys Glu Lys Leu Gly Ile Asn Thr
                405                 410                 415
Thr Glu Pro Glu Arg Lys Leu Ile Arg Arg Leu Ala Glu Leu Ile Gly
            420                 425                 430
Thr Arg Ser Ala Arg Ile Ser Ala Cys Gly Val Ala Ala Ile Cys Lys
        435                 440                 445
Lys Ala Gly Tyr Lys Glu Ala His Ala Gly Ala Asp Gly Ser Val Phe
    450                 455                 460
Asn Lys Tyr Pro Gly Phe Lys Glu Arg Gly Ala Gln Ala Leu Asn Glu
465                 470                 475                 480
Ile Phe Glu Trp Asn Leu Pro Asn Pro Lys Asp His Pro Ile Lys Ile
                485                 490                 495
Val Pro Ala Glu Asp Gly Ser Gly Val Gly Ala Ala Leu Cys Ala Ala
            500                 505                 510
Leu Thr Ile Lys Arg Val Lys Gln Gly Leu Pro Val Gly Val Lys Pro
        515                 520                 525
Gly Val Lys Tyr Asp Ile
        530

<210> SEQ ID NO 19
<211> LENGTH: 1473
<212> TYPE: DNA
<213> ORGANISM: Aspergillus niger
<220> FEATURE:
<221> NAME/KEY: CDS
<222> LOCATION: (1)..(1473)
```

<400> SEQUENCE: 19

```
atg gtt gga atc ggt cct aag cgt ccc ccc tcc cgc aag ggt tcc atg        48
Met Val Gly Ile Gly Pro Lys Arg Pro Pro Ser Arg Lys Gly Ser Met
1               5                   10                  15 gcc gat gtt ccc cag aac ctc ttg cag cag atc aag gac ttc gag gac        96
Ala Asp Val Pro Gln Asn Leu Leu Gln Gln Ile Lys Asp Phe Glu Asp
            20                  25                  30 caa ttc acc gtc gat cgc tcc aag ctc aag cag att gtc aac cac ttt       144
Gln Phe Thr Val Asp Arg Ser Lys Leu Lys Gln Ile Val Asn His Phe
        35                  40                  45 gtc aag gaa ttg gaa aag ggt ctc tct gtc gag ggt gga aac atc cct       192
Val Lys Glu Leu Glu Lys Gly Leu Ser Val Glu Gly Gly Asn Ile Pro
50                  55                  60 atg aac gtc acc tgg gtt ctg gga ttc ccc gat ggc gac gaa cag ggt       240
Met Asn Val Thr Trp Val Leu Gly Phe Pro Asp Gly Asp Glu Gln Gly
65                  70                  75                  80 act ttc ctc gcc ctc gac atg ggt ggc acc aac ctg cgt gtt tgt gag       288
Thr Phe Leu Ala Leu Asp Met Gly Gly Thr Asn Leu Arg Val Cys Glu
            85                  90                  95 atc acc ctg acc cag gag aag ggt gcc ttc gac atc acc cag tcc aag       336
Ile Thr Leu Thr Gln Glu Lys Gly Ala Phe Asp Ile Thr Gln Ser Lys
        100                 105                 110 tac cgc atg ccc gag gaa ttg aag acc ggt acc gcc gag gag ctg tgg       384
Tyr Arg Met Pro Glu Glu Leu Lys Thr Gly Thr Ala Glu Glu Leu Trp
    115                 120                 125 gaa tac atc gcc gac tgc ctg cag caa ttc atc gag tcc cac cac gag       432
Glu Tyr Ile Ala Asp Cys Leu Gln Gln Phe Ile Glu Ser His His Glu
130                 135                 140 aac gag aag atc tcc aag ctg ccc ctg ggt ttc acc ttc tcc tac ccc       480
Asn Glu Lys Ile Ser Lys Leu Pro Leu Gly Phe Thr Phe Ser Tyr Pro
145                 150                 155                 160 gcc acc cag gat tac atc gac cac ggt gtc ctg cag cgc tgg acc aag       528
Ala Thr Gln Asp Tyr Ile Asp His Gly Val Leu Gln Arg Trp Thr Lys
            165                 170                 175 ggt ttc gac att gat ggt gtc gag ggc cac gac gtc gtc ccg ccg ttg       576
Gly Phe Asp Ile Asp Gly Val Glu Gly His Asp Val Val Pro Pro Leu
        180                 185                 190 gag gcc atc ctg cag aag cgc ggc ctg ccc atc aag gtg gct gca ctg       624
Glu Ala Ile Leu Gln Lys Arg Gly Leu Pro Ile Lys Val Ala Ala Leu
    195                 200                 205 atc aac gac acc acc gga acc ctc atc gcc tct tct tac acc gac tcc       672
Ile Asn Asp Thr Thr Gly Thr Leu Ile Ala Ser Ser Tyr Thr Asp Ser
210                 215                 220 gac atg aag atc ggc tgc atc ttc ggt acc ggt gtc aac gcc gcc tac       720
Asp Met Lys Ile Gly Cys Ile Phe Gly Thr Gly Val Asn Ala Ala Tyr
225                 230                 235                 240 atg gag aac gcc ggc tcc atc ccc aag ctg gct cac atg aac ctg ccc       768
Met Glu Asn Ala Gly Ser Ile Pro Lys Leu Ala His Met Asn Leu Pro
            245                 250                 255 gcc gac atg ccc gtg gct atc aac tgc gag tac ggt gct ttc gac aac       816
Ala Asp Met Pro Val Ala Ile Asn Cys Glu Tyr Gly Ala Phe Asp Asn
        260                 265                 270 gag cac atc gtg ctg cct ctg acc aag tac gac cac atc atc gac cgc       864
Glu His Ile Val Leu Pro Leu Thr Lys Tyr Asp His Ile Ile Asp Arg
    275                 280                 285 gac tcg ccc cgt ccc ggt cag cag gcc ttc gag aag atg acc gcc ggt       912
Asp Ser Pro Arg Pro Gly Gln Gln Ala Phe Glu Lys Met Thr Ala Gly
290                 295                 300
```

```
ctg tac ctg ggt gag atc ttc cgt ctg gcc ctg atg gac ctg gtg gag    960
Leu Tyr Leu Gly Glu Ile Phe Arg Leu Ala Leu Met Asp Leu Val Glu
305                 310                 315                 320 aac cgc ccc ggc ctc atc ttc aac ggc cag gac acc acc aag ctg cgc   1008
Asn Arg Pro Gly Leu Ile Phe Asn Gly Gln Asp Thr Thr Lys Leu Arg
                325                 330                 335 aag ccc tac atc ctg gat gcc tcc ttc ctg gca gcc atc gag gag gac   1056
Lys Pro Tyr Ile Leu Asp Ala Ser Phe Leu Ala Ala Ile Glu Glu Asp
            340                 345                 350 ccc tac gag aac ctg gag gag acc gag gag ctc atg gag cgc gag ctc   1104
Pro Tyr Glu Asn Leu Glu Glu Thr Glu Glu Leu Met Glu Arg Glu Leu
        355                 360                 365 aac atc aag gcc acc ccg gcg gag ctg gag atg atc cgc cgc ctg gcc   1152
Asn Ile Lys Ala Thr Pro Ala Glu Leu Glu Met Ile Arg Arg Leu Ala
    370                 375                 380 gag ctg atc ggt acg cgt gcc gct cgc ctg tcg gcc tgc ggt gtt gcc   1200
Glu Leu Ile Gly Thr Arg Ala Ala Arg Leu Ser Ala Cys Gly Val Ala
385                 390                 395                 400 gcc att tgc acg aag aag aag atc gac tcg tgc cac gtt ggt gcc gac   1248
Ala Ile Cys Thr Lys Lys Lys Ile Asp Ser Cys His Val Gly Ala Asp
                405                 410                 415 ggc tcc gtc ttc acc aag tac cct cac ttc aag gcg cgc gga gcc aag   1296
Gly Ser Val Phe Thr Lys Tyr Pro His Phe Lys Ala Arg Gly Ala Lys
            420                 425                 430 gct ctg cgc gag atc ctg gac tgg gct ccg gag gag cag gac aag gtg   1344
Ala Leu Arg Glu Ile Leu Asp Trp Ala Pro Glu Glu Gln Asp Lys Val
        435                 440                 445 acc atc atg gcg gcc gag gat gga tct ggt gtg gga gct gcg ctg att   1392
Thr Ile Met Ala Ala Glu Asp Gly Ser Gly Val Gly Ala Ala Leu Ile
    450                 455                 460 gcg gcg ctg acc ctg aag cgg gtc aag gcc ggc aac ctg gcc ggt atc   1440
Ala Ala Leu Thr Leu Lys Arg Val Lys Ala Gly Asn Leu Ala Gly Ile
465                 470                 475                 480 cga aac atg gct gac atg aag acc ctg cta taa                       1473
Arg Asn Met Ala Asp Met Lys Thr Leu Leu
                485                 490
```

<210> SEQ ID NO 20
<211> LENGTH: 490
<212> TYPE: PRT
<213> ORGANISM: Aspergillus niger

<400> SEQUENCE: 20

```
Met Val Gly Ile Gly Pro Lys Arg Pro Pro Ser Arg Lys Gly Ser Met
1               5                   10                  15

Ala Asp Val Pro Gln Asn Leu Leu Gln Gln Ile Lys Asp Phe Glu Asp
            20                  25                  30

Gln Phe Thr Val Asp Arg Ser Lys Leu Lys Gln Ile Val Asn His Phe
        35                  40                  45

Val Lys Glu Leu Glu Lys Gly Leu Ser Val Glu Gly Gly Asn Ile Pro
    50                  55                  60

Met Asn Val Thr Trp Val Leu Gly Phe Pro Asp Gly Asp Glu Gln Gly
65                  70                  75                  80

Thr Phe Leu Ala Leu Asp Met Gly Gly Thr Asn Leu Arg Val Cys Glu
                85                  90                  95

Ile Thr Leu Thr Gln Glu Lys Gly Ala Phe Asp Ile Thr Gln Ser Lys
            100                 105                 110

Tyr Arg Met Pro Glu Glu Leu Lys Thr Gly Thr Ala Glu Glu Leu Trp
        115                 120                 125
```

Glu Tyr Ile Ala Asp Cys Leu Gln Gln Phe Ile Glu Ser His His Glu
    130                 135                 140

Asn Glu Lys Ile Ser Lys Leu Pro Leu Gly Phe Thr Phe Ser Tyr Pro
145                 150                 155                 160

Ala Thr Gln Asp Tyr Ile Asp His Gly Val Leu Gln Arg Trp Thr Lys
                165                 170                 175

Gly Phe Asp Ile Asp Gly Val Glu Gly His Asp Val Val Pro Pro Leu
            180                 185                 190

Glu Ala Ile Leu Gln Lys Arg Gly Leu Pro Ile Lys Val Ala Ala Leu
        195                 200                 205

Ile Asn Asp Thr Thr Gly Thr Leu Ile Ala Ser Ser Tyr Thr Asp Ser
    210                 215                 220

Asp Met Lys Ile Gly Cys Ile Phe Gly Thr Gly Val Asn Ala Ala Tyr
225                 230                 235                 240

Met Glu Asn Ala Gly Ser Ile Pro Lys Leu Ala His Met Asn Leu Pro
                245                 250                 255

Ala Asp Met Pro Val Ala Ile Asn Cys Glu Tyr Gly Ala Phe Asp Asn
            260                 265                 270

Glu His Ile Val Leu Pro Leu Thr Lys Tyr Asp His Ile Ile Asp Arg
        275                 280                 285

Asp Ser Pro Arg Pro Gly Gln Gln Ala Phe Glu Lys Met Thr Ala Gly
    290                 295                 300

Leu Tyr Leu Gly Glu Ile Phe Arg Leu Ala Leu Met Asp Leu Val Glu
305                 310                 315                 320

Asn Arg Pro Gly Leu Ile Phe Asn Gly Gln Asp Thr Thr Lys Leu Arg
                325                 330                 335

Lys Pro Tyr Ile Leu Asp Ala Ser Phe Leu Ala Ala Ile Glu Glu Asp
            340                 345                 350

Pro Tyr Glu Asn Leu Glu Glu Thr Glu Glu Leu Met Glu Arg Glu Leu
        355                 360                 365

Asn Ile Lys Ala Thr Pro Ala Glu Leu Glu Met Ile Arg Arg Leu Ala
    370                 375                 380

Glu Leu Ile Gly Thr Arg Ala Ala Arg Leu Ser Ala Cys Gly Val Ala
385                 390                 395                 400

Ala Ile Cys Thr Lys Lys Lys Ile Asp Ser Cys His Val Gly Ala Asp
                405                 410                 415

Gly Ser Val Phe Thr Lys Tyr Pro His Phe Lys Ala Arg Gly Ala Lys
            420                 425                 430

Ala Leu Arg Glu Ile Leu Asp Trp Ala Pro Glu Glu Gln Asp Lys Val
        435                 440                 445

Thr Ile Met Ala Ala Glu Asp Gly Ser Gly Val Gly Ala Ala Leu Ile
    450                 455                 460

Ala Ala Leu Thr Leu Lys Arg Val Lys Ala Gly Asn Leu Ala Gly Ile
465                 470                 475                 480

Arg Asn Met Ala Asp Met Lys Thr Leu Leu
                485                 490

<210> SEQ ID NO 21
<211> LENGTH: 1473
<212> TYPE: DNA
<213> ORGANISM: Aspergillus oryzae
<220> FEATURE:
<221> NAME/KEY: CDS
<222> LOCATION: (1)..(1473)

<400> SEQUENCE: 21

```
atg gtt gga att ggc ccc aaa cgt ccc cca tcc cgc aag gga tcg atg       48
Met Val Gly Ile Gly Pro Lys Arg Pro Pro Ser Arg Lys Gly Ser Met
1               5                   10                  15 cat gag ctg ccc cag aac ctg ttg gag cag atc aag caa ttc gag gac       96
His Glu Leu Pro Gln Asn Leu Leu Glu Gln Ile Lys Gln Phe Glu Asp
            20                  25                  30 atc ttt acc gtg gac ggc gcc aaa ctc aag cag att gcg gac cat ttc      144
Ile Phe Thr Val Asp Gly Ala Lys Leu Lys Gln Ile Ala Asp His Phe
        35                  40                  45 gtg aag gag ctc gaa aag ggt cta agc gtc gag ggg ggt aac att ccc      192
Val Lys Glu Leu Glu Lys Gly Leu Ser Val Glu Gly Gly Asn Ile Pro
    50                  55                  60 atg aat gtg acc tgg gtc atg gga ttc ccc gat ggc gac gag cag gga      240
Met Asn Val Thr Trp Val Met Gly Phe Pro Asp Gly Asp Glu Gln Gly
65                  70                  75                  80 acc ttc ctc gct ttg gac atg ggc ggt act aat ctg cgt gtc tgt gag      288
Thr Phe Leu Ala Leu Asp Met Gly Gly Thr Asn Leu Arg Val Cys Glu
                85                  90                  95 atc act ttg acg gaa gag aag ggc gct ttc gac atc acc cag tcc aag      336
Ile Thr Leu Thr Glu Glu Lys Gly Ala Phe Asp Ile Thr Gln Ser Lys
            100                 105                 110 tat cgt atg ccg gag gag ttg aag acg ggt aca gcg gag gag ctt tgg      384
Tyr Arg Met Pro Glu Glu Leu Lys Thr Gly Thr Ala Glu Glu Leu Trp
        115                 120                 125 gaa tac atc gcc gac tgt ttg cag cag ttt att gaa tcc cac cac gag      432
Glu Tyr Ile Ala Asp Cys Leu Gln Gln Phe Ile Glu Ser His His Glu
    130                 135                 140 aat gag aaa ctg tct aaa ctg cca ttg ggc ttt acc ttc tcc tat cct      480
Asn Glu Lys Leu Ser Lys Leu Pro Leu Gly Phe Thr Phe Ser Tyr Pro
145                 150                 155                 160 gct aca cag gaa tac att gat cat ggt gtt ctc cag cgt tgg aca aag      528
Ala Thr Gln Glu Tyr Ile Asp His Gly Val Leu Gln Arg Trp Thr Lys
                165                 170                 175 ggt ttc gac att gac gga gta gag ggc cag gat gtt gtg ccc cca ttg      576
Gly Phe Asp Ile Asp Gly Val Glu Gly Gln Asp Val Val Pro Pro Leu
            180                 185                 190 gag gca atc ctc aag aaa aga ggc ctt cct atc aaa gtt gct gcg ttg      624
Glu Ala Ile Leu Lys Lys Arg Gly Leu Pro Ile Lys Val Ala Ala Leu
        195                 200                 205 atc aac gac act acg ggc acc ctg atc gcc tct tct tac acc gac tca      672
Ile Asn Asp Thr Thr Gly Thr Leu Ile Ala Ser Ser Tyr Thr Asp Ser
    210                 215                 220 gat atg aaa att ggc tgc att ttc ggc act ggt gtc aac gcc gcc tac      720
Asp Met Lys Ile Gly Cys Ile Phe Gly Thr Gly Val Asn Ala Ala Tyr
225                 230                 235                 240 atg gaa cat tgt ggc tcg gtt ccc aag ctt gca cac aag aat cta ccc      768
Met Glu His Cys Gly Ser Val Pro Lys Leu Ala His Lys Asn Leu Pro
                245                 250                 255 cca gac atg ccc gtg gcc atc aac tgc gag tac ggt gcc ttt gac aat      816
Pro Asp Met Pro Val Ala Ile Asn Cys Glu Tyr Gly Ala Phe Asp Asn
            260                 265                 270 gag cac gtt gtt ctg ccc ctc acg aag tat gat atc atc atc gac cgc      864
Glu His Val Val Leu Pro Leu Thr Lys Tyr Asp Ile Ile Ile Asp Arg
        275                 280                 285 gac tcc cct cgc cca gga caa caa gct ttc gag aag atg act gca ggt      912
Asp Ser Pro Arg Pro Gly Gln Gln Ala Phe Glu Lys Met Thr Ala Gly
    290                 295                 300 ctt tac ttg gga gaa ata ttc cgt cta gcc ctc ttg gat ctg ttg gag      960
Leu Tyr Leu Gly Glu Ile Phe Arg Leu Ala Leu Leu Asp Leu Leu Glu
```

```
Leu Tyr Leu Gly Glu Ile Phe Arg Leu Ala Leu Leu Asp Leu Leu Glu
305                 310                 315                 320 acg agg cct ggt ctg att ttc cag ggc caa gac aca tcc cag ctc cgg      1008
Thr Arg Pro Gly Leu Ile Phe Gln Gly Gln Asp Thr Ser Gln Leu Arg
                325                 330                 335 aaa cct tac ttg ctg gac gcg tcc ttc ctc gca gct att gag gat gat      1056
Lys Pro Tyr Leu Leu Asp Ala Ser Phe Leu Ala Ala Ile Glu Asp Asp
            340                 345                 350 ccg tac gag aac ttg cag gaa act cag gag ctc atg gag cgc aag ctg      1104
Pro Tyr Glu Asn Leu Gln Glu Thr Gln Glu Leu Met Glu Arg Lys Leu
        355                 360                 365 aac atc aag gcc acc cag cag gag ctg gaa atg atc cgt cgc ttg gcg      1152
Asn Ile Lys Ala Thr Gln Gln Glu Leu Glu Met Ile Arg Arg Leu Ala
    370                 375                 380 gag ttg atc ggc act cgt gca gct cgt ctg tcg gcg tgt ggt gtg gct      1200
Glu Leu Ile Gly Thr Arg Ala Ala Arg Leu Ser Ala Cys Gly Val Ala
385                 390                 395                 400 gcc atc tgc aag aag aag aac att gag tct tgc cat gtg ggc gcc gac      1248
Ala Ile Cys Lys Lys Lys Asn Ile Glu Ser Cys His Val Gly Ala Asp
                405                 410                 415 ggc tct gtc ttt acg aaa tat ccc cac ttc aag gcc cgt gga gca cag      1296
Gly Ser Val Phe Thr Lys Tyr Pro His Phe Lys Ala Arg Gly Ala Gln
            420                 425                 430 gct ctg cgc gag atc ttg gac tgg gca cct aac gag aag gac aag gtg      1344
Ala Leu Arg Glu Ile Leu Asp Trp Ala Pro Asn Glu Lys Asp Lys Val
        435                 440                 445 gtc atc atg gct gct gaa gac ggt tct ggt gtt gga gcg gct ctt att      1392
Val Ile Met Ala Ala Glu Asp Gly Ser Gly Val Gly Ala Ala Leu Ile
    450                 455                 460 gct gca ttg aca ttg aag cgg gtc aag gca ggc atc agc tgc ggt atc      1440
Ala Ala Leu Thr Leu Lys Arg Val Lys Ala Gly Ile Ser Cys Gly Ile
465                 470                 475                 480 cga gat atg gcc gat atg cag agt ctc att taa                          1473
Arg Asp Met Ala Asp Met Gln Ser Leu Ile
                485                 490

<210> SEQ ID NO 22
<211> LENGTH: 490
<212> TYPE: PRT
<213> ORGANISM: Aspergillus oryzae

<400> SEQUENCE: 22

Met Val Gly Ile Gly Pro Lys Arg Pro Ser Arg Lys Gly Ser Met
1               5                   10                  15

His Glu Leu Pro Gln Asn Leu Leu Glu Gln Ile Lys Gln Phe Glu Asp
                20                  25                  30

Ile Phe Thr Val Asp Gly Ala Lys Leu Lys Gln Ile Ala Asp His Phe
            35                  40                  45

Val Lys Glu Leu Glu Lys Gly Leu Ser Val Glu Gly Asn Ile Pro
        50                  55                  60

Met Asn Val Thr Trp Val Met Gly Phe Pro Asp Gly Asp Glu Gln Gly
65                  70                  75                  80

Thr Phe Leu Ala Leu Asp Met Gly Thr Asn Leu Arg Val Cys Glu
                85                  90                  95

Ile Thr Leu Thr Glu Glu Lys Gly Ala Phe Asp Ile Thr Gln Ser Lys
            100                 105                 110

Tyr Arg Met Pro Glu Glu Leu Lys Thr Gly Thr Ala Glu Glu Leu Trp
        115                 120                 125
```

| Glu | Tyr | Ile | Ala | Asp | Cys | Leu | Gln | Gln | Phe | Ile | Glu | Ser | His | His | Glu |
|---|---|---|---|---|---|---|---|---|---|---|---|---|---|---|---|
| | 130 | | | | 135 | | | | | 140 | | | | | |

| Asn | Glu | Lys | Leu | Ser | Lys | Leu | Pro | Leu | Gly | Phe | Thr | Phe | Ser | Tyr | Pro |
|---|---|---|---|---|---|---|---|---|---|---|---|---|---|---|---|
| 145 | | | | | 150 | | | | | 155 | | | | | 160 |

| Ala | Thr | Gln | Glu | Tyr | Ile | Asp | His | Gly | Val | Leu | Gln | Arg | Trp | Thr | Lys |
|---|---|---|---|---|---|---|---|---|---|---|---|---|---|---|---|
| | | | 165 | | | | | 170 | | | | | 175 | | |

| Gly | Phe | Asp | Ile | Asp | Gly | Val | Glu | Gly | Gln | Asp | Val | Val | Pro | Pro | Leu |
|---|---|---|---|---|---|---|---|---|---|---|---|---|---|---|---|
| | | | 180 | | | | | 185 | | | | | 190 | | |

| Glu | Ala | Ile | Leu | Lys | Lys | Arg | Gly | Leu | Pro | Ile | Lys | Val | Ala | Ala | Leu |
|---|---|---|---|---|---|---|---|---|---|---|---|---|---|---|---|
| | 195 | | | | | 200 | | | | | 205 | | | | |

| Ile | Asn | Asp | Thr | Thr | Gly | Thr | Leu | Ile | Ala | Ser | Ser | Tyr | Thr | Asp | Ser |
|---|---|---|---|---|---|---|---|---|---|---|---|---|---|---|---|
| 210 | | | | | 215 | | | | | 220 | | | | | |

| Asp | Met | Lys | Ile | Gly | Cys | Ile | Phe | Gly | Thr | Gly | Val | Asn | Ala | Ala | Tyr |
|---|---|---|---|---|---|---|---|---|---|---|---|---|---|---|---|
| 225 | | | | | 230 | | | | | 235 | | | | | 240 |

| Met | Glu | His | Cys | Gly | Ser | Val | Pro | Lys | Leu | Ala | His | Lys | Asn | Leu | Pro |
|---|---|---|---|---|---|---|---|---|---|---|---|---|---|---|---|
| | | | | 245 | | | | | 250 | | | | | 255 | |

| Pro | Asp | Met | Pro | Val | Ala | Ile | Asn | Cys | Glu | Tyr | Gly | Ala | Phe | Asp | Asn |
|---|---|---|---|---|---|---|---|---|---|---|---|---|---|---|---|
| | | | 260 | | | | | 265 | | | | | 270 | | |

| Glu | His | Val | Val | Leu | Pro | Leu | Thr | Lys | Tyr | Asp | Ile | Ile | Ile | Asp | Arg |
|---|---|---|---|---|---|---|---|---|---|---|---|---|---|---|---|
| | 275 | | | | | 280 | | | | | 285 | | | | |

| Asp | Ser | Pro | Arg | Pro | Gly | Gln | Gln | Ala | Phe | Glu | Lys | Met | Thr | Ala | Gly |
|---|---|---|---|---|---|---|---|---|---|---|---|---|---|---|---|
| 290 | | | | | 295 | | | | | 300 | | | | | |

| Leu | Tyr | Leu | Gly | Glu | Ile | Phe | Arg | Leu | Ala | Leu | Asp | Leu | Leu | Glu |
|---|---|---|---|---|---|---|---|---|---|---|---|---|---|---|
| 305 | | | | | 310 | | | | | 315 | | | | 320 |

| Thr | Arg | Pro | Gly | Leu | Ile | Phe | Gln | Gly | Gln | Asp | Thr | Ser | Gln | Leu | Arg |
|---|---|---|---|---|---|---|---|---|---|---|---|---|---|---|---|
| | | | | 325 | | | | | 330 | | | | | 335 | |

| Lys | Pro | Tyr | Leu | Leu | Asp | Ala | Ser | Phe | Leu | Ala | Ala | Ile | Glu | Asp | Asp |
|---|---|---|---|---|---|---|---|---|---|---|---|---|---|---|---|
| | | | 340 | | | | | 345 | | | | | 350 | | |

| Pro | Tyr | Glu | Asn | Leu | Gln | Glu | Thr | Gln | Glu | Leu | Met | Glu | Arg | Lys | Leu |
|---|---|---|---|---|---|---|---|---|---|---|---|---|---|---|---|
| | 355 | | | | | 360 | | | | | 365 | | | | |

| Asn | Ile | Lys | Ala | Thr | Gln | Gln | Glu | Leu | Glu | Met | Ile | Arg | Arg | Leu | Ala |
|---|---|---|---|---|---|---|---|---|---|---|---|---|---|---|---|
| 370 | | | | | 375 | | | | | 380 | | | | | |

| Glu | Leu | Ile | Gly | Thr | Arg | Ala | Ala | Arg | Leu | Ser | Ala | Cys | Gly | Val | Ala |
|---|---|---|---|---|---|---|---|---|---|---|---|---|---|---|---|
| 385 | | | | | 390 | | | | | 395 | | | | | 400 |

| Ala | Ile | Cys | Lys | Lys | Lys | Asn | Ile | Glu | Ser | Cys | His | Val | Gly | Ala | Asp |
|---|---|---|---|---|---|---|---|---|---|---|---|---|---|---|---|
| | | | | 405 | | | | | 410 | | | | | 415 | |

| Gly | Ser | Val | Phe | Thr | Lys | Tyr | Pro | His | Phe | Lys | Ala | Arg | Gly | Ala | Gln |
|---|---|---|---|---|---|---|---|---|---|---|---|---|---|---|---|
| | | | 420 | | | | | 425 | | | | | 430 | | |

| Ala | Leu | Arg | Glu | Ile | Leu | Asp | Trp | Ala | Pro | Asn | Glu | Lys | Asp | Lys | Val |
|---|---|---|---|---|---|---|---|---|---|---|---|---|---|---|---|
| | 435 | | | | | 440 | | | | | 445 | | | | |

| Val | Ile | Met | Ala | Ala | Glu | Asp | Gly | Ser | Gly | Val | Gly | Ala | Ala | Leu | Ile |
|---|---|---|---|---|---|---|---|---|---|---|---|---|---|---|---|
| 450 | | | | | 455 | | | | | 460 | | | | | |

| Ala | Ala | Leu | Thr | Leu | Lys | Arg | Val | Lys | Ala | Gly | Ile | Ser | Cys | Gly | Ile |
|---|---|---|---|---|---|---|---|---|---|---|---|---|---|---|---|
| 465 | | | | | 470 | | | | | 475 | | | | | 480 |

| Arg | Asp | Met | Ala | Asp | Met | Gln | Ser | Leu | Ile |
|---|---|---|---|---|---|---|---|---|---|
| | | | | 485 | | | | | 490 |

```
<210> SEQ ID NO 23
<211> LENGTH: 1706
<212> TYPE: DNA
<213> ORGANISM: Aspergillus nidulans
<220> FEATURE:
<221> NAME/KEY: CDS
<222> LOCATION: (786)..(1694)

<400> SEQUENCE: 23
```

-continued

```
atggtcggag tcggtcccaa acgccctccc tctcgcaagg gtatgtcacc ccttccaacc      60
cagtgctcga attgattctt aatcgcacgc tcgtattgca ggttccatgt cagacgtgcc     120
ccaaaatctc ctggagcata ttaagcactt tgaggagatc ttcactgttg atactgccac     180
gcttaaaaag atcgttgacc atttcgtcaa cgagctgacg aagggtaagt ggtttggaac     240
ttaaattttt gaaaacgata cttaaattgg gacatttagg tctctctgtt gagggcggca     300
acattgtaag tcttcgaaat cgccattcgc atcgactatc taacggtata gcccatgaac     360
gtcacatggg ttcttggatt ccccgacgga aagaaacggg gcacgttcct ggccctcgat     420
atgggcggca cccaacctgc gggtttgtga aattaccctg accgaggaga aggtggatt      480 cgatatcatc aatccaaat accgaatgcc cgaggagctc aagaccggcg aggcagagga     540
gttgtggcaa tatatcgtcg actgcgtcga gcagtttatt cagttccacc acgagaacga     600
gaacctatct aaattgccgc tgggattcac gttctcctac cctgctactc aggactacat     660
cgaccacgga gttctccagc gctggaccaa gggtttcgac attgatggtg tcgaaggtaa     720
agacgtagtc ccgcctcttg agaaggtctt caaggaacgg gtatgaaca atctgatccc     780 tgcgc atg tgc ctg cgt ctg ctt acc ttt cct gtt gta ggg cct gcc cat      830
      Met Cys Leu Arg Leu Leu Thr Phe Pro Val Val Gly Pro Ala His
      1               5                   10                  15 caa ggt cgc tgc ctt gac aac gac aca acg gga ccc ttc att gct tct        878
Gln Gly Arg Cys Leu Asp Asn Asp Thr Thr Gly Pro Phe Ile Ala Ser
            20                  25                  30 tct tac acc gac ccc gct atg aag atc ggc tgc att ttc ggc acc ggt        926
Ser Tyr Thr Asp Pro Ala Met Lys Ile Gly Cys Ile Phe Gly Thr Gly
        35                  40                  45 gtg aat gca gca tac atg gag aat gct ggc tct att cca aag ctg gcc        974
Val Asn Ala Ala Tyr Met Glu Asn Ala Gly Ser Ile Pro Lys Leu Ala
    50                  55                  60 cac atg aat ctg cct ccg gac atg ccc gtc gcc atc aat tgc gaa tac       1022
His Met Asn Leu Pro Pro Asp Met Pro Val Ala Ile Asn Cys Glu Tyr
65                  70                  75 ggt gcc ttt gac aac gaa cat att gtc ctc ccg ctc acc aag tac gac       1070
Gly Ala Phe Asp Asn Glu His Ile Val Leu Pro Leu Thr Lys Tyr Asp
            80                  85                  90                  95 cac atc atc gac cgc gat tca cct cgt ccc ggc cag caa gct ttt gag       1118
His Ile Ile Asp Arg Asp Ser Pro Arg Pro Gly Gln Gln Ala Phe Glu
        100                 105                 110 aag atg acg gct ggt ctg tat ctg ggc gaa atc ttc cgc ttg gcc ttg       1166
Lys Met Thr Ala Gly Leu Tyr Leu Gly Glu Ile Phe Arg Leu Ala Leu
    115                 120                 125 gta gat att ttg gac aca cag ccg ggt cta atc ttc aag gat cag gat       1214
Val Asp Ile Leu Asp Thr Gln Pro Gly Leu Ile Phe Lys Asp Gln Asp
130                 135                 140 acc tcg cag ctg cgg atc cca tac ctt ctg gat tca tcc ttc ccc gca       1262
Thr Ser Gln Leu Arg Ile Pro Tyr Leu Leu Asp Ser Ser Phe Pro Ala
        145                 150                 155 gct atc gaa gaa gac cct tac gaa aac ctt atc gag acc gcc gaa ctc       1310
Ala Ile Glu Glu Asp Pro Tyr Glu Asn Leu Ile Glu Thr Ala Glu Leu
160                 165                 170                 175 gtc caa aac atg ctc aag ata aaa gca aca cgc tca gag ctc gaa ctg       1358
Val Gln Asn Met Leu Lys Ile Lys Ala Thr Arg Ser Glu Leu Glu Leu
            180                 185                 190 atg cgc cgg ctt gcc gag ctg atc ggt act cgc gct gct cgc cta tcc       1406
Met Arg Arg Leu Ala Glu Leu Ile Gly Thr Arg Ala Ala Arg Leu Ser
    195                 200                 205
```

```
gcc tgt ggt gtt gcc gca atc tgc aag aag aag aac atc gag tct tgc      1454
Ala Cys Gly Val Ala Ala Ile Cys Lys Lys Lys Asn Ile Glu Ser Cys
        210                 215                 220 cac gtc ggg gcc gac ggc tcg gta ttc aca aaa tac ccc cac ttc aag      1502
His Val Gly Ala Asp Gly Ser Val Phe Thr Lys Tyr Pro His Phe Lys
225                 230                 235 gcc cgc ggt gct cag gct ctg cgt gag atc ctc gac tgg gcc ccc agt      1550
Ala Arg Gly Ala Gln Ala Leu Arg Glu Ile Leu Asp Trp Ala Pro Ser
240                 245                 250                 255 gag aag gac aag gtc acc atc cat gct gcc gag gat ggg tct ggt gtg      1598
Glu Lys Asp Lys Val Thr Ile His Ala Ala Glu Asp Gly Ser Gly Val
                260                 265                 270 ggt gcg gct ctc atc gcc gcc ttg acc ctg aag cgt gtc aag gct ggc      1646
Gly Ala Ala Leu Ile Ala Ala Leu Thr Leu Lys Arg Val Lys Ala Gly
            275                 280                 285 aac acg gcc ggt att cgt gat gcg cag gcc atg ctg gct atg tgc tag     1694
Asn Thr Ala Gly Ile Arg Asp Ala Gln Ala Met Leu Ala Met Cys
        290                 295                 300 gcatatgcgt gc                                                        1706

<210> SEQ ID NO 24
<211> LENGTH: 302
<212> TYPE: PRT
<213> ORGANISM: Aspergillus nidulans

<400> SEQUENCE: 24

Met Cys Leu Arg Leu Leu Thr Phe Pro Val Val Gly Pro Ala His Gln
1               5                  10                  15

Gly Arg Cys Leu Asp Asn Asp Thr Thr Gly Pro Phe Ile Ala Ser Ser
            20                  25                  30

Tyr Thr Asp Pro Ala Met Lys Ile Gly Cys Ile Phe Thr Gly Val
        35                  40                  45

Asn Ala Ala Tyr Met Glu Asn Ala Gly Ser Ile Pro Lys Leu Ala His
    50                  55                  60

Met Asn Leu Pro Pro Asp Met Pro Val Ala Ile Asn Cys Glu Tyr Gly
65                  70                  75                  80

Ala Phe Asp Asn Glu His Ile Val Leu Pro Leu Thr Lys Tyr Asp His
                85                  90                  95

Ile Ile Asp Arg Asp Ser Pro Arg Pro Gly Gln Gln Ala Phe Glu Lys
            100                 105                 110

Met Thr Ala Gly Leu Tyr Leu Gly Glu Ile Phe Arg Leu Ala Leu Val
        115                 120                 125

Asp Ile Leu Asp Thr Gln Pro Gly Leu Ile Phe Lys Asp Gln Asp Thr
    130                 135                 140

Ser Gln Leu Arg Ile Pro Tyr Leu Leu Asp Ser Ser Phe Pro Ala Ala
145                 150                 155                 160

Ile Glu Glu Asp Pro Tyr Glu Asn Leu Ile Glu Thr Ala Glu Leu Val
                165                 170                 175

Gln Asn Met Leu Lys Ile Lys Ala Thr Arg Ser Glu Leu Glu Leu Met
            180                 185                 190

Arg Arg Leu Ala Glu Leu Ile Gly Thr Arg Ala Ala Arg Leu Ser Ala
        195                 200                 205

Cys Gly Val Ala Ala Ile Cys Lys Lys Lys Asn Ile Glu Ser Cys His
    210                 215                 220

Val Gly Ala Asp Gly Ser Val Phe Thr Lys Tyr Pro His Phe Lys Ala
225                 230                 235                 240
```

```
                    Arg Gly Ala Gln Ala Leu Arg Glu Ile Leu Asp Trp Ala Pro Ser Glu
                                    245                 250                 255

Lys Asp Lys Val Thr Ile His Ala Ala Glu Asp Gly Ser Gly Val Gly
                                260                 265                 270

Ala Ala Leu Ile Ala Ala Leu Thr Leu Lys Arg Val Lys Ala Gly Asn
                                275                 280                 285

Thr Ala Gly Ile Arg Asp Ala Gln Ala Met Leu Ala Met Cys
                                290                 295                 300

<210> SEQ ID NO 25
<211> LENGTH: 1230
<212> TYPE: DNA
<213> ORGANISM: Aspergillus nidulans
<220> FEATURE:
<221> NAME/KEY: CDS
<222> LOCATION: (4)..(1230)

<400> SEQUENCE: 25 cca atg aac gtg aca tgg gtc ccc tcg ttt cca aca ggc cat gaa aca        48
    Met Asn Val Thr Trp Val Pro Ser Phe Pro Thr Gly His Glu Thr
    1               5                   10                  15 ggc cgg tac ctt gcc att gac atg ggc ggc aca aat ctg cga atc tgc        96
Gly Arg Tyr Leu Ala Ile Asp Met Gly Gly Thr Asn Leu Arg Ile Cys
                20                  25                  30 gat gtg acc ctg acc gag gaa aag ggc gcg tat acg atc gag cag gac       144
Asp Val Thr Leu Thr Glu Glu Lys Gly Ala Tyr Thr Ile Glu Gln Asp
            35                  40                  45 aaa tac cgg ctt cca atc cat ctg agg aag ggc aaa ggg gtt gaa tta       192
Lys Tyr Arg Leu Pro Ile His Leu Arg Lys Gly Lys Gly Val Glu Leu
        50                  55                  60 tgg gag ttc att gca gca aaa ctc gag gac ttt ctc gct aaa cac aag       240
Trp Glu Phe Ile Ala Ala Lys Leu Glu Asp Phe Leu Ala Lys His Lys
    65                  70                  75 ctg gcc aga gag gat ggg gaa aaa ctg ccg ctg gcc ttt acc ttt tcg       288
Leu Ala Arg Glu Asp Gly Glu Lys Leu Pro Leu Ala Phe Thr Phe Ser
80                  85                  90                  95 tac cca gtc aca cag gac cac atc cgg cat ggg gtc ctg caa cgg tgg       336
Tyr Pro Val Thr Gln Asp His Ile Arg His Gly Val Leu Gln Arg Trp
                100                 105                 110 aca aag ggt ttt gat ata tcc ggt gtt gag ggg gag gat gtc gtc gca       384
Thr Lys Gly Phe Asp Ile Ser Gly Val Glu Gly Glu Asp Val Val Ala
            115                 120                 125 cat ctg gag gag gtg ttt gag aag agg aat gtg ccc gtt agg ctt gtg       432
His Leu Glu Glu Val Phe Glu Lys Arg Asn Val Pro Val Arg Leu Val
        130                 135                 140 gca ctg gtg aat gat aca gtc ggc act ctc atc gcg tct gcc tac aag       480
Ala Leu Val Asn Asp Thr Val Gly Thr Leu Ile Ala Ser Ala Tyr Lys
    145                 150                 155 aac cca gct atc aag atc ggc agc atc ttt gcg acg ggg tgc aat gcc       528
Asn Pro Ala Ile Lys Ile Gly Ser Ile Phe Ala Thr Gly Cys Asn Ala
160                 165                 170                 175 gcc tat atg gag aag gtg tcg cga atc ccc aag att gca gat cac ggc       576
Ala Tyr Met Glu Lys Val Ser Arg Ile Pro Lys Ile Ala Asp His Gly
                180                 185                 190 tcc gag ttc gag agc gac gcc ctc gtc tct atc aac tgc gaa tac ggc       624
Ser Glu Phe Glu Ser Asp Ala Leu Val Ser Ile Asn Cys Glu Tyr Gly
            195                 200                 205 gct ttt gat aac gca cac aag gtc ctc ccc atg acg cgg ttt gac gaa       672
Ala Phe Asp Asn Ala His Lys Val Leu Pro Met Thr Arg Phe Asp Glu
        210                 215                 220
```

```
gag att gat cag acc tct gca agg ccc ggg caa cag gcc tac gag aag       720
Glu Ile Asp Gln Thr Ser Ala Arg Pro Gly Gln Gln Ala Tyr Glu Lys
    225                 230                 235 atg gta gcc ggg atg tac atg ggc gaa cta ctg cgg ctc ctc ctc ctc       768
Met Val Ala Gly Met Tyr Met Gly Glu Leu Leu Arg Leu Leu Leu Leu
240                 245                 250                 255 cac ttg cac gag tcc agt ggg ttt ttc acc gat gcc gag att gac cgg       816
His Leu His Glu Ser Ser Gly Phe Phe Thr Asp Ala Glu Ile Asp Arg
                260                 265                 270 cta cga ggc tat ggc acg atg gat tct gcg tct ctg tcg cga atg gaa       864
Leu Arg Gly Tyr Gly Thr Met Asp Ser Ala Ser Leu Ser Arg Met Glu
            275                 280                 285 gcg gga gga tcc gag gca gag cgg atg agt gac gcc aag tgt ata ttg       912
Ala Gly Gly Ser Glu Ala Glu Arg Met Ser Asp Ala Lys Cys Ile Leu
        290                 295                 300 aag gac ttg tat ggg att gag gcg acc gac gaa gag gca agg gtt tgc       960
Lys Asp Leu Tyr Gly Ile Glu Ala Thr Asp Glu Glu Ala Arg Val Cys
    305                 310                 315 tgc ctc ttg ggg gag att gtg tgc act cgt gca gcg agg tta tat gca      1008
Cys Leu Leu Gly Glu Ile Val Cys Thr Arg Ala Ala Arg Leu Tyr Ala
320                 325                 330                 335 tgc ggt att gca gca ttg tgc cgg aaa cag ggc atc agc gag tgt gcc      1056
Cys Gly Ile Ala Ala Leu Cys Arg Lys Gln Gly Ile Ser Glu Cys Ala
                340                 345                 350 gtc gga gtc gac ggg tcg act ttt gag aag tac tcg cag ttc cgc gaa      1104
Val Gly Val Asp Gly Ser Thr Phe Glu Lys Tyr Ser Gln Phe Arg Glu
            355                 360                 365 cgt gcg gtc gat gcc ctg ggc gag att ctg gac tgg cct gaa ggg caa      1152
Arg Ala Val Asp Ala Leu Gly Glu Ile Leu Asp Trp Pro Glu Gly Gln
        370                 375                 380 cag ctt gtg aag ctg gtc acg gca gag gac ggg tct gga gta ggg tct      1200
Gln Leu Val Lys Leu Val Thr Ala Glu Asp Gly Ser Gly Val Gly Ser
    385                 390                 395 gct ctg att ggg gcc atc aca ctg aat caa                              1230
Ala Leu Ile Gly Ala Ile Thr Leu Asn Gln
400                 405
```

<210> SEQ ID NO 26
<211> LENGTH: 409
<212> TYPE: PRT
<213> ORGANISM: Aspergillus nidulans

<400> SEQUENCE: 26

```
Met Asn Val Thr Trp Val Pro Ser Phe Pro Thr Gly His Glu Thr Gly
1               5                   10                  15

Arg Tyr Leu Ala Ile Asp Met Gly Gly Thr Asn Leu Arg Ile Cys Asp
            20                  25                  30

Val Thr Leu Thr Glu Glu Lys Gly Ala Tyr Thr Ile Glu Gln Asp Lys
        35                  40                  45

Tyr Arg Leu Pro Ile His Leu Arg Lys Gly Lys Val Glu Leu Trp
    50                  55                  60

Glu Phe Ile Ala Ala Lys Leu Glu Asp Phe Leu Ala Lys His Lys Leu
65                  70                  75                  80

Ala Arg Glu Asp Gly Glu Lys Leu Pro Leu Ala Phe Thr Phe Ser Tyr
                85                  90                  95

Pro Val Thr Gln Asp His Ile Arg His Gly Val Leu Gln Arg Trp Thr
            100                 105                 110

Lys Gly Phe Asp Ile Ser Gly Val Glu Gly Glu Asp Val Val Ala His
        115                 120                 125
```

```
Leu Glu Glu Val Phe Glu Lys Arg Asn Val Pro Val Arg Leu Val Ala
    130                 135                 140

Leu Val Asn Asp Thr Val Gly Thr Leu Ile Ala Ser Ala Tyr Lys Asn
145                 150                 155                 160

Pro Ala Ile Lys Ile Gly Ser Ile Phe Ala Thr Gly Cys Asn Ala Ala
                165                 170                 175

Tyr Met Glu Lys Val Ser Arg Ile Pro Lys Ile Ala Asp His Gly Ser
            180                 185                 190

Glu Phe Glu Ser Asp Ala Leu Val Ser Ile Asn Cys Glu Tyr Gly Ala
        195                 200                 205

Phe Asp Asn Ala His Lys Val Leu Pro Met Thr Arg Phe Asp Glu Glu
    210                 215                 220

Ile Asp Gln Thr Ser Ala Arg Pro Gly Gln Gln Ala Tyr Glu Lys Met
225                 230                 235                 240

Val Ala Gly Met Tyr Met Gly Glu Leu Leu Arg Leu Leu Leu Leu His
                245                 250                 255

Leu His Glu Ser Ser Gly Phe Phe Thr Asp Ala Glu Ile Asp Arg Leu
            260                 265                 270

Arg Gly Tyr Gly Thr Met Asp Ser Ala Ser Leu Ser Arg Met Glu Ala
        275                 280                 285

Gly Gly Ser Glu Ala Glu Arg Met Ser Asp Ala Lys Cys Ile Leu Lys
    290                 295                 300

Asp Leu Tyr Gly Ile Glu Ala Thr Asp Glu Glu Ala Arg Val Cys Cys
305                 310                 315                 320

Leu Leu Gly Glu Ile Val Cys Thr Arg Ala Ala Arg Leu Tyr Ala Cys
                325                 330                 335

Gly Ile Ala Ala Leu Cys Arg Lys Gln Gly Ile Ser Glu Cys Ala Val
            340                 345                 350

Gly Val Asp Gly Ser Thr Phe Glu Lys Tyr Ser Gln Phe Arg Glu Arg
        355                 360                 365

Ala Val Asp Ala Leu Gly Glu Ile Leu Asp Trp Pro Glu Gly Gln Gln
    370                 375                 380

Leu Val Lys Leu Val Thr Ala Glu Asp Gly Ser Gly Val Gly Ser Ala
385                 390                 395                 400

Leu Ile Gly Ala Ile Thr Leu Asn Gln
                405

<210> SEQ ID NO 27
<211> LENGTH: 1160
<212> TYPE: DNA
<213> ORGANISM: Aspergillus fumigatus
<220> FEATURE:
<221> NAME/KEY: CDS
<222> LOCATION: (4)..(498)

<400> SEQUENCE: 27 ccg atg aac gtt acc tgg gtg atg ggc ttc ccc gat gga gac gag cag    48
    Met Asn Val Thr Trp Val Met Gly Phe Pro Asp Gly Asp Glu Gln
    1               5                  10                  15 ggg acc ttc ctt gcc ctg gat atg ggt ggc act aac ctc cgc gtc tgt    96
Gly Thr Phe Leu Ala Leu Asp Met Gly Gly Thr Asn Leu Arg Val Cys
            20                  25                  30 gag att acc ttg acg gaa gag aag gga ggc ttc gat atc tgc cag tcc   144
Glu Ile Thr Leu Thr Glu Glu Lys Gly Gly Phe Asp Ile Cys Gln Ser
        35                  40                  45 aag tac cgc atg ccg gaa gaa ctg aag acc gga acc gcc gag gag ctg   192
```

```
Lys Tyr Arg Met Pro Glu Glu Leu Lys Thr Gly Thr Ala Glu Glu Leu
            50                  55                  60 tgg gaa tac atc gcc gac tgc ata cag caa ttc att gag ttc cac cac    240
Trp Glu Tyr Ile Ala Asp Cys Ile Gln Gln Phe Ile Glu Phe His His
 65                  70                  75 gga gag gaa gga ttg aca tca ttg ccc ctg ggt ttc acc ttc tcc tac    288
Gly Glu Glu Gly Leu Thr Ser Leu Pro Leu Gly Phe Thr Phe Ser Tyr
 80                  85                  90                  95 ccg gct aca caa gag tac att gat cat ggt att ctt cag cgc tgg act    336
Pro Ala Thr Gln Glu Tyr Ile Asp His Gly Ile Leu Gln Arg Trp Thr
                100                 105                 110 aag ggc ttc gac att gat ggt gtc gag gga cag gat gtc gtc cct ccc    384
Lys Gly Phe Asp Ile Asp Gly Val Glu Gly Gln Asp Val Val Pro Pro
                115                 120                 125 ctt gag gaa acg ctt aag aga aag gta tac ccg ctc tta gtt gtt gtt    432
Leu Glu Glu Thr Leu Lys Arg Lys Val Tyr Pro Leu Leu Val Val Val
            130                 135                 140 gtt gcc aat cta cgg aca tct aac aat gtg ctt ttc agg gac ttc cta    480
Val Ala Asn Leu Arg Thr Ser Asn Asn Val Leu Phe Arg Asp Phe Leu
145                 150                 155 tca agg tcg ctg ctc tga tcaacgatac cactggaacg ctcatcgcct           528
Ser Arg Ser Leu Leu
160 cggcctacac tgatcccgag atgaagattg gatgtatttt tggtacaggt gtcaatgcgg   588 cctacatgga gaacgttggt tccgtcccta agctggccca catgaacctg ccccccagaca  648 tgccagtggc catcaattgc gagtacggtg ctttcgacaa cgagcacgta gtgttccccct 708 cacaaagtat gatcatatca ttgaccgcga ctctcccccgc cccggccagc aggccttcga  768 gaagatgaca gctggtctct acctgggaga gatcttccgt ctggccctga ttgatcttct   828 ggacagcaga ccaggactga tcttccagaa tcaggacacc agcaagctgc ggaagccgta   888 cttgctggac gcttccttcc tggctgccat cgaggaggat ccctacgaga acttgcagga   948 aacgcaggag ctgttcgagc gcgaattgaa catcaagccc actctggccg agcttgagat  1008 gattcgtcgt ctggccgagc tgatcggtac gcgtgcagct cgtctgtcag cttgcggtgt  1068 ggccgctatc tgcaaaaaga gaacatcga gagctgccac gttggtgcag acggctccgt   1128 cttcaccaag taccctcact cccctcact tc                                 1160

<210> SEQ ID NO 28
<211> LENGTH: 164
<212> TYPE: PRT
<213> ORGANISM: Aspergillus fumigatus

<400> SEQUENCE: 28

Met Asn Val Thr Trp Val Met Gly Phe Pro Asp Gly Asp Glu Gln Gly
  1               5                  10                  15

Thr Phe Leu Ala Leu Asp Met Gly Gly Thr Asn Leu Arg Val Cys Glu
             20                  25                  30

Ile Thr Leu Thr Glu Glu Lys Gly Gly Phe Asp Ile Cys Gln Ser Lys
         35                  40                  45

Tyr Arg Met Pro Glu Glu Leu Lys Thr Gly Thr Ala Glu Glu Leu Trp
     50                  55                  60

Glu Tyr Ile Ala Asp Cys Ile Gln Gln Phe Ile Glu Phe His His Gly
 65                  70                  75                  80

Glu Glu Gly Leu Thr Ser Leu Pro Leu Gly Phe Thr Phe Ser Tyr Pro
                 85                  90                  95
```

```
Ala Thr Gln Glu Tyr Ile Asp His Gly Ile Leu Gln Arg Trp Thr Lys
        100                 105                 110

Gly Phe Asp Ile Asp Gly Val Glu Gly Gln Asp Val Val Pro Pro Leu
    115                 120                 125

Glu Glu Thr Leu Lys Arg Lys Val Tyr Pro Leu Val Val Val
    130                 135                 140

Ala Asn Leu Arg Thr Ser Asn Asn Val Leu Phe Arg Asp Phe Leu Ser
145                 150                 155                 160

Arg Ser Leu Leu

<210> SEQ ID NO 29
<211> LENGTH: 1625
<212> TYPE: DNA
<213> ORGANISM: Aspergillus fumigatus
<220> FEATURE:
<221> NAME/KEY: CDS
<222> LOCATION: (29)..(457)

<400> SEQUENCE: 29
```

| | | |
|---|---|---|
| gtctgccctc ggagggtgcc accgagac atg gct aac tat ctt cta gca cct | | 52 |
|                                Met Ala Asn Tyr Leu Leu Ala Pro | | |
|                                 1               5              | | |

| | | |
|---|---|---|
| act ccc cgc ctg gcc cag aag gtc act ggg gat gcg ctt cag gat gaa | | 100 |
| Thr Pro Arg Leu Ala Gln Lys Val Thr Gly Asp Ala Leu Gln Asp Glu | | |
|     10                  15                  20                 | | |

| | | |
|---|---|---|
| ttc acg cag cta cga gaa ctc ttc act gtg gat tcc gcc aag ctg aag | | 148 |
| Phe Thr Gln Leu Arg Glu Leu Phe Thr Val Asp Ser Ala Lys Leu Lys | | |
| 25                  30                  35                  40 | | |

| | | |
|---|---|---|
| cag att act gac cac ttt gtc cat gaa ctt gag att ggt aag tac att | | 196 |
| Gln Ile Thr Asp His Phe Val His Glu Leu Glu Ile Gly Lys Tyr Ile | | |
|                 45                  50                  55     | | |

| | | |
|---|---|---|
| ctt cct ggc tat ctc gat gcc gta gat gct aac atg ttt cag ggc tca | | 244 |
| Leu Pro Gly Tyr Leu Asp Ala Val Asp Ala Asn Met Phe Gln Gly Ser | | |
|             60                  65                  70         | | |

| | | |
|---|---|---|
| gtg gcc aag gcg gcg aca ttg tat gtc att aca gcc tac tgt cta cct | | 292 |
| Val Ala Lys Ala Ala Thr Leu Tyr Val Ile Thr Ala Tyr Cys Leu Pro | | |
|         75                  80                  85             | | |

| | | |
|---|---|---|
| gct aca ata cag gct aac ggg aac gaa cag cca atg aac cca aca tgg | | 340 |
| Ala Thr Ile Gln Ala Asn Gly Asn Glu Gln Pro Met Asn Pro Thr Trp | | |
|     90                  95                 100                 | | |

| | | |
|---|---|---|
| gta atg gaa ctg ccg cgc ggc gac gaa aag gga gcc ttc ttc acg atg | | 388 |
| Val Met Glu Leu Pro Arg Gly Asp Glu Lys Gly Ala Phe Phe Thr Met | | |
| 105                 110                 115                 120 | | |

| | | |
|---|---|---|
| gac atg gga ggc acc aac ttc cgc gtc tgc aaa gtg aca ctc aac ggc | | 436 |
| Asp Met Gly Gly Thr Asn Phe Arg Val Cys Lys Val Thr Leu Asn Gly | | |
|                 125                 130                 135    | | |

| | | |
|---|---|---|
| acc gca gca aat acg acg tga tccaaatgga caacaagatc cccaagtcgt | | 487 |
| Thr Ala Ala Asn Thr Thr                                        | | |
|                 140                                            | | |

| | |
|---|---|
| tgaagtctgg caccgcagag caactgtggc actacgttgc cgactgcctg cagcagtttg | 547 |
| tcgatcgcta ttccatctcg cagaaagagc tcgcggagac gcctctggcc tttacatttt | 607 |
| cctaccctgt cactcaaaca tccatctcgc atggcatcct ccagcgatgg accaagggat | 667 |
| ttgatatcaa gggtgtcgag gaacagacg ttgttgctgc actgcaaaag gttctcaaag | 727 |
| acaaggtcag tcctacttcg gtcctttttg cctagaaagt tgatattaac ttgactagaa | 787 |
| tctcccgct cggatcgtcg ccttggttaa cgacacagtg ggtaccttaa tggcgtcttc | 847 |
| ctacgtcgac cccaagaccg aaatcggtag catcttcggc acaggcagta acgcagcgta | 907 |

-continued

```
catggagcag tgctccaaga tcccgaaact ggccgatcag catctacccg acgacgcatt    967
catggccatc aactgcgaat acggcgcctt tgataacagc cagcgagtgc tccctttcac   1027
tgtcttcgat gccgagatcg accgcgcttc acctcggccc gggcaacaac gctatgagaa   1087
gatggttgcg ggattctatc tgggtgagat cttccggctc atcttgcttg atctccacaa   1147
ccgcaaggtc atctttgacg gtcagaattc ctcgaaacta agcgaacctt atgtgctgga   1207
ctgctgtttc ctggcgacta ttgagagcga taattctgcg gacctgcaga cagtgaaaga   1267
tacttttgag aaaacactct ccatcacgcc taccccgcct gagctacgct tctgctacga   1327
cctggcgcac acgatttcct tgcgctcggc gaggttatac gcgtgcggca tcgcggcgat   1387
catgaagaag cggggattag aaagctgtca tgttgctgtg gatggctctg tgttcaacaa   1447
gtatccatgt ttcccggaga gggccatcgg ggcgctgcgg gagatcctcg agtggccggc   1507
tgataccccg gatccgatcc ggttgattcc tgctgtggat ggctccagtg tgggagctgc   1567
agtgattgtg tctttgatca gcaagtcgca gcagtcgtaa actattgctt accttctg    1625
```

<210> SEQ ID NO 30
<211> LENGTH: 142
<212> TYPE: PRT
<213> ORGANISM: Aspergillus fumigatus

<400> SEQUENCE: 30

```
Met Ala Asn Tyr Leu Leu Ala Pro Thr Pro Arg Leu Ala Gln Lys Val
1               5                   10                  15
Thr Gly Asp Ala Leu Gln Asp Glu Phe Thr Gln Leu Arg Glu Leu Phe
            20                  25                  30
Thr Val Asp Ser Ala Lys Leu Lys Gln Ile Thr Asp His Phe Val His
        35                  40                  45
Glu Leu Glu Ile Gly Lys Tyr Ile Leu Pro Gly Tyr Leu Asp Ala Val
    50                  55                  60
Asp Ala Asn Met Phe Gln Gly Ser Val Ala Lys Ala Thr Leu Tyr
65                  70                  75                  80
Val Ile Thr Ala Tyr Cys Leu Pro Ala Thr Ile Gln Ala Asn Gly Asn
                85                  90                  95
Glu Gln Pro Met Asn Pro Thr Trp Val Met Glu Leu Pro Arg Gly Asp
            100                 105                 110
Glu Lys Gly Ala Phe Phe Thr Met Asp Met Gly Gly Thr Asn Phe Arg
        115                 120                 125
Val Cys Lys Val Thr Leu Asn Gly Thr Ala Ala Asn Thr Thr
    130                 135                 140
```

<210> SEQ ID NO 31
<211> LENGTH: 1428
<212> TYPE: DNA
<213> ORGANISM: Candida albicans
<220> FEATURE:
<221> NAME/KEY: CDS
<222> LOCATION: (1)..(1428)

<400> SEQUENCE: 31

```
atg gtg cat ctc ggt cca aaa cca gct caa aaa aga aag gga act ttc    48
Met Val His Leu Gly Pro Lys Pro Ala Gln Lys Arg Lys Gly Thr Phe
1               5                   10                  15 act gat gtt tct cct caa tta tta gaa gct ctt aaa cca att caa gag    96
Thr Asp Val Ser Pro Gln Leu Leu Glu Ala Leu Lys Pro Ile Gln Glu
            20                  25                  30 caa ttc acc att tct gca gac aaa ttg aga gct att gtt aaa cat ttc   144
Gln Phe Thr Ile Ser Ala Asp Lys Leu Arg Ala Ile Val Lys His Phe
```

-continued

```
                Gln Phe Thr Ile Ser Ala Asp Lys Leu Arg Ala Ile Val Lys His Phe
                             35                  40                  45 atc tca gaa tta gac cgt ggt tta tca aaa gct ggt ggt aac att cct         192
Ile Ser Glu Leu Asp Arg Gly Leu Ser Lys Ala Gly Gly Asn Ile Pro
 50                  55                  60 atg att cca ggt tgg gtc atg gat ttc cca acc ggt aaa gaa act ggt         240
Met Ile Pro Gly Trp Val Met Asp Phe Pro Thr Gly Lys Glu Thr Gly
 65                  70                  75                  80 tct tat ctt gcc att gac ttg ggt gga acc aac ttg aga gtt gtc ttg         288
Ser Tyr Leu Ala Ile Asp Leu Gly Gly Thr Asn Leu Arg Val Val Leu
                     85                  90                  95 gtt aaa ttg ggc ggt aac aga gac ttt gac acc act caa tcc aag ttt         336
Val Lys Leu Gly Gly Asn Arg Asp Phe Asp Thr Thr Gln Ser Lys Phe
                100                 105                 110 gct ttg cca gct cac atg aga act gcc acc ctg gac gaa tta tgg gat         384
Ala Leu Pro Ala His Met Arg Thr Ala Thr Leu Asp Glu Leu Trp Asp
                115                 120                 125 ttt att gct aaa tgt ttg aaa gag ttt gtt gat gaa atc tac cca gat         432
Phe Ile Ala Lys Cys Leu Lys Glu Phe Val Asp Glu Ile Tyr Pro Asp
            130                 135                 140 ggt tgc agt gaa cca ttg cca ttg ggt ttc aca ttt agt tat cca gct         480
Gly Cys Ser Glu Pro Leu Pro Leu Gly Phe Thr Phe Ser Tyr Pro Ala
145                 150                 155                 160 tct caa aac cgt atc aat gaa ggt atc ttg caa aga tgg act aaa ggc         528
Ser Gln Asn Arg Ile Asn Glu Gly Ile Leu Gln Arg Trp Thr Lys Gly
                    165                 170                 175 tgg tca att gat gga att gaa gga aag gat gtt gtt cca atg ttg caa         576
Trp Ser Ile Asp Gly Ile Glu Gly Lys Asp Val Val Pro Met Leu Gln
                180                 185                 190 aaa gct att aag aaa gtt ggt gtc cca att gat gtt gtt gcg ttg atc         624
Lys Ala Ile Lys Lys Val Gly Val Pro Ile Asp Val Val Ala Leu Ile
            195                 200                 205 aac gat acc aca ggt aca tta gtt gct tct atg tac aca gac cca gaa         672
Asn Asp Thr Thr Gly Thr Leu Val Ala Ser Met Tyr Thr Asp Pro Glu
        210                 215                 220 gct aag atg ggt ttg att ttt ggt act ggt gtc aac ggt gct tat ttc         720
Ala Lys Met Gly Leu Ile Phe Gly Thr Gly Val Asn Gly Ala Tyr Phe
225                 230                 235                 240 gat gtt gtc aag gac att cct aaa tta gaa ggt aaa tgt cca tca gat         768
Asp Val Val Lys Asp Ile Pro Lys Leu Glu Gly Lys Cys Pro Ser Asp
                    245                 250                 255 att cca cca gaa tca cca atg gcc atc aac tgt gag tac ggt tca ttt         816
Ile Pro Pro Glu Ser Pro Met Ala Ile Asn Cys Glu Tyr Gly Ser Phe
                260                 265                 270 gat aac gaa aag tat atc ttg cca aga act aaa tac gat gtt caa att         864
Asp Asn Glu Lys Tyr Ile Leu Pro Arg Thr Lys Tyr Asp Val Gln Ile
            275                 280                 285 gac gaa gaa tca cca aga cca ggt caa caa act ttc gaa aag atg atc         912
Asp Glu Glu Ser Pro Arg Pro Gly Gln Gln Thr Phe Glu Lys Met Ile
        290                 295                 300 tcc ggt tac tat ttg gga gaa gtt ttg aga ttg att tta ttg gaa ttt         960
Ser Gly Tyr Tyr Leu Gly Glu Val Leu Arg Leu Ile Leu Leu Glu Phe
305                 310                 315                 320 gct gaa gag aag aaa ttg atc ttc aaa ggt caa aac ctt gac aag ttg        1008
Ala Glu Glu Lys Lys Leu Ile Phe Lys Gly Gln Asn Leu Asp Lys Leu
                    325                 330                 335 aag gtt cca tac gtc atg gat gcc tct tat cca tcc aaa att gaa gaa        1056
Lys Val Pro Tyr Val Met Asp Ala Ser Tyr Pro Ser Lys Ile Glu Glu
                340                 345                 350
```

-continued

```
gat cca ttt gaa aac ttg tct gat gtc gcc gac tta ttt aga gaa aaa    1104
Asp Pro Phe Glu Asn Leu Ser Asp Val Ala Asp Leu Phe Arg Glu Lys
        355                 360                 365 ttg ggc att gaa acc aca gaa cca gaa aga aag atc atc cgt tgt tta    1152
Leu Gly Ile Glu Thr Thr Glu Pro Glu Arg Lys Ile Ile Arg Cys Leu
    370                 375                 380 gcg gaa ttg att ggt gaa aga tct gct aga ttc tct gtt tgt ggt att    1200
Ala Glu Leu Ile Gly Glu Arg Ser Ala Arg Phe Ser Val Cys Gly Ile
385                 390                 395                 400 gct gct att tgc caa aag aga ggt tac aaa acc gct cat tgt gct gct    1248
Ala Ala Ile Cys Gln Lys Arg Gly Tyr Lys Thr Ala His Cys Ala Ala
                405                 410                 415 gac ggt tca gtg tac aac aag tac cca ggg ttc aaa gaa aga act gcc    1296
Asp Gly Ser Val Tyr Asn Lys Tyr Pro Gly Phe Lys Glu Arg Thr Ala
            420                 425                 430 caa gct tta aga gac atc tac gaa tgg cca gct gat gtc aag gac cca    1344
Gln Ala Leu Arg Asp Ile Tyr Glu Trp Pro Ala Asp Val Lys Asp Pro
        435                 440                 445 atc atc att gtt cca gct gaa gat ggt agt ggt gtt ggt gct gcc gtt    1392
Ile Ile Ile Val Pro Ala Glu Asp Gly Ser Gly Val Gly Ala Ala Val
    450                 455                 460 att gct gct ttg acc gaa aag aga tta aaa gaa ggt                    1428
Ile Ala Ala Leu Thr Glu Lys Arg Leu Lys Glu Gly
465                 470                 475
```

<210> SEQ ID NO 32
<211> LENGTH: 476
<212> TYPE: PRT
<213> ORGANISM: Candida albicans

<400> SEQUENCE: 32

```
Met Val His Leu Gly Pro Lys Pro Ala Gln Lys Arg Lys Gly Thr Phe
1               5                   10                  15

Thr Asp Val Ser Pro Gln Leu Leu Glu Ala Leu Lys Pro Ile Gln Glu
            20                  25                  30

Gln Phe Thr Ile Ser Ala Asp Lys Leu Arg Ala Ile Val Lys His Phe
        35                  40                  45

Ile Ser Glu Leu Asp Arg Gly Leu Ser Lys Ala Gly Gly Asn Ile Pro
    50                  55                  60

Met Ile Pro Gly Trp Val Met Asp Phe Pro Thr Gly Lys Glu Thr Gly
65                  70                  75                  80

Ser Tyr Leu Ala Ile Asp Leu Gly Gly Thr Asn Leu Arg Val Val Leu
                85                  90                  95

Val Lys Leu Gly Gly Asn Arg Asp Phe Asp Thr Thr Gln Ser Lys Phe
            100                 105                 110

Ala Leu Pro Ala His Met Arg Thr Ala Thr Leu Asp Glu Leu Trp Asp
        115                 120                 125

Phe Ile Ala Lys Cys Leu Lys Glu Phe Val Asp Glu Ile Tyr Pro Asp
    130                 135                 140

Gly Cys Ser Glu Pro Leu Pro Leu Gly Phe Thr Phe Ser Tyr Pro Ala
145                 150                 155                 160

Ser Gln Asn Arg Ile Asn Glu Gly Ile Leu Gln Arg Trp Thr Lys Gly
                165                 170                 175

Trp Ser Ile Asp Gly Ile Glu Gly Lys Asp Val Val Pro Met Leu Gln
            180                 185                 190

Lys Ala Ile Lys Lys Val Gly Val Pro Ile Asp Val Val Ala Leu Ile
        195                 200                 205
```

```
Asn Asp Thr Thr Gly Thr Leu Val Ala Ser Met Tyr Thr Asp Pro Glu
    210                 215                 220

Ala Lys Met Gly Leu Ile Phe Gly Thr Gly Val Asn Gly Ala Tyr Phe
225                 230                 235                 240

Asp Val Val Lys Asp Ile Pro Lys Leu Glu Gly Lys Cys Pro Ser Asp
                245                 250                 255

Ile Pro Pro Glu Ser Pro Met Ala Ile Asn Cys Glu Tyr Gly Ser Phe
                260                 265                 270

Asp Asn Glu Lys Tyr Ile Leu Pro Arg Thr Lys Tyr Asp Val Gln Ile
            275                 280                 285

Asp Glu Glu Ser Pro Arg Pro Gly Gln Gln Thr Phe Glu Lys Met Ile
    290                 295                 300

Ser Gly Tyr Tyr Leu Gly Glu Val Leu Arg Leu Ile Leu Leu Glu Phe
305                 310                 315                 320

Ala Glu Glu Lys Lys Leu Ile Phe Lys Gly Gln Asn Leu Asp Lys Leu
                325                 330                 335

Lys Val Pro Tyr Val Met Asp Ala Ser Tyr Pro Ser Lys Ile Glu Glu
                340                 345                 350

Asp Pro Phe Glu Asn Leu Ser Asp Val Ala Asp Leu Phe Arg Glu Lys
            355                 360                 365

Leu Gly Ile Glu Thr Thr Glu Pro Glu Arg Lys Ile Ile Arg Cys Leu
    370                 375                 380

Ala Glu Leu Ile Gly Glu Arg Ser Ala Arg Phe Ser Val Cys Gly Ile
385                 390                 395                 400

Ala Ala Ile Cys Gln Lys Arg Gly Tyr Lys Thr Ala His Cys Ala Ala
                405                 410                 415

Asp Gly Ser Val Tyr Asn Lys Tyr Pro Gly Phe Lys Glu Arg Thr Ala
            420                 425                 430

Gln Ala Leu Arg Asp Ile Tyr Glu Trp Pro Ala Asp Val Lys Asp Pro
    435                 440                 445

Ile Ile Ile Val Pro Ala Glu Asp Gly Ser Gly Val Gly Ala Ala Val
    450                 455                 460

Ile Ala Ala Leu Thr Glu Lys Arg Leu Lys Glu Gly
465                 470                 475

<210> SEQ ID NO 33
<211> LENGTH: 11546
<212> TYPE: DNA
<213> ORGANISM: Artificial
<220> FEATURE:
<223> OTHER INFORMATION: plasmid containing construct for corn
      transformation

<400> SEQUENCE: 33
gcaactgttg ggaagggcga tcggtgcggg cctcttcgct attacgccag ctggcgaaag      60
ggggatgtgc tgcaaggcga ttaagttggg taacgccagg gttttcccag tcacgacgtt    120
gtaaaacgac ggccagtgaa ttgcggccac gcgtggtacc aagcttcccg atcctatctg    180
tcacttcatc aaaaggacag tagaaaagga aggtggcacc tacaaatgcc atcattgcga    240
taaaggaaag gctatcattc aagatgcctc tgccgacagt ggtcccaaag atggaccccc    300
acccacgagg agcatcgtgg aaaagaagac gttccaacc acgtcttcaa agcaagtgga    360
ttgatgtgat acttccactg acgtaaggga atgacgcaca atcccactat ccttcgcaag    420
acccttcctc tatataagga agttcatttc atttggagag acacgctga aatcaccagt    480 ctctctctac aagatcgggg atctctagct agacgatcgt tcgcatgat tgaacaagat    540
```

```
ggattgcacg caggttctcc ggccgcttgg gtggagaggc tattcggcta tgactgggca    600
caacagacaa tcggctgctc tgatgccgcc gtgttccggc tgtcagcgca ggggcgcccg    660
gttcttttg tcaagaccga cctgtccggt gccctgaatg aactgcagga cgaggcagcg    720
cggctatcgt ggctggccac gacgggcgtt ccttgcgcag ctgtgctcga cgttgtcact    780
gaagcgggaa gggactggct gctattgggc gaagtgccgg ggcaggatct cctgtcatct    840
caccttgctc ctgccgagaa agtatccatc atggctgatg caatgcggcg gctgcatacg    900
cttgatccgg ctacctgccc attcgaccac caagcgaaac atcgcatcga gcgagcacgt    960
actcggatgg aagccggtct tgtcgatcag gatgatctgg acgaagagca tcagggctc    1020
gcgccagccg aactgttcgc caggctcaag gcgcgcatgc ccgacggcga ggatctcgtc    1080
gtgacccatg gcgatgcctg cttgccgaat atcatggtgg aaaatggccg cttttctgga    1140
ttcatcgact gtggccggct gggtgtggcg gaccgctatc aggacatagc gttggctacc    1200
cgtgatattg ctgaagagct tggcggcgaa tgggctgacc gcttcctcgt gctttacggt    1260
atcgccgctc ccgattcgca gcgcatcgcc ttctatcgcc ttcttgacga gttcttctga    1320
gcgggactct ggggttcgaa atgaccgacc aagcgacgcc caacctgcca tcacgagatt    1380
tcgattccac cgccgccttc tatgaaaggt tgggcttcgg aatcgttttc cgggacgccg    1440
gctggatgat cctccagcgc ggggatctca tgctggagtt cttcgccac ccccggatcc    1500
ccatgggaat tcccgatcgt tcaaacattt ggcaataaag tttcttaaga ttgaatcctg    1560
ttgccggtct tgcgatgatt atcatataat ttctgttgaa ttacgttaag catgtaataa    1620
ttaacatgta atgcatgacg ttatttatga gatgggtttt tatgattaga gtcccgcaat    1680
tatacattta atacgcgata gaaaacaaaa tatagcgcgc aaactaggat aaattatcgc    1740
gcgcggtgtc atctatgtta ctagatcggg gatatcccg cggccgcgtt aacaagctcc    1800
ctcgcttcac tccaagctcc acggcggcg cttcttgccc ctgcaatcac tggccagcct    1860
gcccaagagg ataaaagtga gagaaagaga ggaggaaggg agatgagggg aaagagggag    1920
gtgatgacat ggattactga tatgtagggt tcacgtgggt tccacgctga ctcagccgcc    1980
acgtcggata aaccgggat caaagctacc gaatgaccta aagtgaacag ttttgtaaat    2040
tgagggatgt catgtatccg gttttgtggt tgatggacga ttttgtaact cgatgacaaa    2100
ttgagcgacc tgcggtgtac tttttccttc cgccctgtgt ggaggcccaa acattcagcc    2160
cattcccaac ctggcactga catgcgggcc attccaaagc cttgcacagt ttcacctctc    2220
acccgcgcct ccgcttcctc ccgcctcccc aaacgatgcc gcctccgcct ccgtcttccc    2280
gtctcctcgc cctcctctcc gcgcgccgcc cgccgcccc gctccgccgc ctcctccaga    2340
tccacgccca cctcctcgcc gccggcctcc ttcaagactt ctcctccctc ctcgccgccg    2400
cctacgcgct ctccaccacc gccaccgcca cggacgcccg cacctcgccg ccctccccgc    2460
tccgccacgc gctcgcgctc ctctcctcgc tcccggcctc cgcctacaac gccgccatcc    2520
gagcactctc cctctccgac gacgcgacc gccatggcca cggcgtcgtc cgccgctgcc    2580
tcccgctcta ccgcgccctc ctccgctccg gaccgcgcg ccccgaccac ctcacgttcc    2640
cgttcctgct caaggcctgc gcgcgcctgc gggagtgggg atacggcgac gcggccctcg    2700
cgcacgtcct ccgcctcggc ctcgactccg acgtcttcgt ggtgaacgcg ccacgcact    2760
tcctatcgat ccgcgggccc atggaggacg cacgcaggct gttcgaccga agtcctgtga    2820
gggacttggt gtcgtggaac acgctgatcg gagggtacgt gcggcggggg aacccagcgg    2880
```

-continued

```
aggcgctgga gctgttctgg aggatggtgg cagaggatgc agtggtgagg cctgatgagg    2940
tcacgatgat cgcggctgtg tcggggtgtg ggcagatgcg tgacctggag cttgggaggc    3000
ggcttcatgg gttcgtggat agtgacggag tgagttgcac tgtgaggctg atgaatgcgc    3060
tgatggatat gtacatcaag tgtggcagtt tagagatggc aaagtctgtg ttcgagagga    3120
tcgagcacag gacagttgtc tcttggacga cgatgatcgt ggggtttgcc aagttcggat    3180
tgatggacga tgcacgtaaa gtgtttgatg agatgcctga aagggatgtg ttcccatgga    3240
atgcactcat gaccggttat gtgcagtgta agcagtgcaa ggaggccctt tccttgtttc    3300
atgagatgca ggaagcaagt gtggtgcctg atgagatcac aatggtcaat cttctaactg    3360
cttgttcgca gctcggagca ttagaaatgg ggatgtgggt tcaccggtac attgagaaac    3420
atcgccttgt atttagtgtt gcgcttggca catctctcat tgacatgtac gctaagtgtg    3480
gaaacattga gaaagctatc cacatttttca agaaattcc cgagaaaaat gcactcacat    3540
ggacagcaat gatatgtggt ctagcaaatc atggacatgc caatgaggcc atagagcact    3600
tccggacaat gatagagctt ggacagaagc cagatgagat tacgtttata ggtgttcttt    3660
cagcatgctg tcatgctggt ttggtgaaag aaggtcggga ttttttctct ctgatggaga    3720
caaaatatca tcttgagagg aaaatgaaac attattcatg tatgatagac ttactaggca    3780
gggcaggcca tttagacgaa gcagagcagc tagtaaacac tatgcctatg aacctgatg    3840
cagtagtttg gggtgctatc ttctttgctt gtaggatgca aggtaatatc tctcttggag    3900
aaaaggcagc aatgaaattg gtagaaattg atcctagtga tagtgaaatc tatgtgctac    3960
tggctaatat gtatgcagaa gcgaacatga ggaagaaggc tgacaaagtc agggctatga    4020
tgagacattt gggagtggag aaagttcctg ggtgtagctg cattgagttg aatggtgtgg    4080
ttcatgaatt tatcgtgaag gacaagtcac atatggatag tcatgctatt tatgactgct    4140
tgcatgagat caccctacaa ataaagcata ctgcagattt gcttagcatt tctgcggctg    4200
gtgcggtgta gtgttctgtt ggctggaaca gctggctgag ctgtgcaaga tgatatgtgc    4260
agttgtgatg cacaattcac agatgcagga actcgatcat gctgatttgt gctggtttgc    4320
caggccatgt tctgagaagg gtatacttca tgttgattac tatctgaggc attccccgag    4380
aatttctgg tcgttcttttt gcagcttgat gtcaatggaa acaatatgtt ccactacata    4440
ttgcaaagtt cttgtatgct ctttactcaa ccctcacgtg cggagcactt cctgggtaag    4500
tgtggttctc atgctctgtt ttgcctcctc catttctcct ccgttgcatt taaagtcaca    4560
tcccctcct caggttttct ccattagctc tctgtagtcc ttgctgtact ctccttggta    4620
ttccatgctg tcctactact tgcttcatcc ccttctacat tttgttctgg tttttggcct    4680
gcatttcgga tcatgatgta tgtgatttcc aatctgctgc aatatgaatg agactctgt    4740
gctaaccatc aacaacatga aatgcttatg aggcctttgc tgagcagcca atcttgcctg    4800
tgtttatgtc ttcacaggcc gaattcctct gttttgtttt tcaccctcaa tatttggaaa    4860
catttatcta ggttgtttgt gtccaggcct ataaatcata catgatgttg tcgtattgga    4920
tgtgaatgtg gtggcgtgtt cagtgccttg gatttgagtt tgatgagagt tgcttctggg    4980
tcaccactca ccattatcga tgctcctctt cagcataagg taaaagtctt ccctgtttac    5040
gttattttac ccactatggt tgcttgggtt ggttttttcc tgattgctta tgccatggaa    5100
agtcatttga tatgttgaac ttgaattaac tgtagaattg tatacatgtt ccatttgtgt    5160
tgtacttcct tctttttctat tagtagcctc agatgagtg gaaaaaaaca gattatataa    5220
cttgccctat aaatcatttg aaaaaaatat tgtacagtga gaaattgata tatagtgaat    5280
```

```
ttttaagagc atgttttcct aaagaagtat atattttcta tgtacaaagg ccattgaagt    5340
aattgtagat acaggataat gtagactttt tggacttaca ctgctacctt taagtaacaa    5400
tcatgagcaa tagtgttgca atgatattta ggctgcattc gtttactctc ttgatttcca    5460
tgagcacgct tcccaaactg ttaaactctg tgttttttgc caaaaaaaaa tgtataggaa    5520
agttgctttt aaaaaatcat atcaatccat tttttaagtt atagctaata cttaattaat    5580
catgcgctaa taagtcactc tgttttttcgt actagagaga ttgttttgaa ccagcactca    5640
agaacacagc cttaacccag ccaaataatg ctacaaccta ccagtccaca cctcttgtaa    5700
agcatttgtt gcatggaaaa gctaagatga cagcaacctg ttcaggaaaa caactgacaa    5760
ggtcataggg agagggagct tttggaaagg tgccgtgcag ttcaaacaat tagttagcag    5820
tagggtgttg gttttttgctc acagcaataa gaagttaatc atggtgtagg caacccaaat    5880
aaaacaccaa aatatgcaca aggcagtttg ttgtattctg tagtacagac aaaactaaaa    5940
gtaatgaaag aagatgtggt gttagaaaag gaaacaatat catgagtaat gtgtgagcat    6000
tatgggacca cgaaataaaa agaacatttt gatgagtcgt gtatcctcga tgagcctcaa    6060
aagttctctc accccggata agaaaccctt aagcaatgtg caaagtttgc attctccact    6120
gacataatgc aaaataagat atcatcgatg acatagcaac tcatgcatca tatcatgcct    6180
ctctcaacct attcattcct actcatctac ataagtatct tcagctaaat gttagaacat    6240
aaacccataa gtcacgtttg atgagtatta ggcgtgacac atgacaaatc acagactcaa    6300
gcaagataaa gcaaaatgat gtgtacataa aactccagag ctatatgtca tattgcaaaa    6360
agaggagagc ttataagaca aggcatgact cacaaaaatt catttgcctt tcgtgtcaaa    6420
aagaggaggg ctttacatta tccatgtcat attgcaaaag aaagagagaa agaacaacac    6480
aatgctgcgt caattataca tatctgtatg tccatcatta ttcatccacc tttcgtgtac    6540
cacacttcat atatcatgag tcacttcatg tctggacatt aacaaactct atcttaacat    6600
ttagatgcaa gagccttttat ctcactataa atgcacgatg atttctcatt gtttctcaca    6660
aaaagcattc agttcattag atctatcgat tctagaacca tcttccacac actcaagcca    6720
cactattgga gaacacacag ggacaacaca ccataagatc caagggaggc ctccgccgcc    6780
gccggtaacc accccgcccc tctcctcttt cttcttcctccgt ttttttttcc gtctcggtct    6840
cgatctttgg ccttggtagt ttgggtgggc gagaggcggc ttcgtgcgcg cccagatcgg    6900
tgcgcgggag gggcgggatc tcgcggctgg ggctctcgcc ggcgtggatc cggcccggat    6960
ctcgcgggga atgggctct cggatgtaga tctgcgatcc gccgttgttg ggggagatga    7020 tgggggttt aaaattttccg ccgtgctaaa caagatcagg aagagggaa aagggcacta    7080 tggtttatat ttttatatat ttctgctgct tcgtcaggct tagatgtgct agatctttct    7140
ttcttctttt tgtgggtaga atttgaatcc ctcagcattg ttcatcggta gttttttcttt    7200 tcatgatttg tgacaaatgc agcctcgtgc ggagcttttt tgtaggtaga agtgatcaac    7260
catagatcca tggttcattt aggtccaaag aaaccacagg ctagaaaggg ttccatggct    7320
gatgtgccca aggaattgat ggatgaaatt catcagttgg aagatatgtt tacagttgac    7380
agcgagacct tgagaaaggt tgttaagcac tttatcgacg aattgaataa aggttttgaca    7440 aagaagggag gtaacattcc aatgattccc ggttgggtca tggaattccc aacaggtaaa    7500
gaatctggta actatttggc cattgatttg ggtggtacta acttaagagt cgtgttggtc    7560
aagttgagcg gtaaccatac ctttgacacc actcaatcca agtataaact accacatgac    7620
```

-continued

```
atgagaacca ctaagcacca agaggagtta tggtccttta ttgccgactc tttgaaggac    7680
tttatggtcg agcaagaatt gctaaacacc aaggacacct taccattagg tttcaccttc    7740
tcgtacccag cttcccaaaa caagattaac gaaggtattt tgcaaagatg gaccaagggt    7800
ttcgatattc caaatgtcga aggccacgat gtcgtcccat tgctacaaaa cgaaatttcc    7860
aagagagagt tgcctattga aattgtagca ttgattaatg atactgtcgg tactttagtt    7920
gcctcatact acactgaccc agagactaag atgggtgtga ttttcggtac tggtgtcaac    7980
ggtgctttct atgatgttgt tccgatatc gaaaagttgg agggcaaatt agcagacgat    8040
attccaagta actctccaat ggctatcaat tgtgaatatg gttccttcga taatgaacat    8100
ttggtcttgc caagaaccaa gtacgatgtt gctgtcgacg aacaatctcc aagacctggt    8160
caacaagctt ttgaaaagat gacctccggt tactacttgg gtgaattgtt gcgtctagtg    8220
ttacttgaat taaacgagaa gggcttgatg ttgaaggatc aagatctaag caagttgaaa    8280
caaccataca tcatggatac ctcctaccca gcaagaatcg aggatgatcc atttgaaaac    8340
ttggaagata ctgatgacat cttccaaaag gactttggtg tcaagaccac tctgccagaa    8400
cgtaagttga ttagaagact tgtgaattga tcggtacca gagctgctag attagctgtt    8460
tgtggtattg ccgctatttg ccaaaagaga ggttacaaga ctggtcacat tgccgctgac    8520
ggttctgtct ataacaaata cccaggtttc aaggaagccg ccgctaaggg tttgagagat    8580
atctatggat ggactggtgg cgcaagcaac gatccaatta cgattgttcc agctgaggat    8640
ggttccggtg caggtgctgc tgttattgct gcattgtccg aaaaaagaat tgccgaaggt    8700
aagtctcttg gtatcattgg cgcttaactc gaggccgcca ccgcggtgga gctctagaag    8760
gcctgaattc gagctcggta ccggatccaa ttcccgatcg ttcaaacatt tggcaataaa    8820
gtttcttaag attgaatcct gttgccggtc ttgcgatgat tatcatataa tttctgttga    8880
attacgttaa gcatgtaata attaacatgt aatgcatgac gttatttatg agatgggttt    8940
ttatgattag agtcccgcaa ttatacattt aatacgcgat agaaaacaaa atatagcgcg    9000
caaactagga taaattatcg cgcgcggtgt catctatgtt actagatcgg ggatcgatcc    9060
ccgggcggcc gcggggaatt cggtaccaag cttacgcgtg gccgcagctt ggcgtaatca    9120
tggtcatagc tgtttcctgt gtgaaattgt tatccgctca caattccaca caacatacga    9180
gccgaagca taaagtgtaa agcctggggt gcctaatgag tgagctaact cacattaatt    9240
gcgttgcgct cactgcccgc tttccagtcg ggaaacctgt cgtgccagct gcattaatga    9300
atcggccaac gcgcgggag aggcggtttg cgtattgggc gctcttccgc ttcctcgctc    9360
actgactcgc tgcgctcggt cgttcggctg cggcgagcgg tatcagctca ctcaaaggcg    9420
gtaatacggt tatccacaga atcagggat aacgcaggaa agaacatgtg agcaaaaggc    9480
cagcaaaagg ccaggaaccg taaaaaggcc gcgttgctgg cgtttttcca taggctccgc    9540
cccctgacg agcatcacaa aaatcgacgc tcaagtcaga ggtggcgaaa cccgacagga    9600
ctataaagat accaggcgtt tcccctgga agctccctcg tgcgctctcc tgttccgacc    9660
ctgccgctta ccggatacct gtccgccttt ctcccttcgg gaagcgtggc gctttctcaa    9720
tgctcacgct gtaggtatct cagttcggtg taggtcgttc gctccaagct gggctgtgtg    9780
cacgaacccc ccgttcagcc cgaccgctgc gccttatccg gtaactatcg tcttgagtcc    9840
aacccggtaa gacacgactt atcgccactg gcagcagcca ctggtaacag gattagcaga    9900
gcgaggtatg taggcggtgc tacagagttc ttgaagtggg gcctaactac ggctacact    9960
agaaggacag tatttggtat ctgcgctctg ctgaagccag ttaccttcgg aaaaagagtt   10020
```

```
ggtagctctt gatccggcaa acaaaccacc gctggtagcg gtggttttttt tgtttgcaag    10080 cagcagatta cgcgcagaaa aaaggatct caagaagatc ctttgatctt ttctacgggg     10140
tctgacgctc agtggaacga aaactcacgt taagggattt tggtcatgag attatcaaaa    10200
aggatcttca cctagatcct tttggggtgg gcgaagaact ccagcatgag atccccgcgc    10260
tggaggatca tccagccggc gtcccggaaa acgattccga agcccaacct tcatagaag      10320 gcggcggtgg aatcgaaatc tcgtgatggc aggttgggcg tcgcttggtc ggtcatttcg    10380
aaccccagag tcccgctcag aagaactcgt caagaaggcg atagaaggcg atgcgctgcg    10440
aatcgggagc ggcgataccg taaagcacga ggaagcggtc agcccattcg ccgccaagct    10500
cttcagcaat atcacgggta gccaacgcta tgtcctgata gcggtccgcc acacccagcc    10560
ggccacagtc gatgaatcca gaaaagcggc catttttcca catgatattc ggcaagcagg    10620
catcgccatg ggtcacgacg agatcctcgc cgtcgggcat gcgcgccttg agcctggcga    10680
acagttcggc tggcgcgagc ccctgatgct cttcgtccag atcatcctga tcgacaagac    10740
cggcttccat ccgagtacgt gctcgctcga tgcgatgttt cgcttggtgg tcgaatgggc    10800
aggtagccgg atcaagcgta tgcagccgcc gcattgcatc agccatgatg gatactttct    10860
cggcaggagc aaggtgagat gacaggagat cctgccccgg cacttcgccc aatagcagcc    10920
agtcccttcc cgcttcagtg acaacgtcga gcacagctgc gcaaggaacg cccgtcgtgg    10980
ccagccacga tagccgcgct gcctcgtcct gcagttcatt cagggcaccg gacaggtcgg    11040
tcttgacaaa aagaaccggg cgcccctgcg ctgacagccg aacacggcg gcatcagagc     11100 agccgattgt ctgttgtgcc cagtcatagc cgaatagcct ctccacccaa gcggccggag    11160
aacctgcgtg caatccatct tgttcaatca tgcgaaacga tcctcatcct gtctcttgat    11220
cagatcttga tccctgcgc catcagatcc ttggcggcaa aaagccatc cagtttactt       11280 tgcagggctt cccaaccttta ccagagggcg ccccagctgg caattccggt tcgcttgctg   11340
tccataaaac cgcccagtct agctatcgcc atgtaagccc actgcaagct acctgctttc    11400
tctttgcgct tgcgttttcc cttgtccaga tagcccagta gctgacattc atccggggtc    11460
agcaccgttt ctgcggactg gctttctacg tgttccgctt cctttagcag cccttgcgcc    11520
ctgagtgctt gcggcagcgt gaagct                                         11546
```

<210> SEQ ID NO 34
<211> LENGTH: 3034
<212> TYPE: DNA
<213> ORGANISM: Artificial
<220> FEATURE:
<223> OTHER INFORMATION: Artificial sequence inserted into corn
      germplasm

<400> SEQUENCE: 34

```
gaaagaagat gtggtgttag aaaaggaaac aatatcatga gtaatgtgtg agcattatgg      60
gaccacgaaa taaaagaac attttgatga gtcgtgtatc ctcgatgagc ctcaaaagtt      120
ctctcacccc ggataagaaa cccttaagca atgtgcaaag tttgcattct ccactgacat     180
aatgcaaaat aagatatcat cgatgacata gcaactcatg catcatatca tgcctctctc     240
aacctattca ttcctactca tctacataag tatcttcagc taaatgttag aacataaacc     300
cataagtcac gtttgatgag tattaggcgt gacacatgac aaatcacaga ctcaagcaag    360
ataaagcaaa atgatgtgta cataaaactc cagagctata tgtcatattg caaaagagg      420 agagcttata agacaaggca tgactcacaa aaattcattt gcctttcgtg tcaaaagag      480
```

```
gagggcttta cattatccat gtcatattgc aaaagaaaga gagaaagaac aacacaatgc      540
tgcgtcaatt atacatatct gtatgtccat cattattcat ccacctttcg tgtaccacac      600
ttcatatatc atgagtcact tcatgtctgg acattaacaa actctatctt aacatttaga      660
tgcaagagcc tttatctcac tataaatgca cgatgatttc tcattgtttc tcacaaaaag      720
cattcagttc attagatcta tcgattctag aaccatcttc cacacactca agccacacta      780
ttggagaaca cacagggaca acacaccata agatccaagg gaggcctccg ccgccgccgg      840
taaccacccc gccctctcc tctttctttc tccgttttt tttccgtctc ggtctcgatc         900
tttggccttg gtagtttggg tgggcgagag gcggcttcgt gcgcgcccag atcggtgcgc      960
gggaggggcg ggatctcgcg gctgggctc tcgccggcgt ggatccggcc cggatctcgc      1020
ggggaatggg gctctcggat gtagatctgc gatccgccgt tgttggggga gatgatgggg     1080
ggtttaaaat ttccgccgtg ctaaacaaga tcaggaagag gggaaaaggg cactatggtt      1140 tatatttta tatatttctg ctgcttcgtc aggcttagat gtgctagatc tttcttctt       1200 cttttgtgg gtagaatttg aatccctcag cattgttcat cggtagtttt tcttttcatg      1260
atttgtgaca aatgcagcct cgtgcggagc tttttgtag gtagaagtga tcaaccatag     1320
atccatggtt catttaggtc caaagaaacc acaggctaga aagggttcca tggctgatgt      1380
gcccaaggaa ttgatggatg aaattcatca gttggaagat atgtttacag ttgacagcga      1440
gaccttgaga aaggttgtta agcactttat cgacgaattg aataaaggtt tgacaaagaa      1500
gggaggtaac attccaatga ttcccggttg ggtcatggaa ttcccaacag gtaaagaatc      1560
tggtaactat ttggccattg atttgggtgg tactaactta agagtcgtgt tggtcaagtt      1620
gagcggtaac atacctttg acaccactca atccaagtat aaactaccac atgacatgag      1680
aaccactaag caccaagagg agttatggtc ctttattgcc gactctttga aggactttat      1740
ggtcgagcaa gaattgctaa acaccaagga caccttacca ttaggtttca ccttctcgta      1800
cccagcttcc caaaacaaga ttaacgaagg tattttgcaa agatggacca agggtttcga      1860
tattccaaat gtcgaaggcc acgatgtcgt cccattgcta caaaacgaaa tttccaagag      1920
agagttgcct attgaaattg tagcattgat taatgatact gtcggtactt tagttgcctc     1980
atactacact gacccagaga ctaagatggg tgtgattttc ggtactggtg tcaacggtgc     2040
tttctatgat gttgtttccg atatcgaaaa gttggagggc aaattagcag acgatattcc      2100
aagtaactct ccaatggcta tcaattgtga atatggttcc ttcgataatg aacatttggt      2160
cttgccaaga accaagtacg atgttgctgt cgacgaacaa tctccaagac tggtcaaca      2220 agcttttgaa aagatgacct ccggttacta cttgggtgaa ttgttgcgtc tagtgttact     2280
tgaattaaac gagaagggct tgatgttgaa ggatcaagat ctaagcaagt tgaaacaacc      2340
atacatcatg gataccctcct acccagcaag aatcgaggat gatccatttg aaaacttgga      2400
agatactgat gacatcttcc aaaaggactt tggtgtcaag accactctgc cagaacgtaa      2460
gttgattaga agactttgtg aattgatcgg taccagagct gctagattag ctgtttgtgg     2520
tattgccgct atttgccaaa agagaggtta caagactggt cacattgccg ctgacggttc      2580
tgtctataac aaatacccag gtttcaagga agccgccgct aagggtttga gagatatcta      2640
tggatggact ggtggcgcaa gcaacgatcc aattacgatt gttccagctg aggatggttc      2700
cggtgcaggt gctgctgtta ttgctgcatt gtccgaaaaa agaattgccg aaggtaagtc      2760
tcttggtatc attggcgctt aactcgaggc cgccaccgcg gtggagctct agaaggcctg     2820
```

-continued

```
aattcgagct cggtaccgga tccaattccc gatcgttcaa acatttggca ataaagtttc      2880
ttaagattga atcctgttgc cggtcttgcg atgattatca tataatttct gttgaattac      2940
gttaagcatg taataattaa catgtaatgc atgacgttat ttatgagatg ggtttttatg      3000
attagagtcc cgcaattata catttaatac gcga                                  3034
```